United States Patent
Patel et al.

(10) Patent No.: US 11,312,998 B2
(45) Date of Patent: Apr. 26, 2022

(54) METHODS FOR SELECTING THERAPY FOR A CANCER PATIENT

(71) Applicant: The United States of America, as represented by the Secretary, Department of Health and Human Services, Bethesda, MD (US)

(72) Inventors: Shashankkumar J. Patel, Clarksburg, MD (US); Nicholas P. Restifo, Chevy Chase, MD (US)

(73) Assignee: The United States of America, as represented by the Secretary, Department of Health and Human Services, Bethesda, MD (US)

(*) Notice: Subject to any disclaimer, the term of this patent is extended or adjusted under 35 U.S.C. 154(b) by 213 days.

(21) Appl. No.: 16/347,778

(22) PCT Filed: Nov. 7, 2017

(86) PCT No.: PCT/US2017/060304
§ 371 (c)(1),
(2) Date: May 6, 2019

(87) PCT Pub. No.: WO2018/085802
PCT Pub. Date: May 11, 2018

(65) Prior Publication Data
US 2019/0316206 A1    Oct. 17, 2019

Related U.S. Application Data

(60) Provisional application No. 62/418,461, filed on Nov. 7, 2016.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

2017/0299594 A1* 10/2017 Depinho .......... A61P 35/00
2018/0201901 A1*  7/2018 Duchateau ........ A61K 35/17

FOREIGN PATENT DOCUMENTS

WO   WO 2014/168874 A2   10/2014
WO   WO 2016/100975 A1    6/2016
WO   WO 2018/085802 A1    5/2018

OTHER PUBLICATIONS

Zaretsky et al. Mutations Associated with Acquired Resistance to PD-1 Blockade in Melanoma. N Engl J Med. Sep. 2016 ; 375(9): 819-829. (Year: 2016).*
Farazi et al. miRNAs in human cancer (Review). J Pathol; 2011; 223: 102-115. (Year: 2011).*
Restifo et al. Adoptive immunotherapy for cancer: harnessing the T cell response (Review). Nature Reviews Immunology; 2012; 12: 269-281. (Year: 2012).*
Roche et al. Apelin (APLN) and Apelin Receptor (APLNR) in Human Ovary: Expression, Signaling, and Regulation of Steroidogenesis in Primary Human Luteinized Granulosa Cells. Biology of Reproduction; Sep. 2016; 95(5): 104, 1-12. (Year: 2016).*
Kidoya et al. The apelin/APJ system induces maturation of the tumor vasculature and improves the efficiency of immune therapy. Oncogene; 2012; 31: 3254-3264. (Year: 2012).*
Dougan and Dranoff. Immune Therapy for Cancer. Annu. Rev. Immunol.; 2009; 27:83-117. (Year: 2009).*
Zaretsky et al., Mutations Associated with Acquired Resistance to PD-1 Blockade in Melanoma. The New England Journal of Medicine;Sep. 2016; 375(9): 819-829. (Year: 2016).*
Kidoya et al. Oncogene; 2012; 31: 3254-3264. (Year: 2012).*
Blank et al., "The 'cancer immunogram'," *Science*, 352(6286): 658-660 (2016).
Bolger et al., "Trimmomatic: a flexible trimmer for Illumina sequence data," *Bioinformatics*, 30(15): 2114-2120 (2014).
Brown et al., "Neo-antigens predicted by tumor genome meta-analysis correlate with increased patient survival," *Genome Research*, 24: 743-750 (2014).
Cerami et al., "The cBio Cancer Genomics Portal: An Open Platform for Exploring Multidimensional Cancer Genomics Data," *Cancer Discovery*, 2(5): 401-404 (2012).
Chen et al., "Genome-wide CRISPR screen in a mouse model of tumor growth and metastasis," *Cell*, 160(6): 1246-1260 (2015).
Cheng et al., "Multiplexed activation of endogenous genes by CRISPR-on, an RNA-guided transcriptional activator system," *Cell Research*, 23: 1163-1171 (2013).

(Continued)

*Primary Examiner* — Juliet C Switzer
*Assistant Examiner* — Wahwah T Johnson
(74) *Attorney, Agent, or Firm* — Leydig, Voit & Mayer

(57) ABSTRACT

Disclosed are methods of selecting a therapy for a cancer patient and methods of treating cancer in the patient. The methods comprise detecting a mutation in one or more genes in a cancer cell from the patient, wherein the one or more genes is selected from the group consisting of PTCD2, TWF1, DEFB134, BBS1, SOX10, APLNR, CD58, COL17A1, CRKL, hsa-mir-101-2, hsa-mir-548s, MAD2L1, MLANA, PSMB5, RNPS1, RPL10A, RPL23, SRP54, TAF3, TAP1, TAP2, TAPBP, TBXAS1, GMIP, OTOA, LAIR1, CLEC1, GPSM3, TRAF1, JAK2, TAPBPL, ICAM1, LILRA1, LILRA3, STAT1, and HLA-F. Also disclosed are methods of screening for one or more genes, the mutation of which confers resistance to T cell-mediated cytolytic activity.

6 Claims, 41 Drawing Sheets
Specification includes a Sequence Listing.

(56) References Cited

OTHER PUBLICATIONS

Egen et al., "CTLA-4: new insights into its biological function and use in tumor immunotherapy," *Nat. Immunol.*, 3(7): 611-618 (2002).
Gao et al., "Loss of IFN-γ Pathway Genes in Tumor Cells as a Mechanism of Resistance to Anti-CTLA-4 Therapy," *Cell*, 167: 397-404 (2016).
Gao et al., "Integrative Analysis of Complex Cancer Genomics and Clinical Profiles Using the cBioPortal," *Sci. Signal.*, 6(269): pl1 (2013), 34 pp.
Hart et al., "High-Resolution CRISPR Screens Reveal Fitness Genes and Genotype-Specific Cancer Liabilities," *Cell*, 163: 1515-1526 (2015).
International Bureau of WIPO, International Preliminary Report on Patentability in International Patent Application No. PCT/US2017/060304, dated May 16, 2019.
International Bureau of WIPO, International Search Report in International Patent Application No. PCT/US2017/060304, dated Feb. 5, 2018.
International Bureau of WIPO, Written Opinion in International Patent Application No. PCT/US2017/060304, dated Feb. 5, 2018.
Johnson et al., "Gene Transfer of Tumor-Reactive TCR Confers Both High Avidity and Tumor Reactivity to Nonreactive Peripheral Blood Mononuclear Cells and Tumor-Infiltrating Lymphocytes," *J. Immunol.*, 177(9): 6548-6559 (2006).
Kidoya et al., "The apelin/APJ system induces maturation of the tumor vasculature and improves the efficiency of immune therapy," *Oncogene*, 31: 3254-3264 (2012).
Kvistborg et al., "Anti-CTLA-4 therapy broadens the melanoma-reactive CD8+ T cell response," *Science Translational Medicine*, 6(254): 254ra128 (2014), 10 pp.
Langmead, "Searching for SNPs with Cloud Computing," *Genome Biol.*, 10(11): 1-10 (2009).
Langmead, "Ultrafast and memory-efficient alignment of short DNA sequences to the human genome," *Genome Biol.*, 10(3): 1-10 (2009).
Langmead et al., "Fast gapped-read alignment with Bowtie 2," *Nat. Methods*, 9(4): 357-359 (2012).
Martin, "Cutadapt removes adapter sequences from high-throughput sequencing reads," *EMBnet.journal*, 17(1): 10-12 (2011).
McGranahan et al., "Clonal neoantigens elicit T cell immunoreactivity and sensitivity to immune checkpoint blockade," *Science*, 351(6280): 1463-1469 (2016).
Neefjes et al., "Towards a systems understanding of MHC class I and MHC class II antigen presentation," *Nat. Rev. Immunol.*, 11: 823-36 (2011).
O'Carroll et al., "The apelin receptor APJ: journey from an orphan to a multifaceted regulator of homeostasis," *Journal of Endocrinology*, 219(1): R13-R35 (2013).
Patel et al., "Identification of essential genes for cancer immunotherapy," *Nature*, 548: 537-542 (2017).
Patel, "A Genome-scale CRISPR screen to identify essential genes for the effector function of cytotoxic T lymphocytes," Dissertation, Georgetown University, 110 pages (published 2017).
Robbins et al., "Single and Dual Amino Acid Substitutions in TCR CDRs Can Enhance Antigen-Specific T Cell Functions," *J. Immunol.*, 180(9): 6116-6131 (2008).
Rooney et al., "Molecular and genetic properties of tumors associated with local immune cytolytic activity," *Cell*, 160(1-2): 48-61 (2015).
Spiotto, "Bystander elimination of antigen loss variants in established tumors," *Nature Medicine*, 10(3): 294-298 (2004).
Van Allen et al., "Genomic correlates of response to CTLA-4 blockade in metastatic melanoma," *Science*, 350(6257): 207-211 (2015).
Wan et al., "TCGA2STAT: simple TCGA data access for integrated statistical analysis in R," *Bioinformatics*, 32(6): 952-954 (2016).
Wang et al., "Genetic Screens in Human Cells Using the CRISPR-Cas9 System," *Science*, 343: 80-84 (2014).
Yang et al., "Apelin/APJ system and cancer," *Clinica Chimica Acta*, 457: 112-116 (2016).
Zaretsky et al., "Mutations Associated with Acquired Resistance to PD-1 Blockade in Melanoma," *The New England Journal of Medicine*, 375(9): 819-829 (2016).

\* cited by examiner

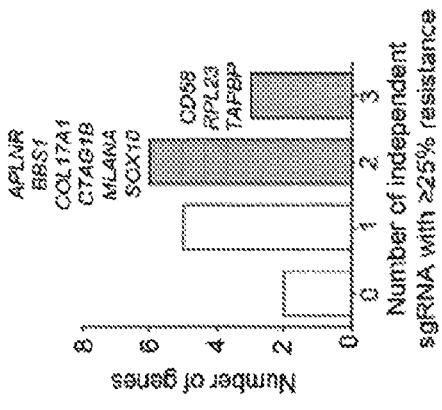
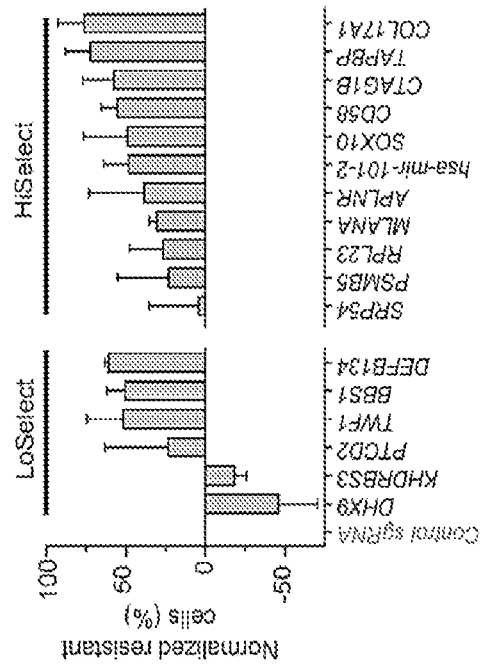
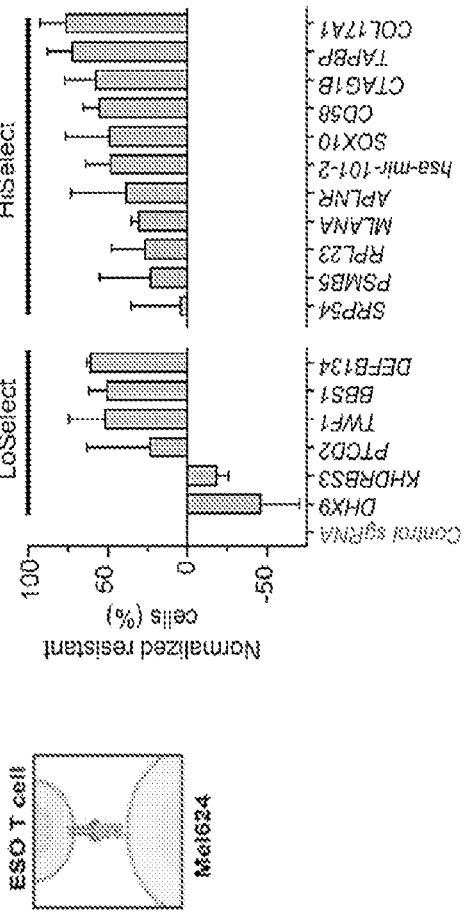
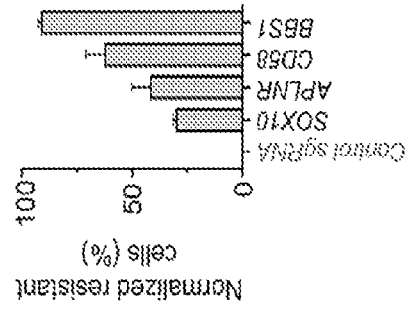
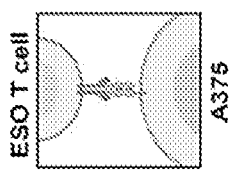
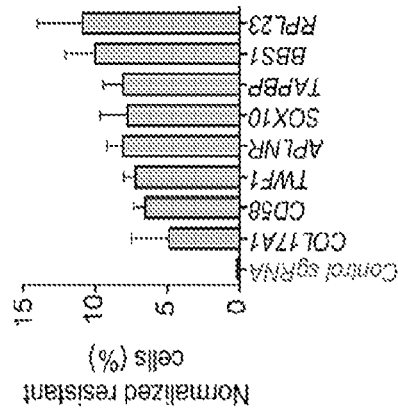
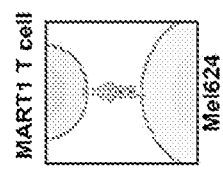

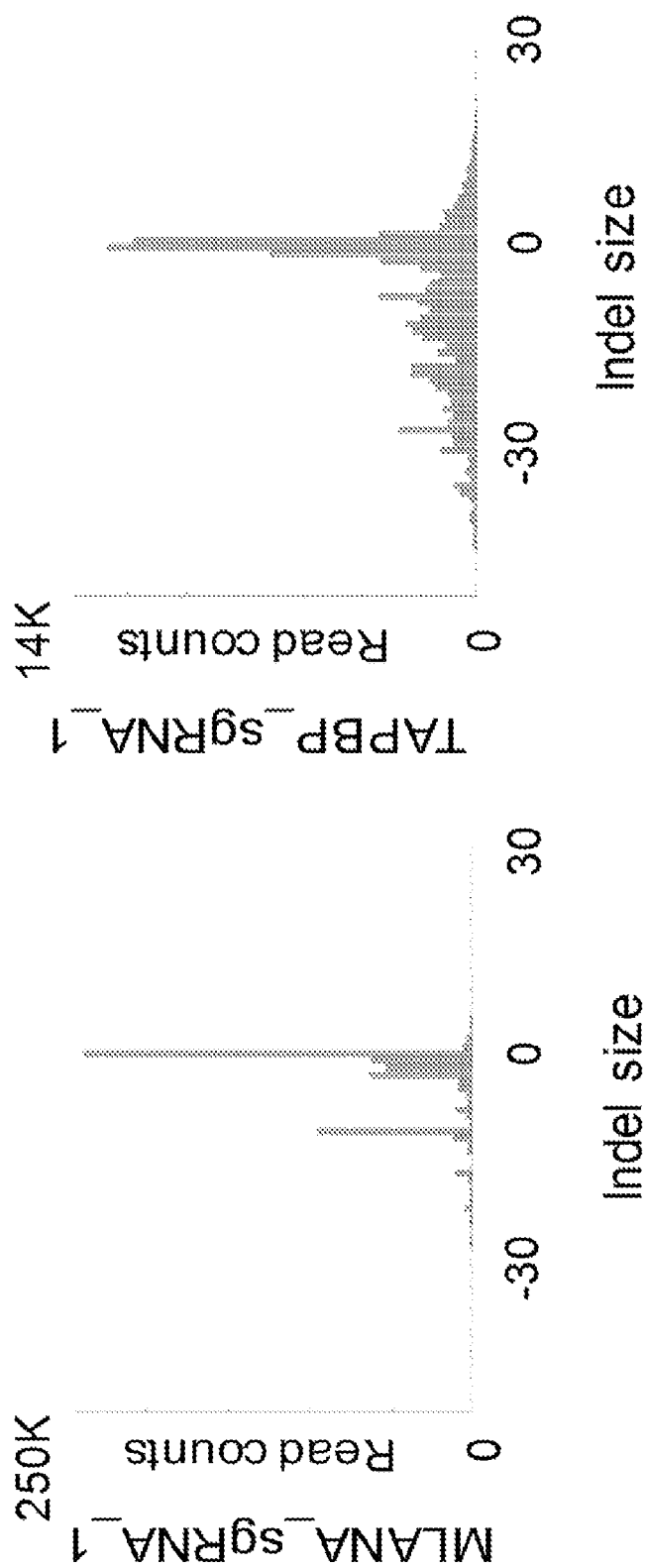

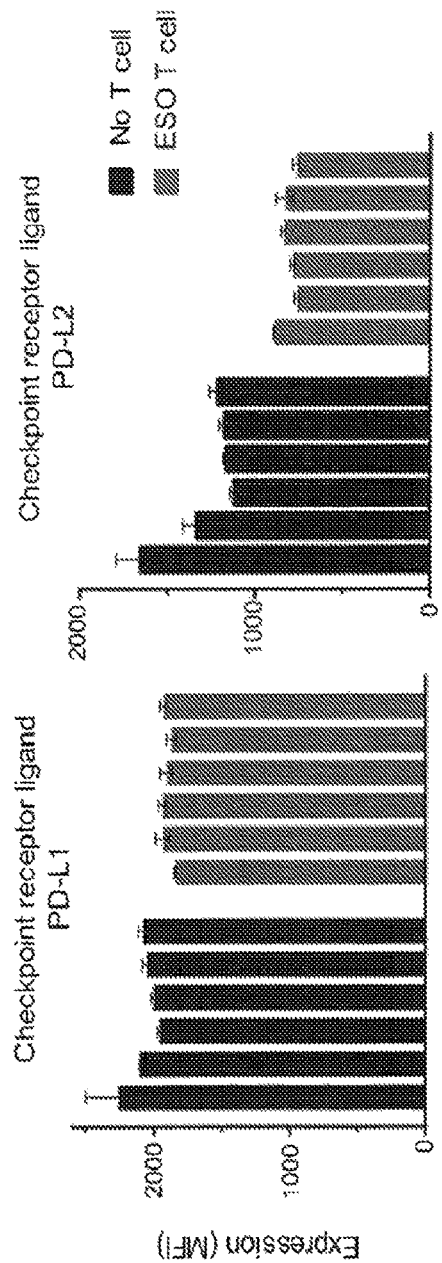
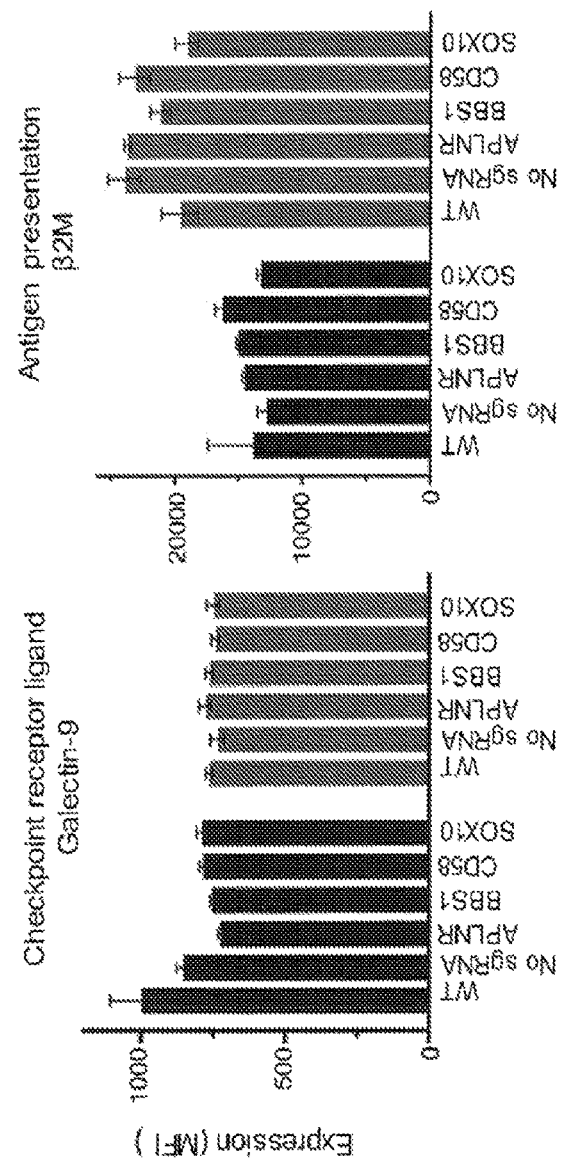
Fig. 14A, Fig. 14B, Fig. 14C, Fig. 14D

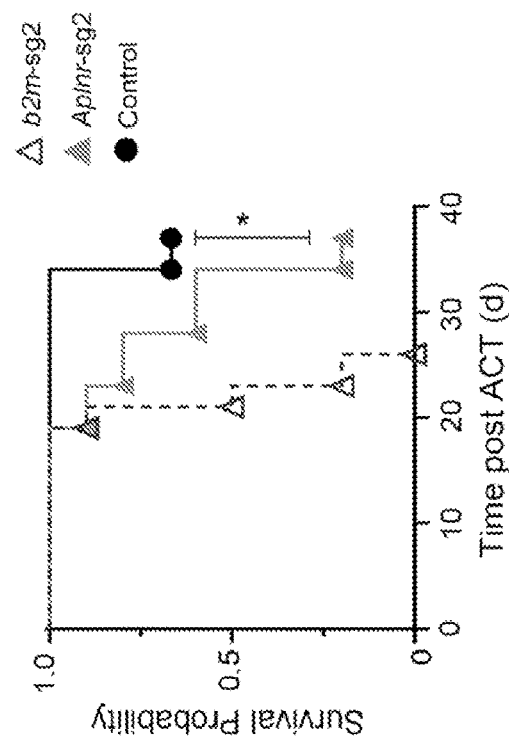
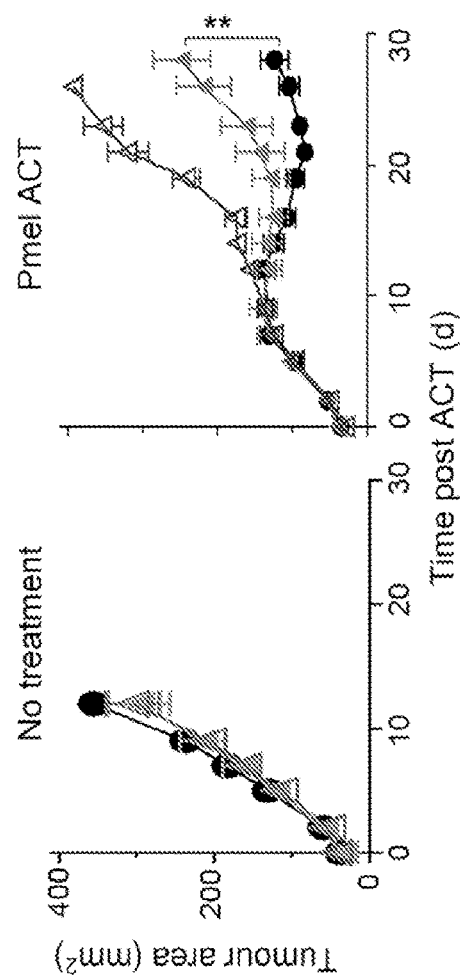
Fig. 22A Fig. 22B Fig. 22C

METHODS FOR SELECTING THERAPY FOR A CANCER PATIENT

CROSS-REFERENCE TO RELATED APPLICATIONS

This patent application is a U.S. National Phase Patent Application of copending International Patent Application No. PCT/US2017/060304, filed Nov. 7, 2017, which claims the benefit of U.S. Provisional Patent Application No. 62/418,461, filed Nov. 7, 2016, both of which are hereby incorporated by reference in their entireties herein.

STATEMENT REGARDING FEDERALLY SPONSORED RESEARCH AND DEVELOPMENT

This invention was made with Government support under project number ZIABC010763-12 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 18,198 Byte ASCII (Text) file named "742287_ST25.txt" created May 2, 2019.

BACKGROUND OF THE INVENTION

Somatic gene mutations in cancer may influence anticancer immunity. For example, somatic gene mutations in cancer cells may give rise to neoantigens capable of eliciting T cell mediated cytolysis of the cancer cells. Conversely, somatic gene mutations in cancer cells may also contribute to the ability of the cancer cells to evade T cell mediated cytolysis. Evasion of T cell mediated cytolysis by the cancer cells may impair the effectiveness of immunotherapies. Despite advancements in the immunotherapeutic treatment of cancer, there exists a need for improved methods of identifying genetic mutations which may impair T cell mediated cytolysis of cancer cells.

BRIEF SUMMARY OF THE INVENTION

An embodiment of the invention provides a method of selecting a therapy for a cancer patient, the method comprising: detecting a mutation in one or more genes in a cancer cell from the patient which is not present in a noncancerous cell, wherein the mutation decreases one or both of expression and activity of polypeptide(s) encoded by the one or more genes; and wherein the one or more genes is selected from the group consisting of PTCD2, TWF1, DEFB134, BBS1, SOX10, APLNR, CD58, COL17A1, CRKL, hsa-mir-101-2, hsa-mir-548s, MAD2L1, MLANA, PSMB5, RNPS1, RPL10A, RPL23, SRP54, TAF3, TAP1, TAP2, TAPBP, TBXAS1, GMIP, OTOA, LAIR1, CLEC1, GPSM3, TRAF1, JAK2, TAPBPL, ICAM1, LILRA1, LILRA3, STAT1, and HLA-F; selecting the patient for a therapy which is not a T cell therapy when the mutation in one or more genes is present in the cancer cell; and selecting the patient for a T cell therapy when the mutation in one or more genes is not present in the cancer cell.

An embodiment of the invention provides a method of selecting a therapy for a cancer patient, the method comprising: detecting a mutation in one or more polypeptides in a cancer cell from the patient which is not present in a noncancerous cell, wherein the mutation decreases activity of the polypeptide; and wherein the one or more polypeptides is encoded by a gene selected from the group consisting of PTCD2, TWF1, DEFB134, BBS1, SOX10, APLNR, CD58, COL17A1, CRKL, hsa-mir-101-2, hsa-mir-548s, MAD2L1, MLANA, PSMB5, RNPS1, RPL10A, RPL23, SRP54, TAF3, TAP1, TAP2, TAPBP, TBXAS1, GMIP, OTOA, LAIR1, CLEC1, GPSM3, TRAF1, JAK2, TAPBPL, ICAM1, LILRA1, LILRA3, STAT1, and HLA-F; selecting the patient for a therapy which is not a T cell therapy when the mutation is present in the cancer cell; and selecting the patient for a T cell therapy when the mutation is not present in the cancer cell.

Still another embodiment of the invention provides a method of selecting a therapy for a cancer patient, the method comprising: measuring a level of one or both of (i) mRNA and (ii) polypeptide expressed from one or more genes in a cancer cell from the patient, wherein the one or more genes is selected from the group consisting of PTCD2, TWF1, DEFB134, BBS1, SOX10, APLNR, CD58, COL17A1, CRKL, hsa-mir-101-2, hsa-mir-548s, MAD2L1, MLANA, PSMB5, RNPS1, RPL10A, RPL23, SRP54, TAF3, TAP1, TAP2, TAPBP, TBXAS1, GMIP, OTOA, LAIR1, CLEC1, GPSM3, TRAF1, JAK2, TAPBPL, ICAM1, LILRA1, LILRA3, STAT1, and HLA-F; measuring the level of one or both of (i) mRNA and (ii) polypeptide expressed from the same one or more genes in a noncancerous cell; comparing the level of one or both of (i) mRNA and (ii) polypeptide measured in the cancer cell with the level of one or both of (i) mRNA and (ii) polypeptide, respectively, measured in the noncancerous cell; selecting the patient for a therapy which is not a T cell therapy when the level of one or both of (i) mRNA and (ii) polypeptide measured in the cancer cell is decreased as compared to the level of one or both of (i) mRNA and (ii) polypeptide, respectively, measured in the noncancerous cell; and selecting the patient for a T cell therapy when the level of one or both of (i) mRNA and (ii) polypeptide measured in the cancer cell is not decreased as compared to the level of one or both of (i) mRNA and (ii) polypeptide, respectively, measured in the noncancerous cell.

Still another embodiment of the invention provides a method of screening for one or more genes, the mutation of which confers resistance to T cell-mediated cytolytic activity, the method comprising: introducing a nucleic acid encoding a Cas endonuclease and a nucleic acid encoding a single guide RNA (sgRNA) molecule into a target cell, wherein the sgRNA hybridizes to a test gene in the target cell, forming a complex between the sgRNA and Cas endonuclease so that the Cas endonuclease introduces a double strand break in the test gene; deleting all or a portion of the test gene to decrease expression of the test gene; co-culturing the target cell having decreased expression of the test gene with an effector cell; co-culturing a negative control cell with the effector cell, wherein the negative control cell is identical to the target cell except that it does not comprise the nucleic acid encoding a Cas endonuclease and the nucleic acid encoding a single guide RNA (sgRNA) molecule and does not have decreased expression of the test gene; measuring a level of lysis of the target cell by the effector cell; measuring a level of lysis of the negative control cell by the effector cell; and comparing the level of lysis of the target cell to the level of lysis of the negative control cell; wherein a decrease in the level of lysis of the target cell as compared to the level of lysis of the negative control cell indicates that mutation of the test gene confers resistance to T cell-mediated cytolytic activity to the target cell; and wherein a lack of a decrease in the level of lysis of the target cell as compared to the level of lysis of the negative control cell indicates that mutation of the test gene does not confer resistance to T cell-mediated cytolytic activity to the target cell.

Further embodiments of the invention provide related methods of selecting a therapy for a cancer patient and treating cancer in the patient.

BRIEF DESCRIPTION OF THE SEVERAL VIEWS OF THE DRAWING(S)

Figure 1A:
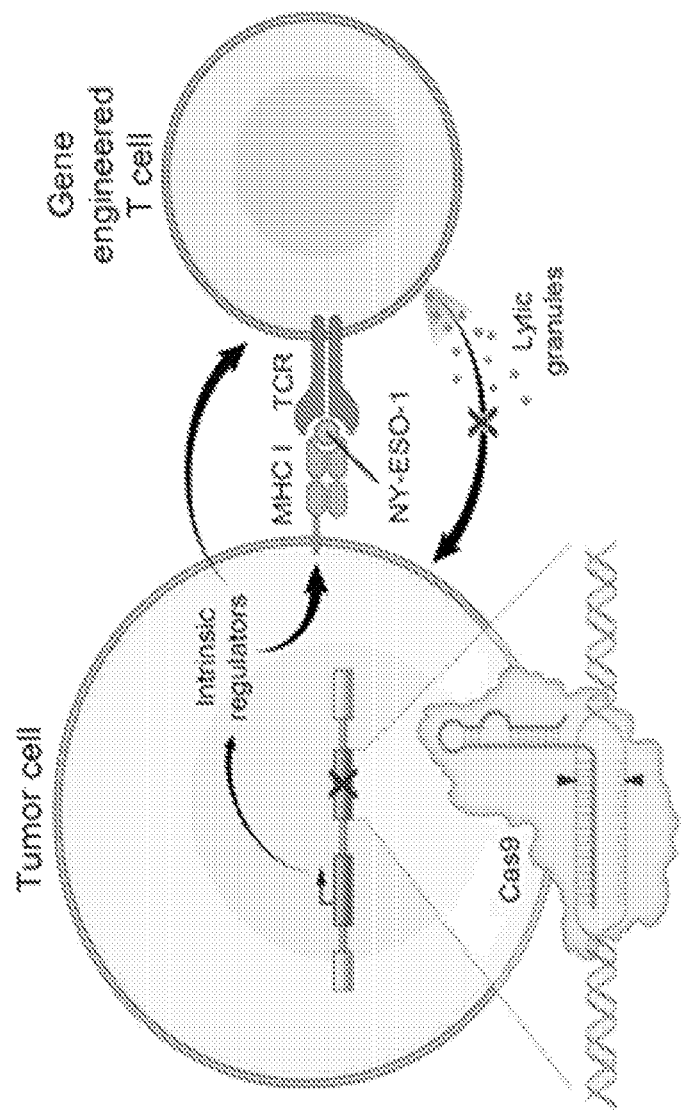
FIG. 1A is a schematic representation of a 2CT CRISPR-Cas9 assay system to identify loss-of-function resistant genes against T cell-mediated target cell lysis.
Figure 1C:
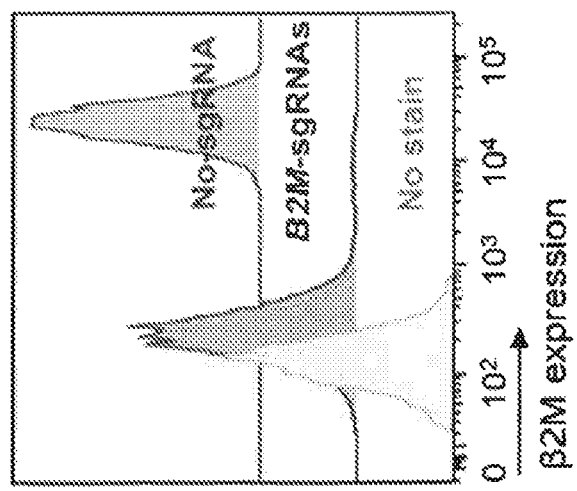
FIG. 1C is a representative FACS plot showing highly efficient perturbation of B2M in Mel624 cells using human GeCKOv2 lentiviral vector system.
Figure 1B:
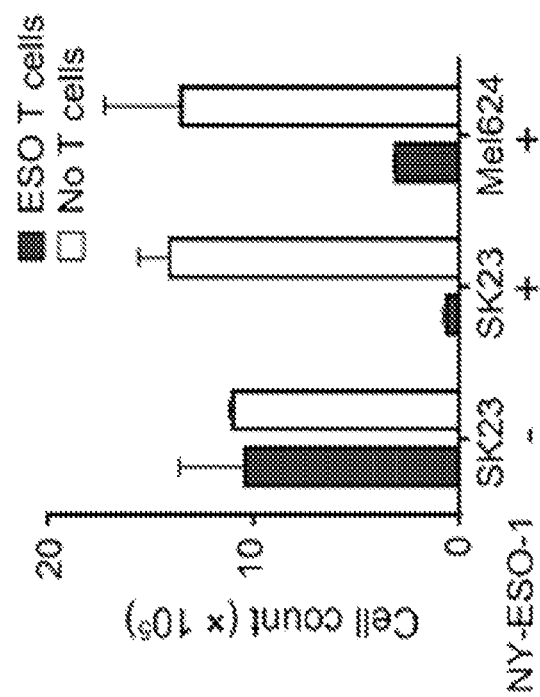
FIG. 1B is a graph showing the NY-ESO-1 antigen specific lysis of melanoma cells after 24 h of co-culture of engineered ESO T cells (shaded bars) or no T cells (control) (unshaded bars) with NY-ESO-1⁻SK23, NY-ESO-1⁺SK23 and NY-ESO-1⁺Mel624 cells (n=3 replicates) at E:T ratio of 1.
Figure 1E:
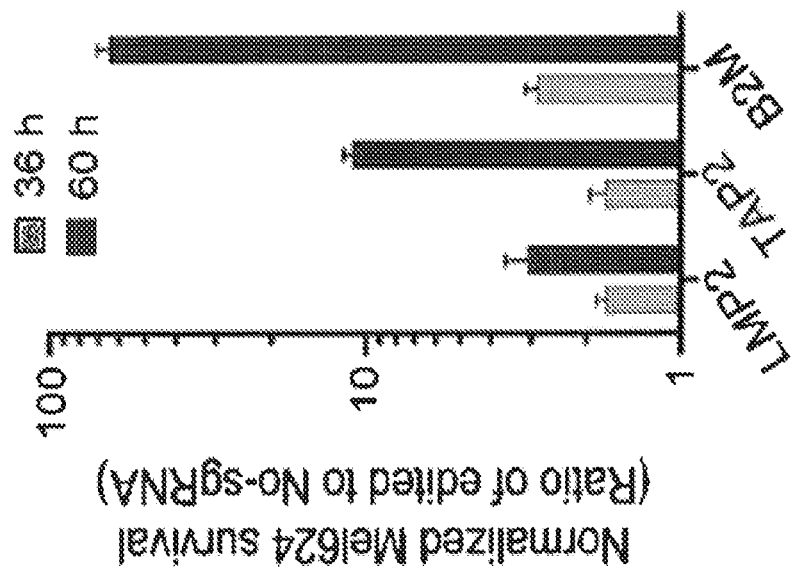
Figure 1D:
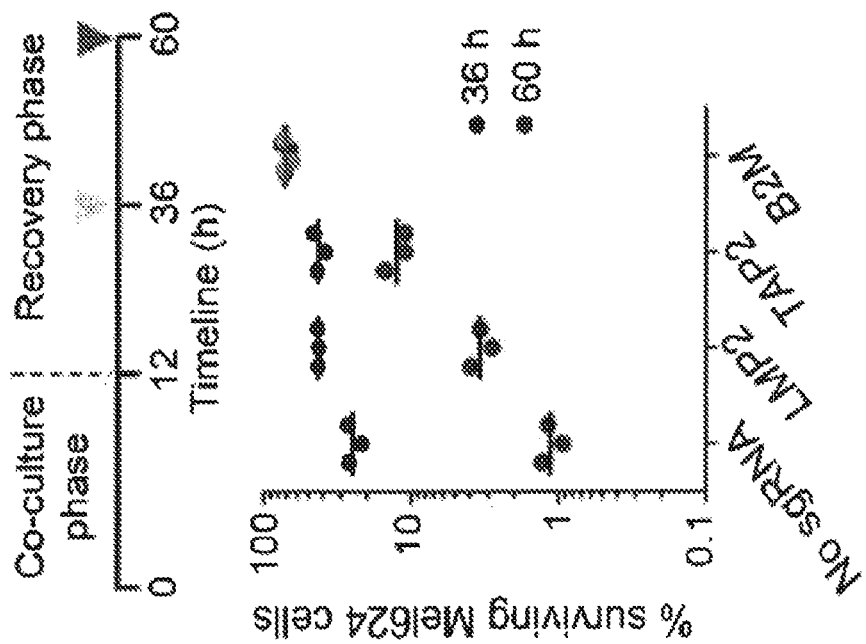

FIG. 1D includes a timeline showing 12 h of co-culture of ESO T cells with individual gene edited Mel624 cells at E:T ratio of 0.5. Live cell survival (%) was calculated from control cells unexposed to T cell selection. Each dot in the plot represents independent gene-specific CRISPR lentivirus infection replicate (n=3).

FIG. 1E is a graph showing the improvement in CRISPR edited cell yields at 60 h timepoint compared to 36 h after 2CT assay. Error bar denotes mean±S.E.M.

Figure 2A:
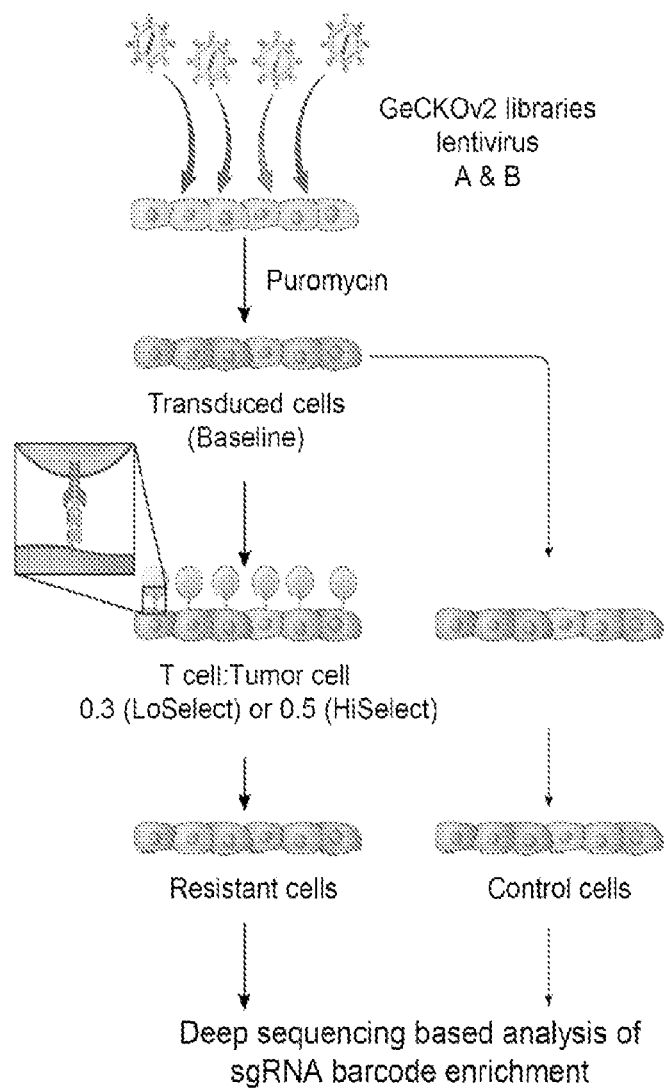

FIG. 2A is a schematic showing the design of genome-wide 2CT CRISPR screen to identify loss-of-function genes conferring resistance to T cell-mediated target cell lysis. Mel624 cells transduced with GeCKOv2 libraries were selected with puromycin for 5-7 days. Screens with T-cell based selection at E:T of 0.3 are termed as 'LoSelect' screens and at E:T of 0.5 is termed as 'HiSelect' screens.

Figure 2B:
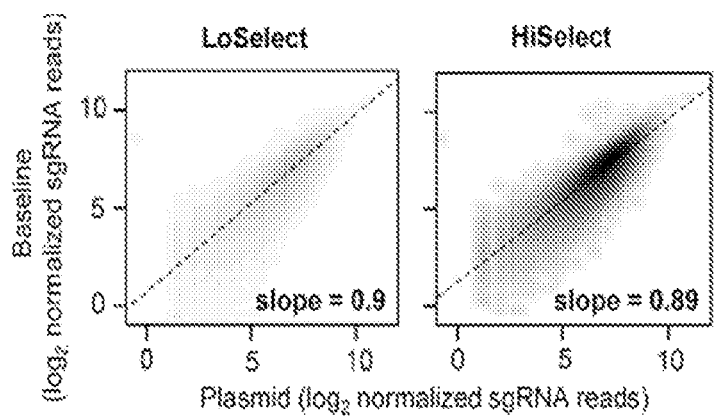

FIG. 2B shows a comparison of sgRNA representation between the plasmid pools to early timepoint transduced cells post puromycin selection.

Figure 2C:
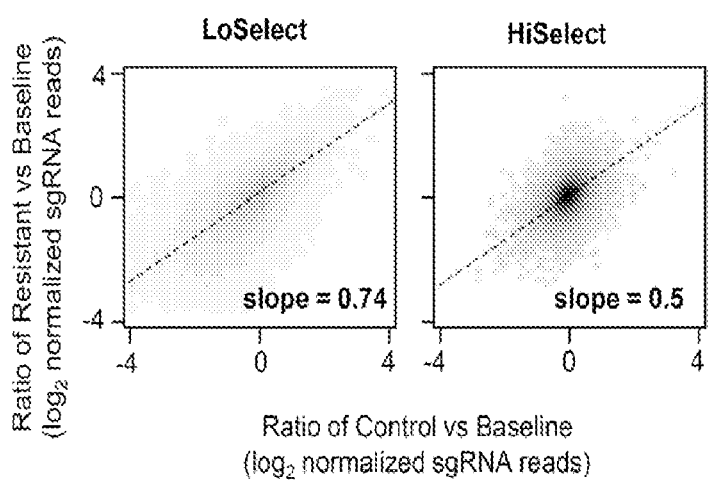

FIG. 2C is a scatterplot showing the effect of LoSelect and HiSelect co-culture conditions on the global distribution of sgRNAs.

Figure 2D:
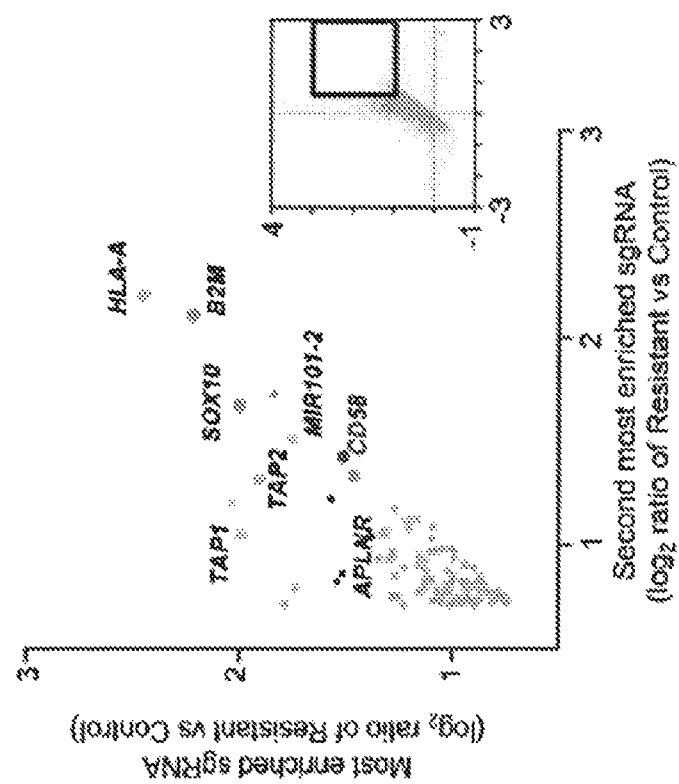

FIG. 2D is a scatterplot showing the enrichment of the most versus the second most enriched sgRNAs after T cell-based selection. The top 100 genes were magnified from the inset showing all the sgRNAs pooled from HiSelect screens using both A and B libraries.

Figure 2E:
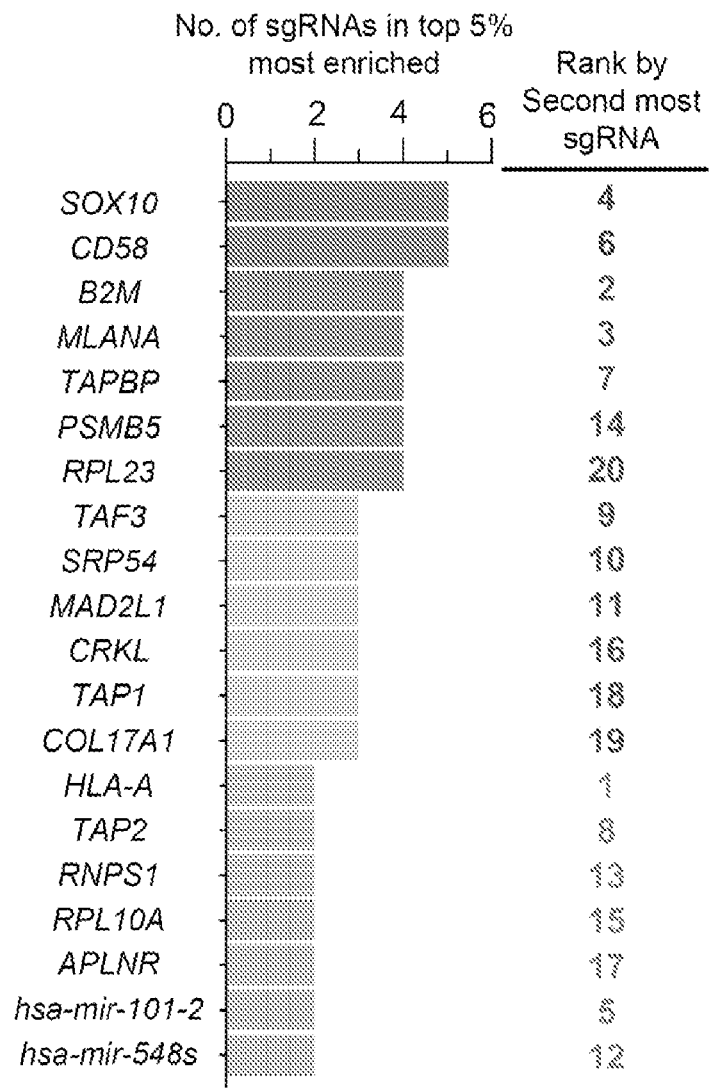

FIG. 2E is a graph showing the consistency of multiple sgRNA enrichment for top 20 ranked genes by second-best score in HiSelect screens. Frequency of unique sgRNAs targeting each gene in top 5% of most abundant sgRNAs is plotted.

FIG. 3A is a schematic illustrating a Mel624 cell and a ESO T cell.

FIG. 3B is a bar-plot showing the average survival of individually edited cells for 16 genes and 1 miR targeted with 2-4 different sgRNAs subjected to 2CT CRISPR assay at E:T ratio of 0.5 using Mel624 cells and ESO T cells. Data shown as an average of tested 2-4 sgRNAs per gene. Error bar denotes mean±S.E.M.

FIG. 3C is a bar-plot showing the number of genes validated in arrayed screen with 0, 1, 2 or 3 sgRNAs showing significant resistance phenotype for that gene. Genes with >2 sgRNAs displaying resistance against T cell-mediated lysis are listed above the bar plot.

FIG. 3D is a schematic illustrating a Mel624 cell and a MART1 T cell.

FIG. 3E is a bar-plot of the LoF genes showing resistance against high avidity MART1 T cell-mediated lysis. Mel624 cells subjected to 2CT CRISPR assay using MART1 T cells from healthy donors at E:T ratio of 1. All listed genes are significantly resistant, P<0.05 compared to non-target control sgRNA. Data shown as an average of tested 2-4 sgRNAs per gene. Error bar denotes mean±S.E.M.

FIG. 3F is a schematic illustrating a ESO T cell and a A375 cell.

FIG. 3G is a bar-plot showing the genes validated with another melanoma cell line A375 that expresses NY-ESO-1 antigen in HLA-A2 restricted fashion. All listed genes are significantly resistant, P<0.05 compared to non-target control sgRNA. n=3 replicates. Data shown as an average of tested 2-4 sgRNAs per gene. Error bar denotes mean±S.E.M.

Figures 4A, 4B:
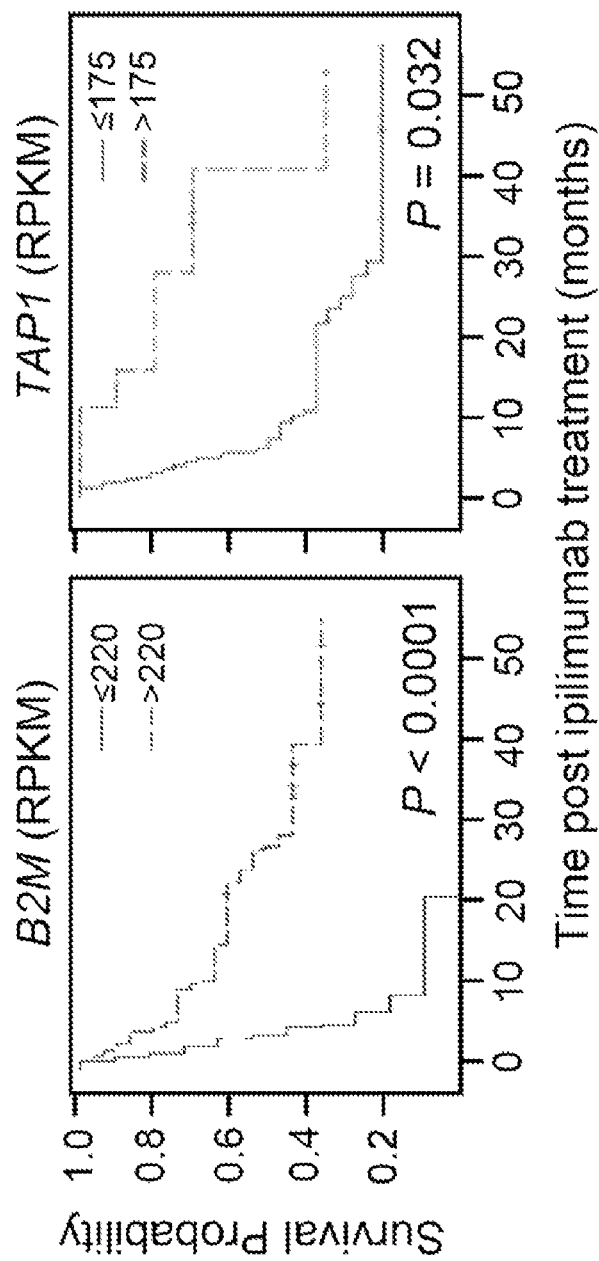

FIG. 4A and FIG. 4B show that the intratumoral expression (RPKM) of the antigen presentation genes, B2M (A) and TAP1 (B), are associated with survival of melanoma patients treated with T cell-based immunotherapy of CTLA4 blockade with ipilimumab. Based on Kaplan-Meier survival analysis for each gene where patients were initially grouped according to quartile values of gene expression, patients were split into two groups with differing survival outcomes by indicated RPKM values for each gene. The log-rank p-values shown are after adjustment for the evaluations done on the quartile groupings to arrive at the final, significant split presented.

Figure 4C:
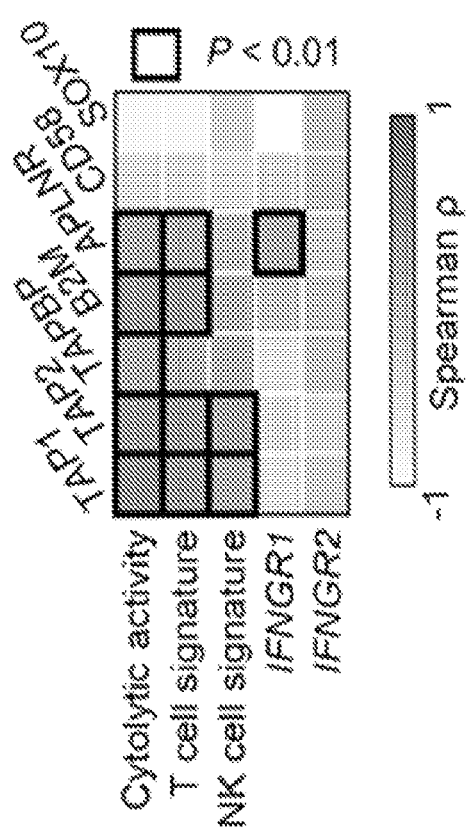

FIG. 4C shows that the expression of cytolytic genes (geometric mean of RPKM values of PRE1 and GZMA), T cell signature genes (CD3E, CD8A and CD4) and natural killer cells (NCAM1 and NCR1) correlates with expression of antigen presentation pathway genes functionally validated with the 2CT CRISPR assay. APLNR expression shows a unique, weak to moderately strong correlation similar to B2M with cytolytic activity (p=0.43, P=0.005) and T cell markers (p=0.48, P=0.001) while not with NK cell markers (p=0.22, P=0.167). n=42 melanoma patient biopsies.

Figure 4D:
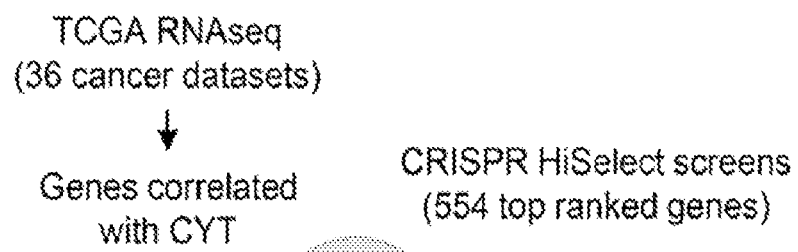
Figure 4E:
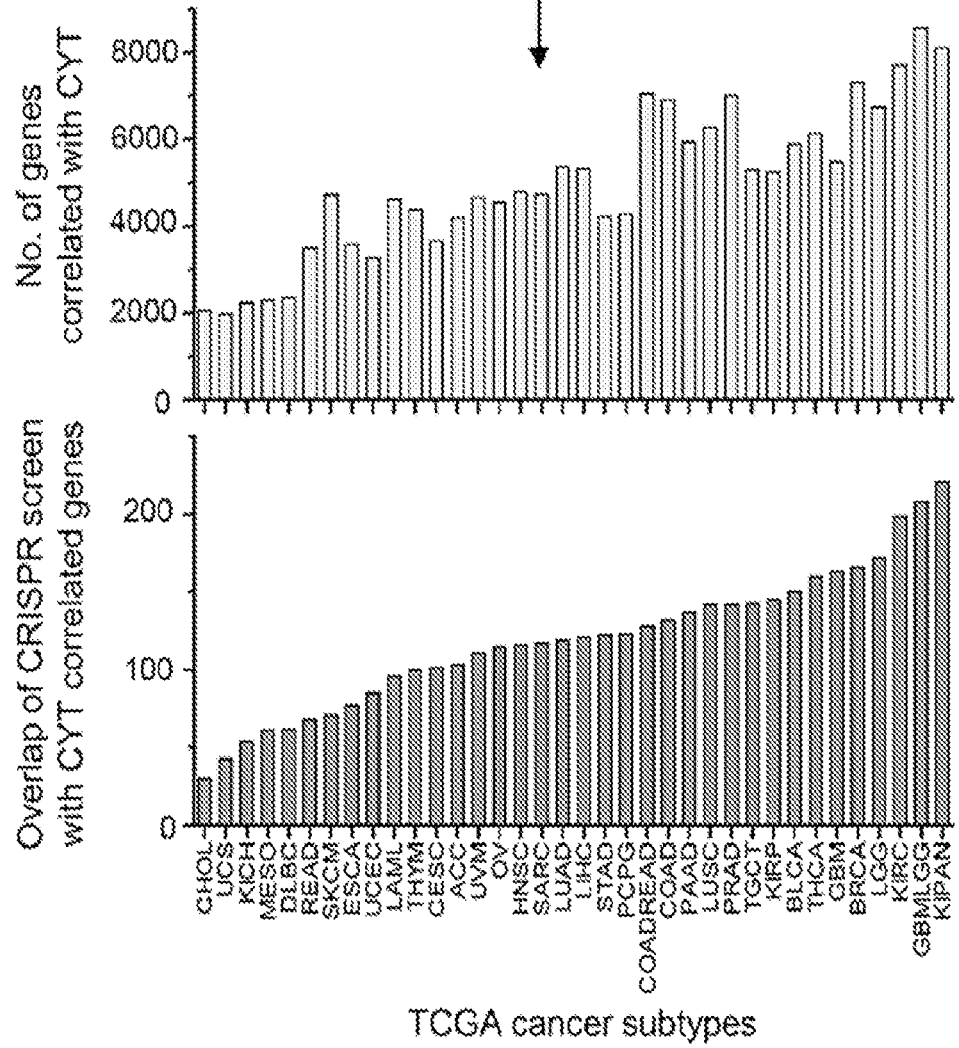

FIGS. 4D and 4E show the gene expression from RNAseq data for 36 human cancers obtained from TCGA database. Genes found positively correlated with cytolytic activity (P<0.05) were intersected with CRISPR genes from the HiSelect screen to yield gene lists for each cancer type shown in FIG. 4E. The number of genes correlated with CYT (D) and the overlap of CRISPR screen with CYT correlated genes (E) are shown.

Figure 4F:
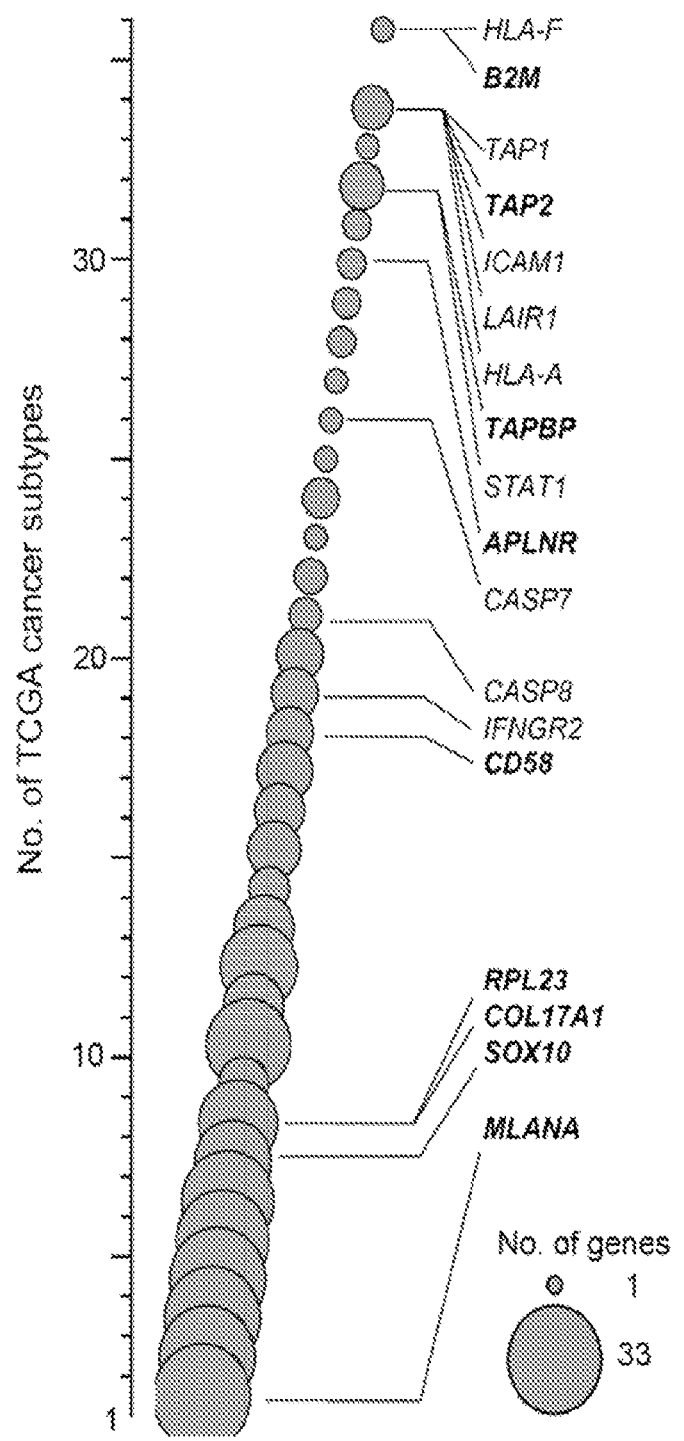

FIG. 4F is a bubble plot depicting the number of overlapping genes from FIGS. 4D and 4E correlated across multiple cancers. Previously known genes B2M, CASP7 and CASP8, and novel validated genes from CRISPR screen are highlighted according to their correlation to the cytolytic activity in the number of different cancer-types. Size of each bubble represents the number of genes in each dataset.

Figure 5A:
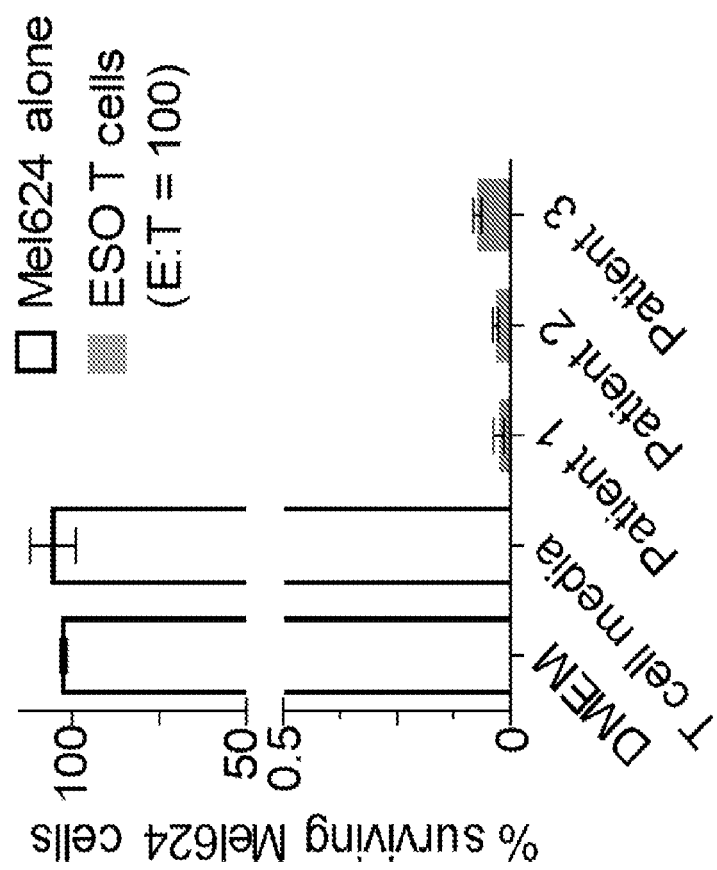

FIG. 5A is a barplot showing the the cytolysis efficiency of T cells upon co-culture of patient ESO T cells with Mel624 cells at an E:T ratio of 100 for 24 hr.

Figure 5B:
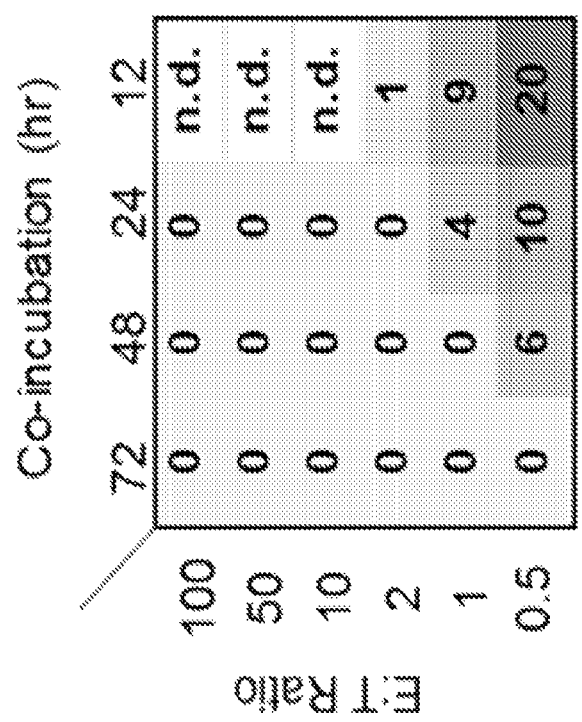

FIG. 5B shows the design of selection pressure exerted by ESO T cells on Mel624 cells at variable timings of co-culture and E:T ratios. Numbers in the grid represent approximate tumor cell survival (%) after co-culture. Data pooled from 3 independent experiments. n=3 replicates for each culture condition.

Figure 5C:
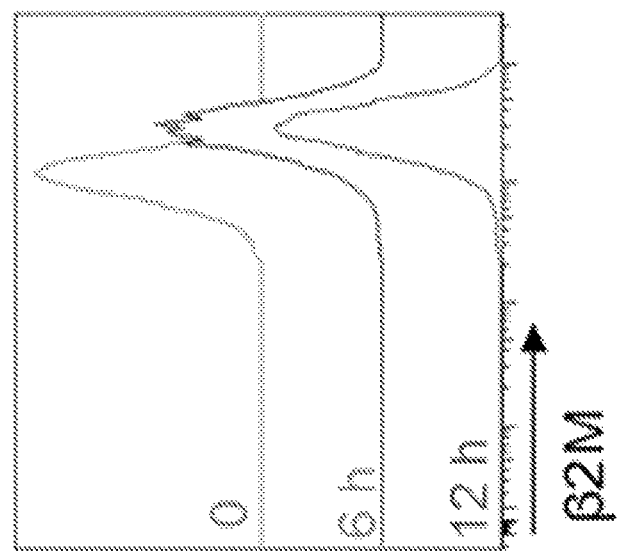

FIG. 5C shows the effect of cell to cell interaction timing on Mel624 cells determined by the upregulation of β2M expression at variable timings after co-culture with ESO T cells at E:T ratio of 0.5. Shown is a representative FACS plot showing distribution of β2M expressing tumor cells.

Figure 5D:
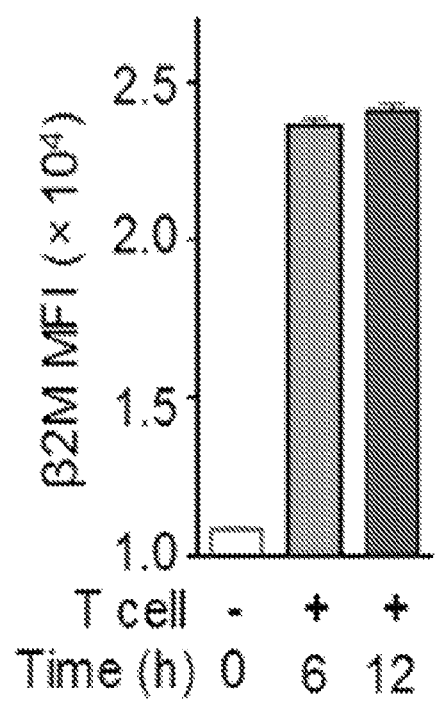

FIG. 5D shows the effect of cell to cell interaction timing on Mel624 cells determined by the upregulation of β2M expression at variable timings after co-culture with ESO T cells at E:T ratio of 0.5. Shown is a bar plot depicting mean fluorescence intensities of n=3 replicates.

Figure 6A:
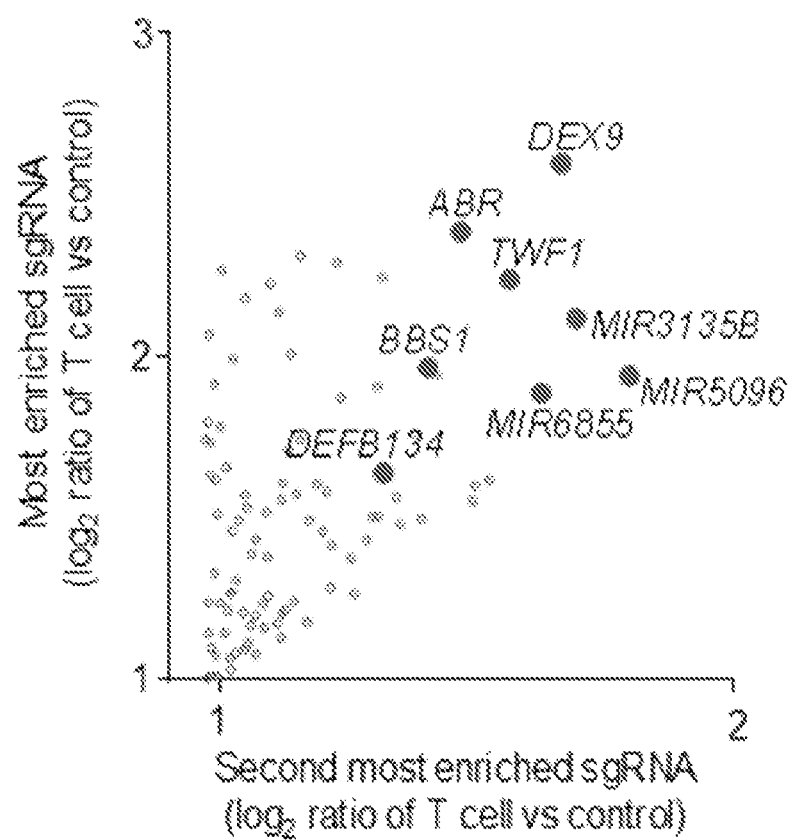

FIG. 6A is a scatterplot showing enrichment of most versus second most enriched sgRNAs after T cell-based selection among the top 100 genes enriched in LoSelect screens.

Figure 6B:
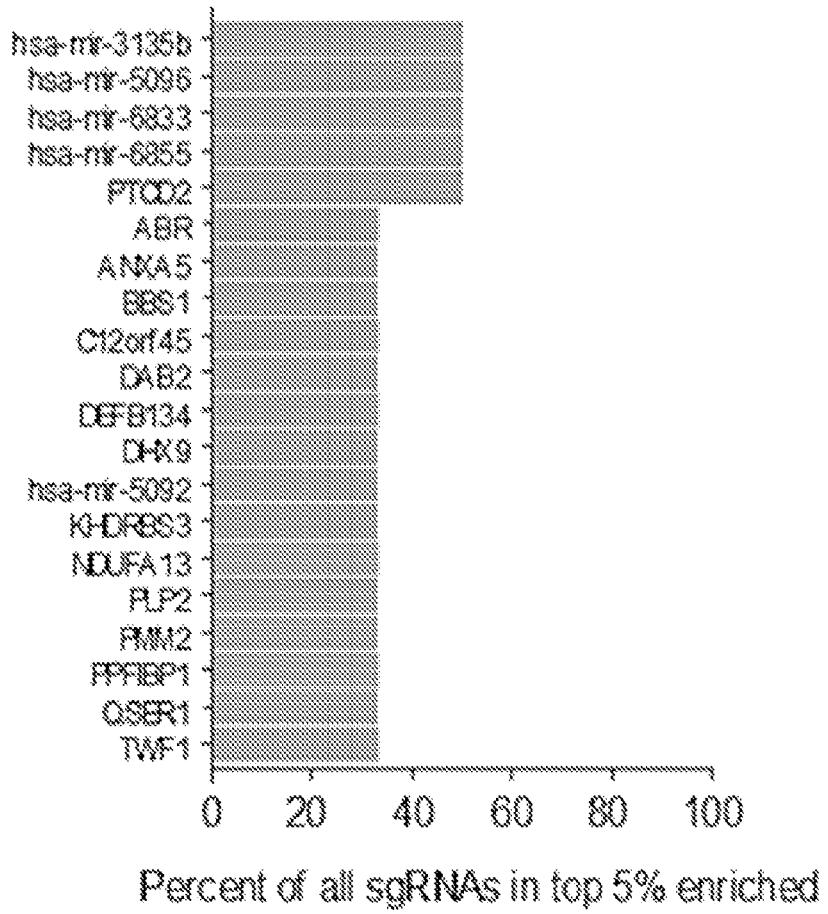

FIG. 6B is a graph showing the consistency of multiple sgRNA enrichments for top 20-ranked genes by the second most enriched sgRNA in LoSelect screens. Frequency of unique sgRNAs targeting each gene in top 5% of all sgRNAs is plotted.

Figure 7A:
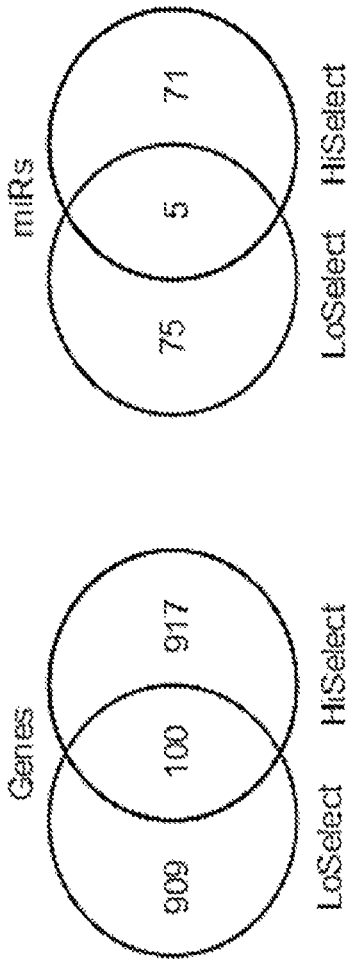

FIG. 7A shows Venn diagrams depicting shared and unique most enriched candidates in top 5% of the second most enriched sgRNA across HiSelect and LoSelect screens.

Figure 7B:
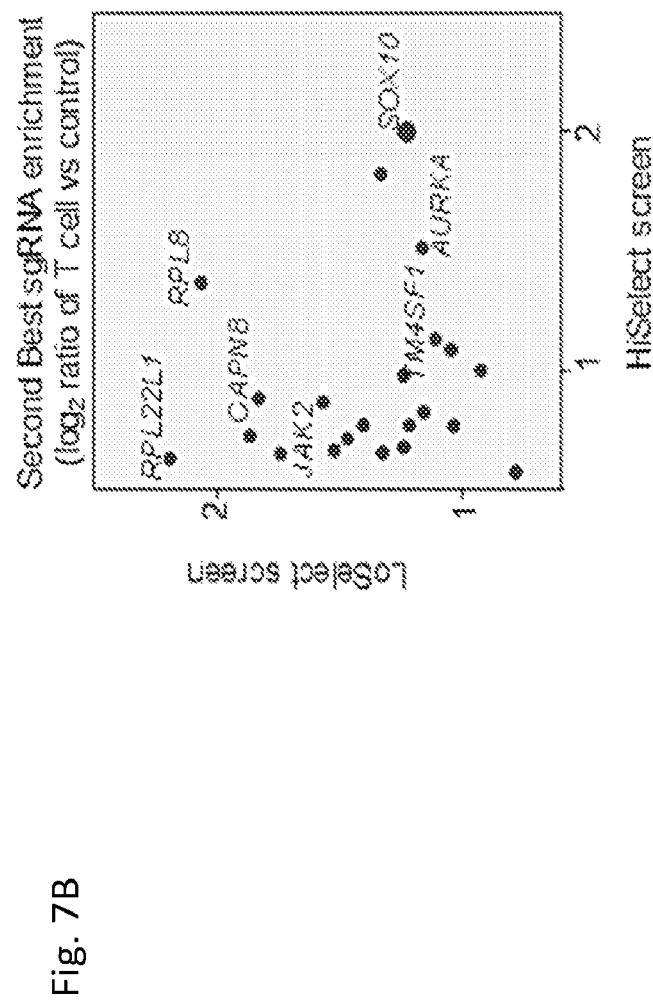

FIG. 7B shows common enriched genes across all screens within the top 500 genes ranked by the second most enriched sgRNA.

Figures 8A, 8B:
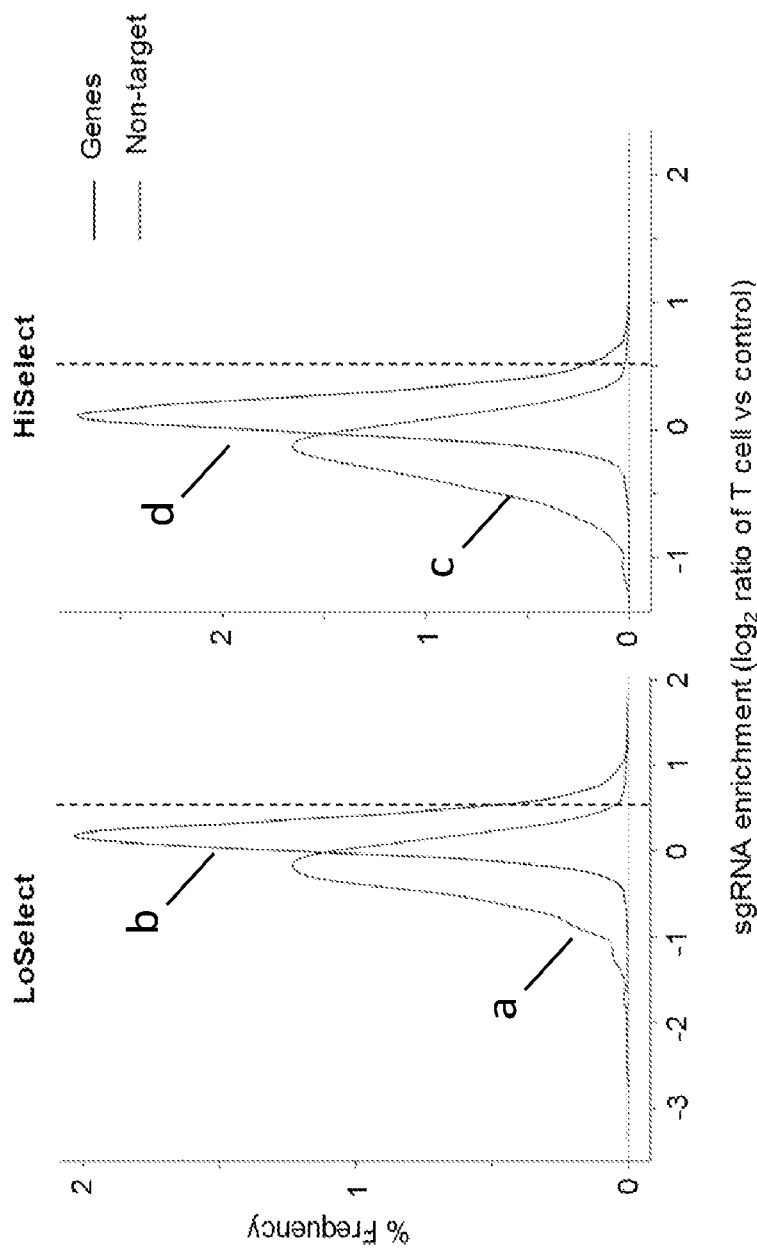

FIGS. 8A and 8B show the distribution of the enriched sgRNA targeting genes (Genes) as compared to non-target controls (Non-target) from both LoSelect (A) and HiSelect (B) screens. Data from library A and library B from each screen were pooled. This distribution was used to determine the false discovery rate (FDR) at 0.5 cutoff, and select genes for the downstream pathway and the TCGA data correlation analyses. Peaks a and c correspond to non-target controls. Peaks b and d correspond to target genes.

Figure 9:
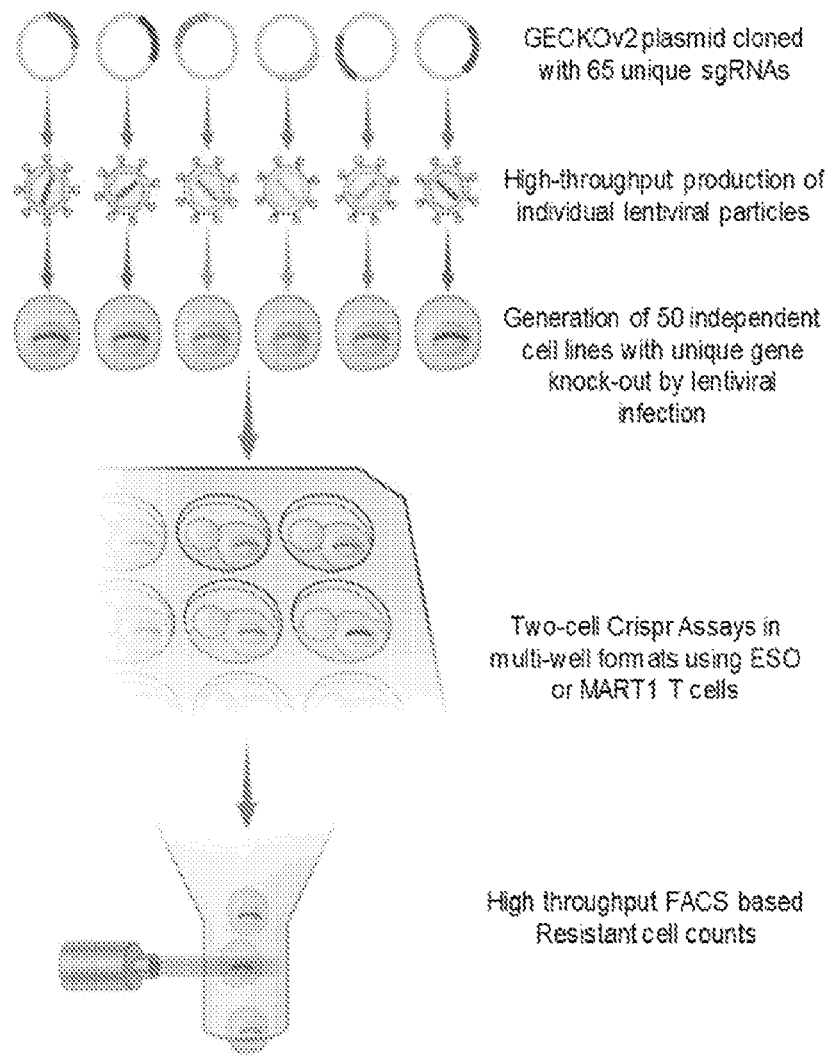

FIG. 9 is a schematic representation of individually-arrayed CRISPR screens used for validation of the highest-ranking genes.

Figure 10A:
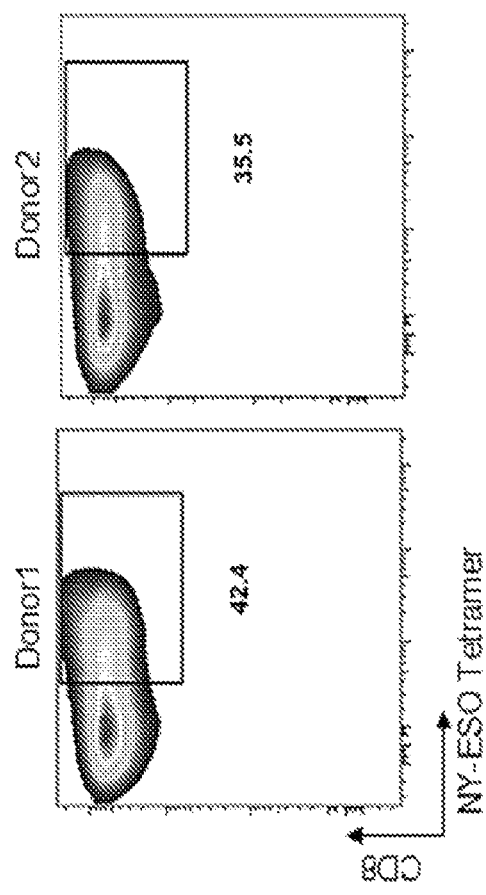
Figure 10B:
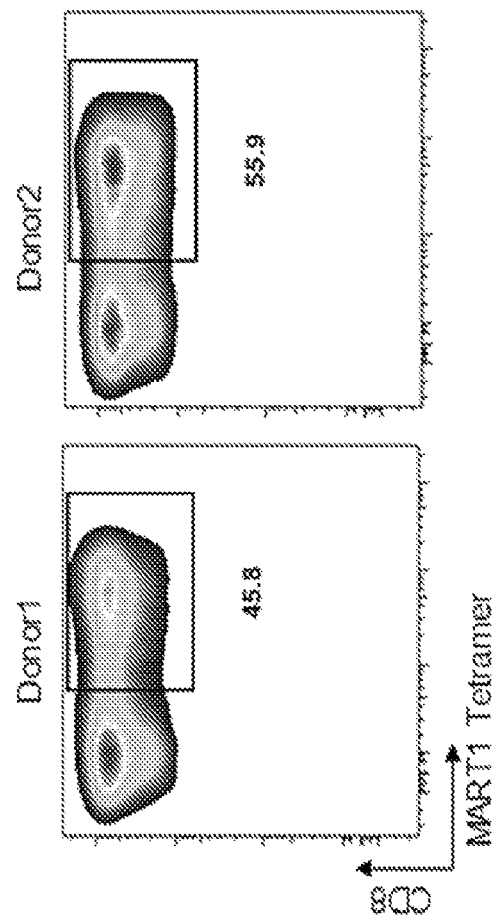

FIGS. 10A and 10B show the characteristics of NY-ESO-1 and MART1 TCR transduced T cells from healthy donors used in validation studies. Boxed population represents the percentage of transduced T cells expressing NY-ESO-1 (A) or MART1 (B) TCRs on the cell surface as determined by flow cytometry.

Figures 11A, 11B:
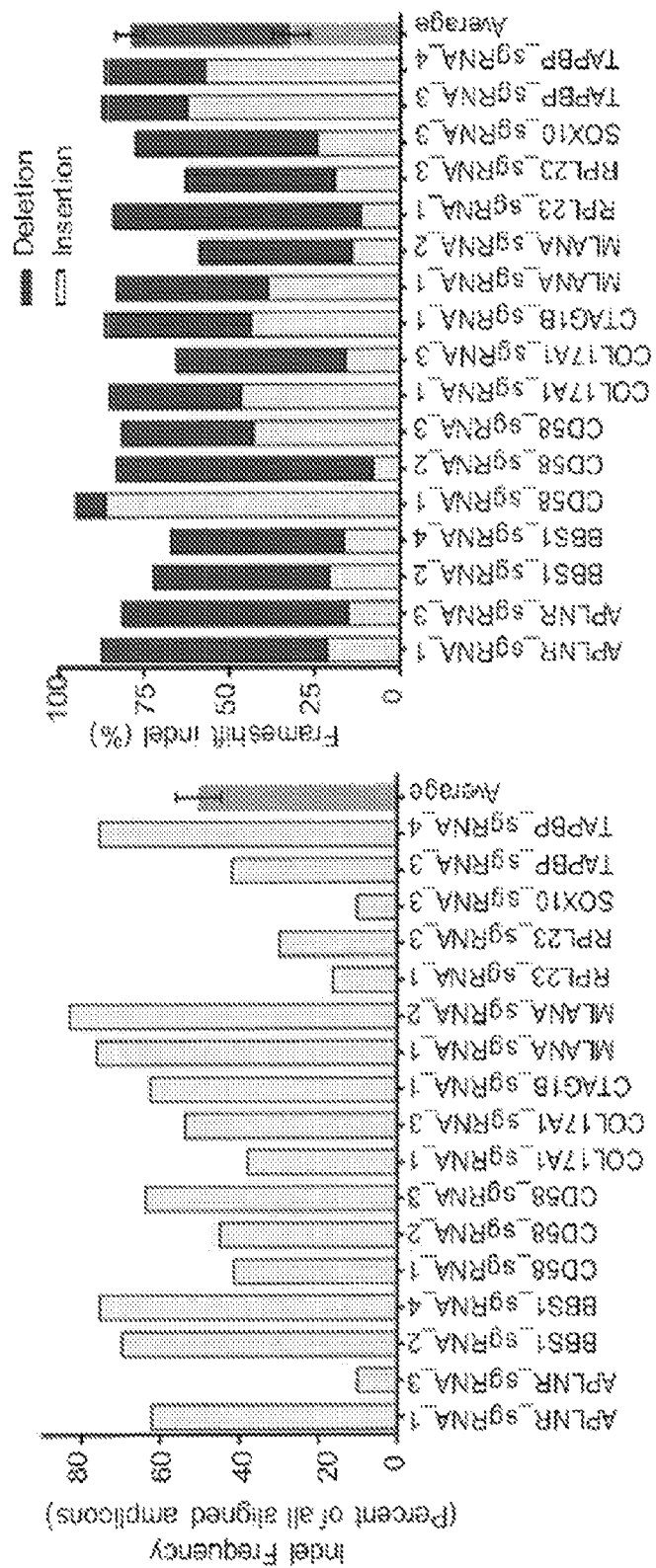
Figure 11C:
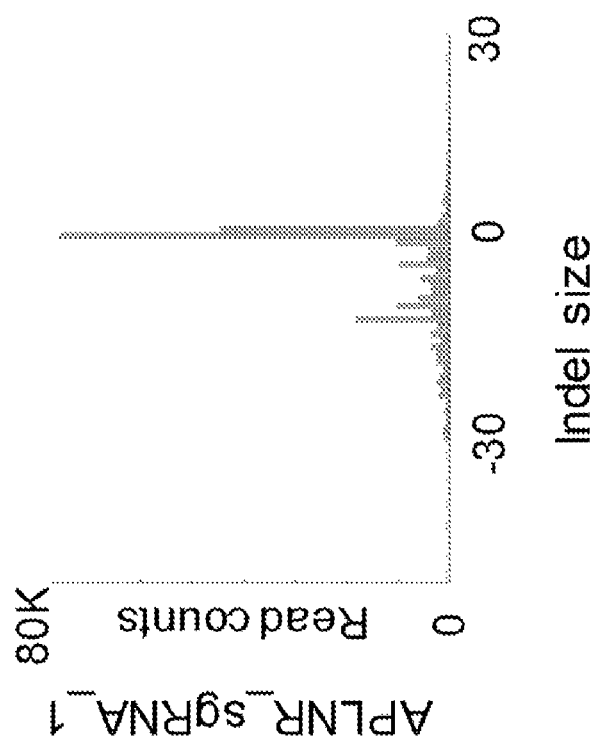
Figures 11D, 11E:
Figures 11F, 11G:
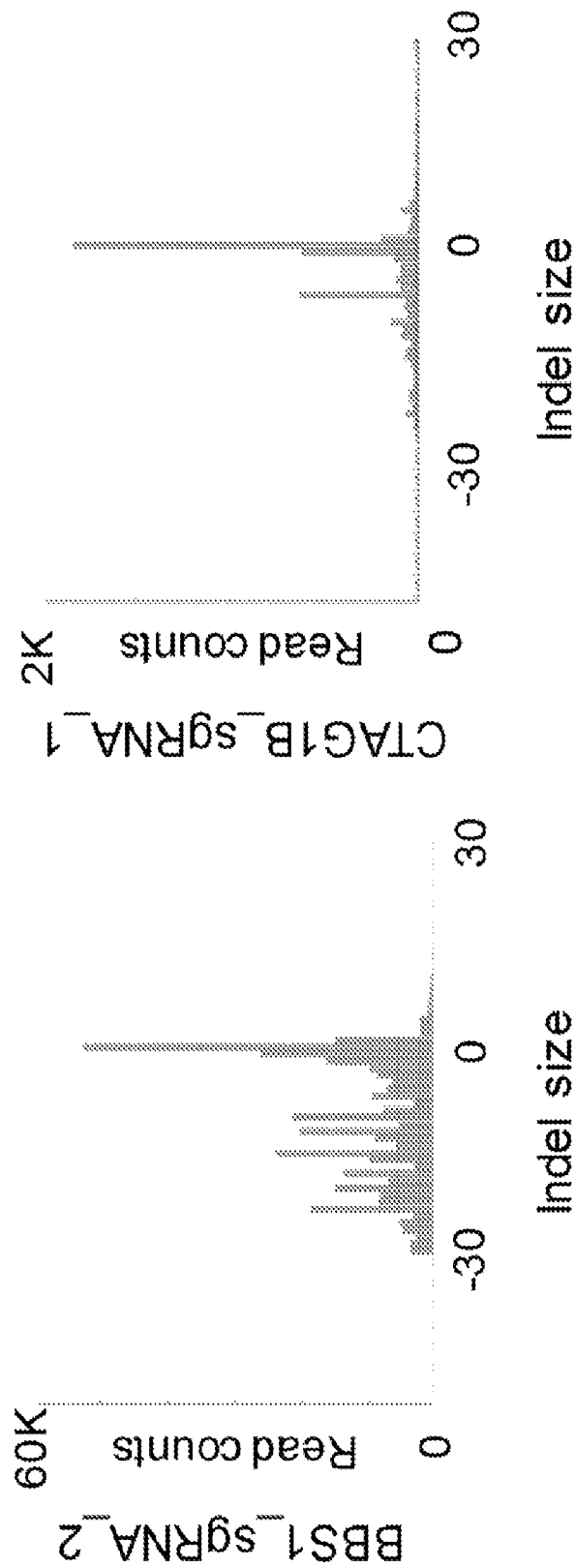
Figures 11H, 11I:
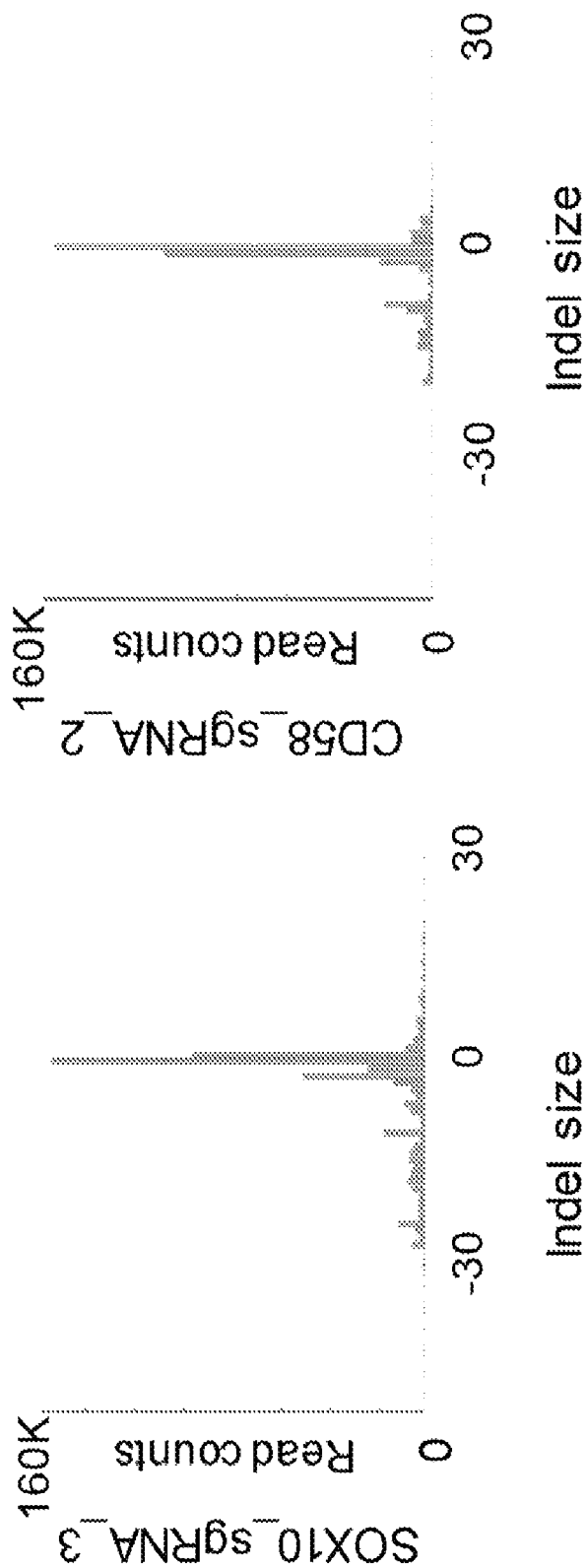

FIG. 11A shows the total indel frequencies detected for each lentiviral CRISPR.

FIG. 11B shows the distribution of types of indel mutations.

FIGS. 11C-11K show representative indel plots for data shown in FIG. 11B. Each subpanel shows the distribution of indel sizes for a single sgRNA at its intended genomic target locus: APLNR (C), COL17A1 (D), RPL23 (E), BBS1 (F), CTAG1B (G), SOX10 (H), CD58 (I), MLANA (4), and TAPBP (K). Negative values indicate deletions and positive values indicate insertions.

Figures 12A, 12B:
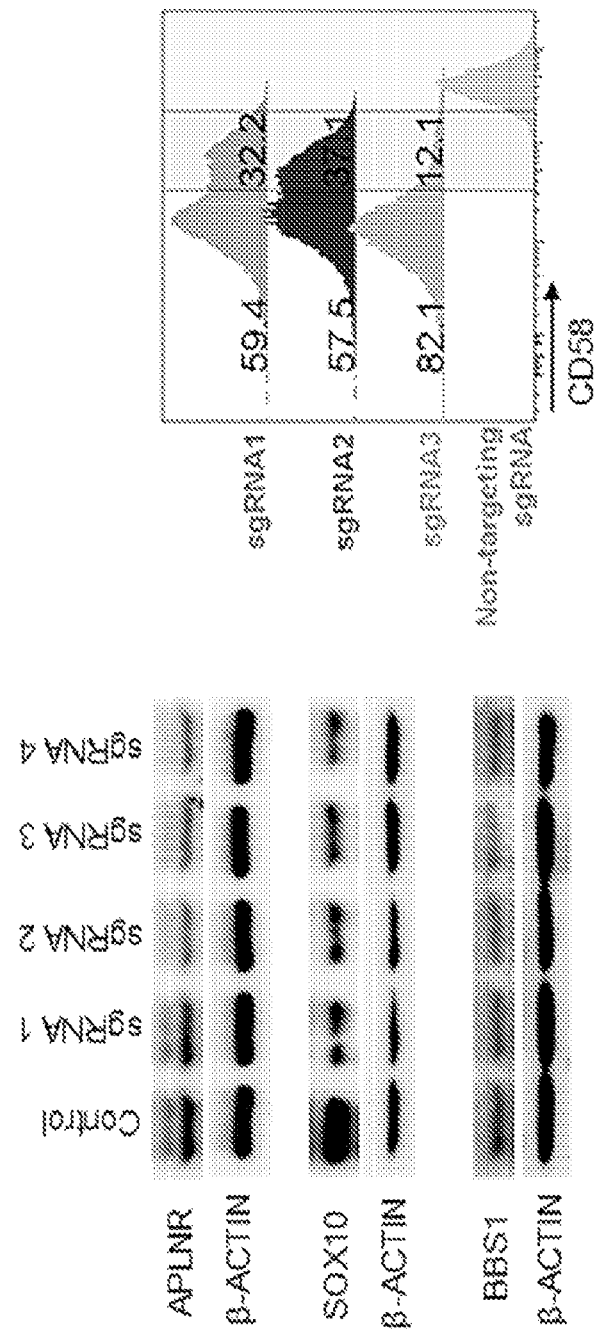

FIG. 12A shows the results of a Western blot analysis of CRISPR mediated gene perturbations in A375 cells after 4-5 days of puromycin selection.

FIG. 12B is a representative FACS plot of CRISPR mediated gene perturbations at the CD58 locus in A375 cells. The numbers shown in the box are as follows: sgRNA1: 59.4 (left) and 32.2 (right). sgRNA2: 57.5 (left) and 37.1 (right). sgRNA3: 82.1 (left) and 12.1 (right).

Figure 13:
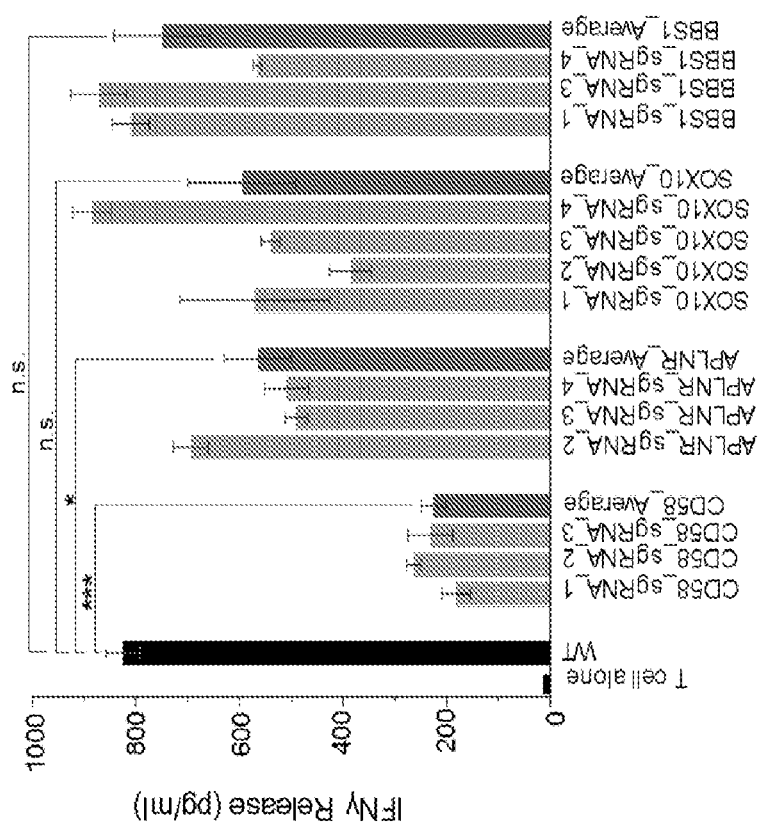

FIG. 13 is a bar graph showing the results of an IFNγ ELISA assay performed on supernatants 24 h post co-culture of CRISPR edited A375 cells with ESO T cells. CD58 edited cells resist T cell mediated cytolysis by limiting IFNγ release from T cells while BBS1 edited cells does not alter IFNγ release. Gray bar denotes average of 3-4 sgRNAs targeting a gene. ***P<0.001 *P<0.05, n=3 co-culture replicates. Error bar denotes mean±S.E.M.

FIGS. 14A-14D show bar graphs showing the results of a FACS analysis of surface phenotypic characteristics of APLNR, BBS1, CD58 and SOX10 edited A375 cells post 24 hr of coculture with ESO T cells. Untransduced A375 cells are represented as 'WT'. The loss of these four genes, APLNR, BBS1, CD58 and SOX10, neither significantly reduced the expression of antigen presentation gene 132M (D) nor increased the expression of checkpoint ligands, PD-L1 (A), PD-L2 (B) and galectin-9 (C), after 24 hours of co-culture with ESO T cells. n=3 replicates. Data shown as an average of tested 3-4 sgRNAs per gene. Error bar denotes mean±S.E.M.

Figure 15A:
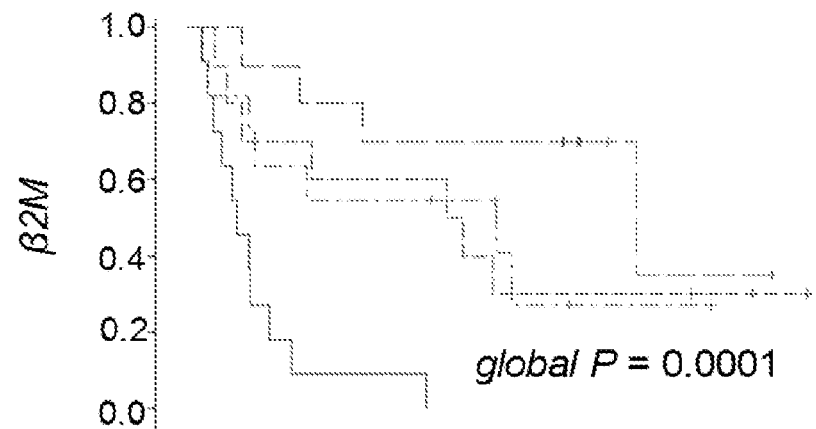
Figure 15C:
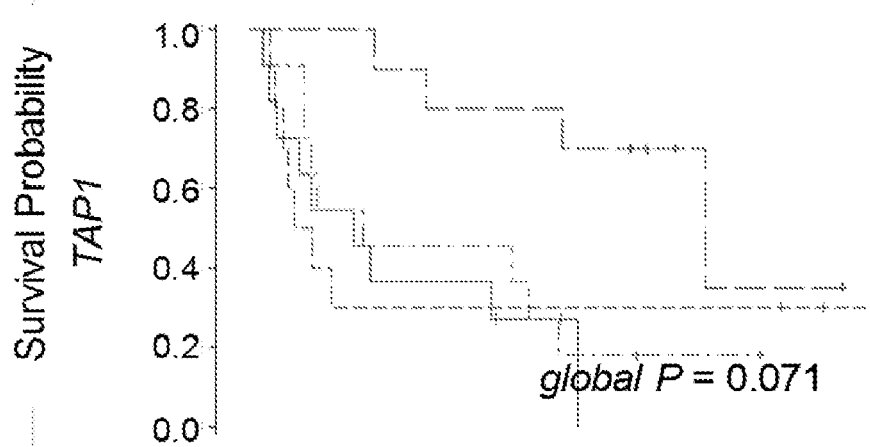
Figure 15D:
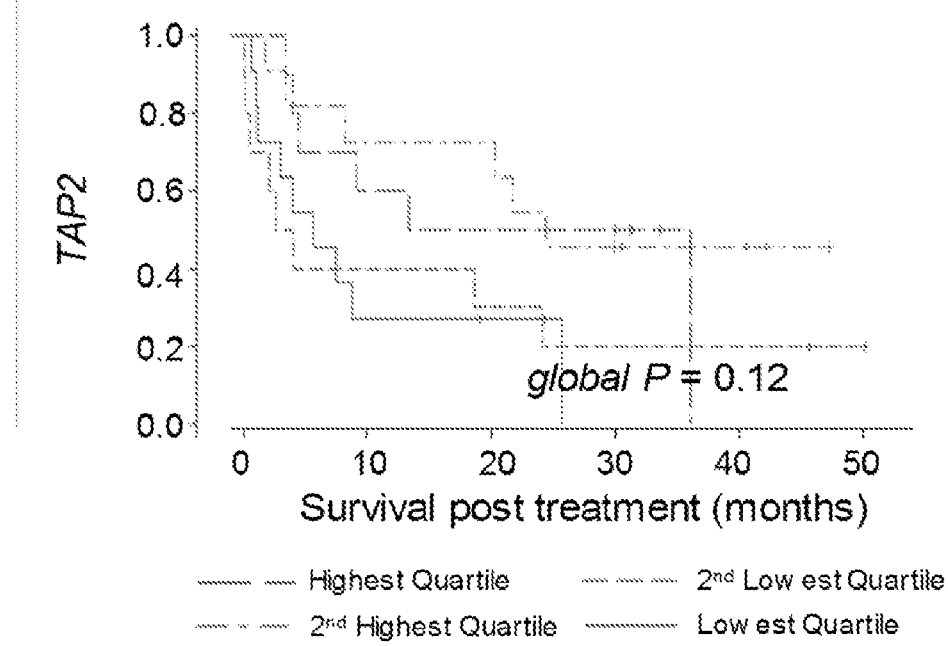

FIGS. 15A, 15C, and 15D show the results of an initial exploratory analysis in which data were divided into quartiles based on RPKM values of each individual gene and the four groups were evaluated for their association with survival. The global p-values shown indicate the overall association of the quartiles of gene expression levels with survival; a small p-value suggests a difference in the groups with respect to survival. For these three genes, a final division at either the lower quartile, the median, or the upper quartile was made which resulted in the most significant prognostic split of the data with respect to association with survival (P<0.0001 for B2M (A) and P=0.032 for TAP1 (C) as shown in FIGS. 4A-4B, and P=0.05 for TAP2 (D) shown here). Since P<0.10 for each difference in outcome between two groups after adjustment in the univariate analyses shown, a Cox proportional hazards model analysis was performed including these three genes (plus BBS, adjusted P=0.075, data not shown) to assess whether they had a joint impact on survival. By backward selection, the final Cox model indicated that only the lower quartile of B2M levels was significantly associated with poorer survival, and the other genes did not contribute significantly to the model when the four genes were considered jointly (Hazard Ratio (HR)=5.72; 95% CI for HR: 2.41-13.58; P<0.0001)

Figure 15B:
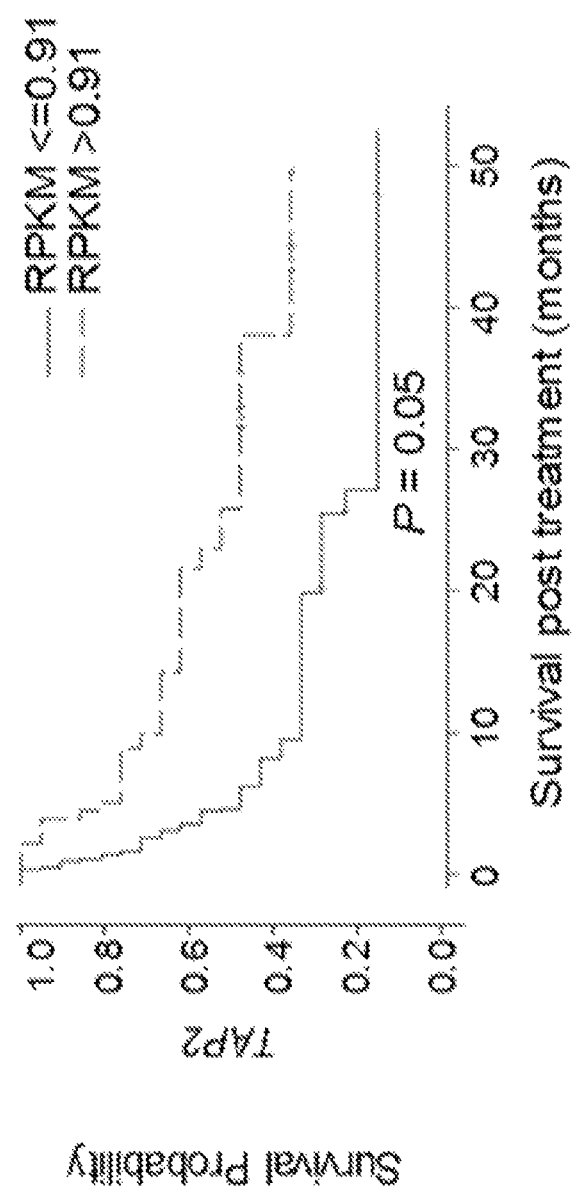

FIG. 15B shows the results of an analysis data were split into two groups by indicated RPKM values for each gene based on the trends from global analysis of survival probability in FIGS. 15A, 15C, and 15D according to the quartiles of expression levels. The association between TAP2 expression levels and survival is shown here.

Figure 16:
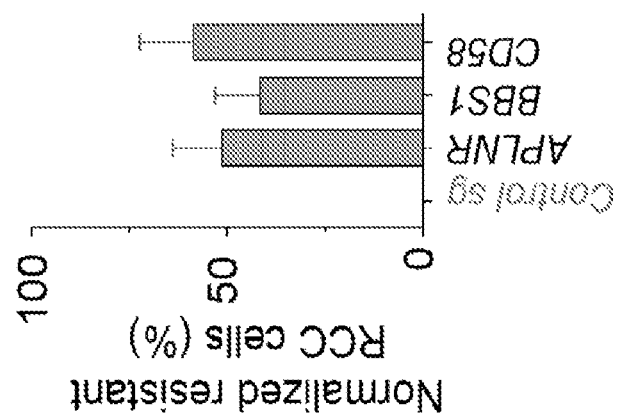

FIG. 16 is a graph showing the normalized percentage of RCC cells resistant to T cell mediated cytolysis when the RCC cells are modified with control sgRNA or are modified to knock out APLNR, BBS1, or CD8.

Figure 17B:
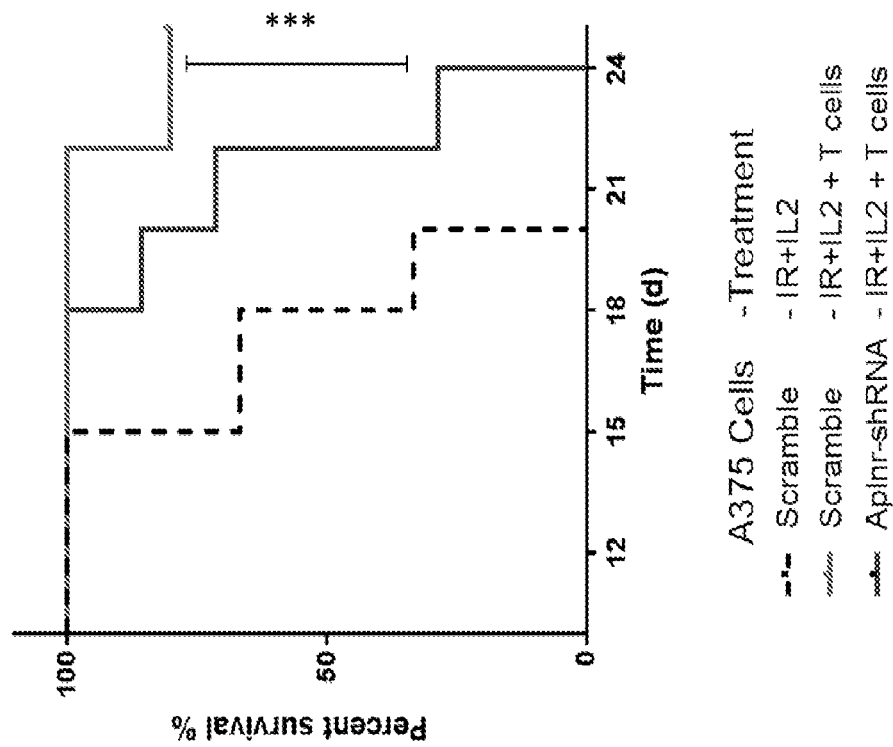
Figure 17A:
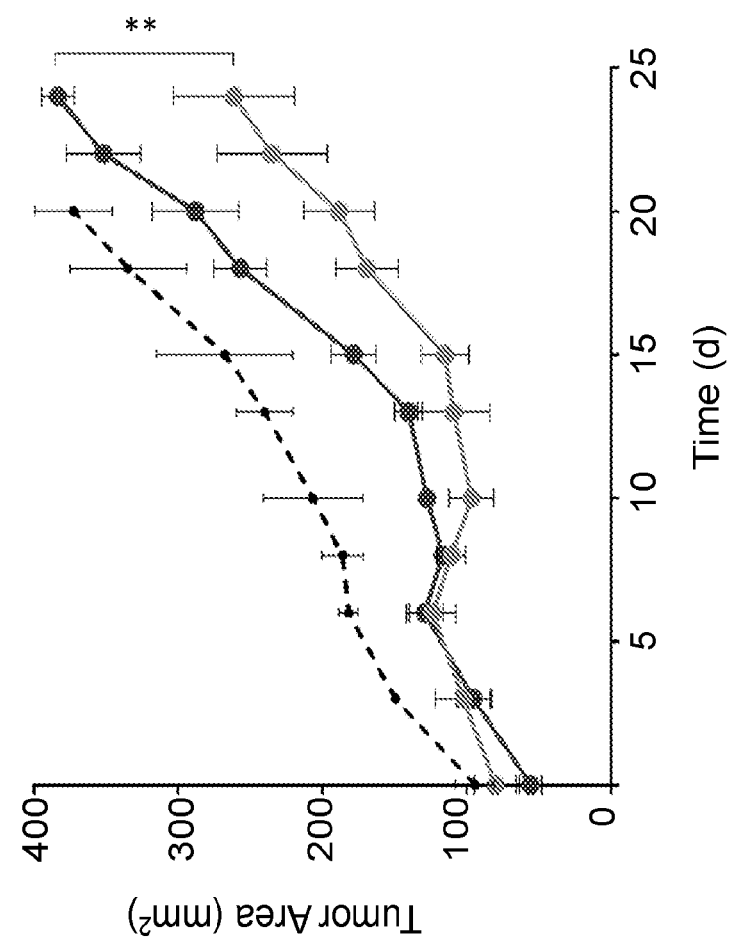

FIGS. 17A and 17B are graphs showing the tumor area (A) and survival (B) over time (days) measured in mice bearing tumors grown from cells, wherein the cells were modified with irrelevant (scramble) shRNA and the mice were treated with IR and IL-2 alone (dashed line) or treated with IR, IL-2, and T cells (grey line) or wherein the cells were treated with anti-Apinr shRNA and treated with IR and IL-2 (black line).

Figure 18A:
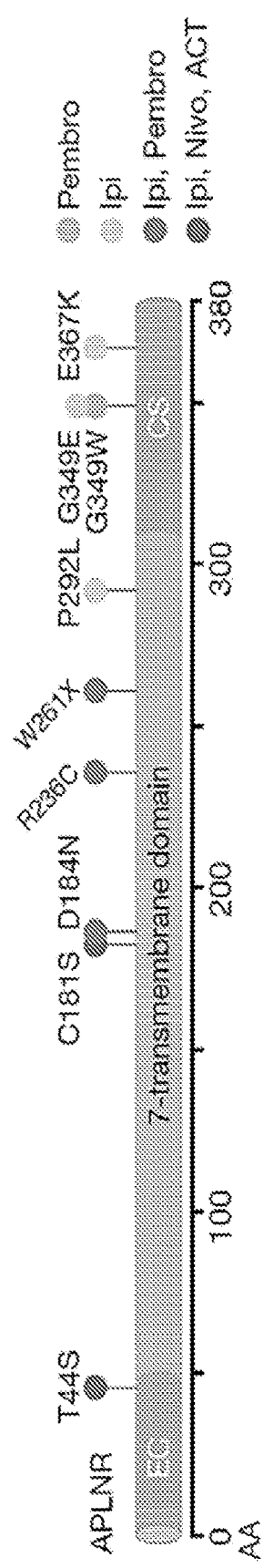

FIG. 18A is a schematic illustrating the extracellular (EC), 7-transmembrane, and cytoplasmic signaling (CS) domains of the 380-amino acid (AA) residues of the APLNR protein. The positions of various non-synonymous mutations are indicated.

Figure 18B:
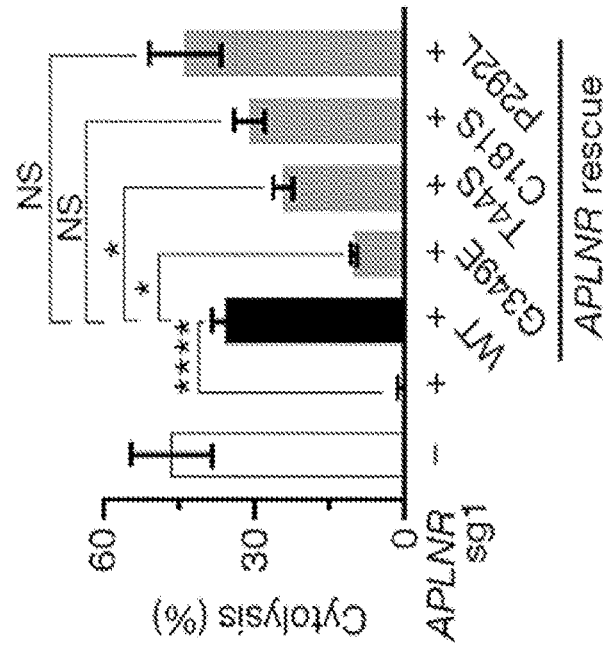

FIG. 18B is a graph showing the percentage of tumor cells lysed by T cells. Tumor cells were treated (+) or untreated (−) with APLNR sg RNA (sg1) and were further treated with wild type (WT) rescue APLNR RNA or APLNR RNA with the indicated mutation. NS=not statically significant.

Figures 19A, 19B:
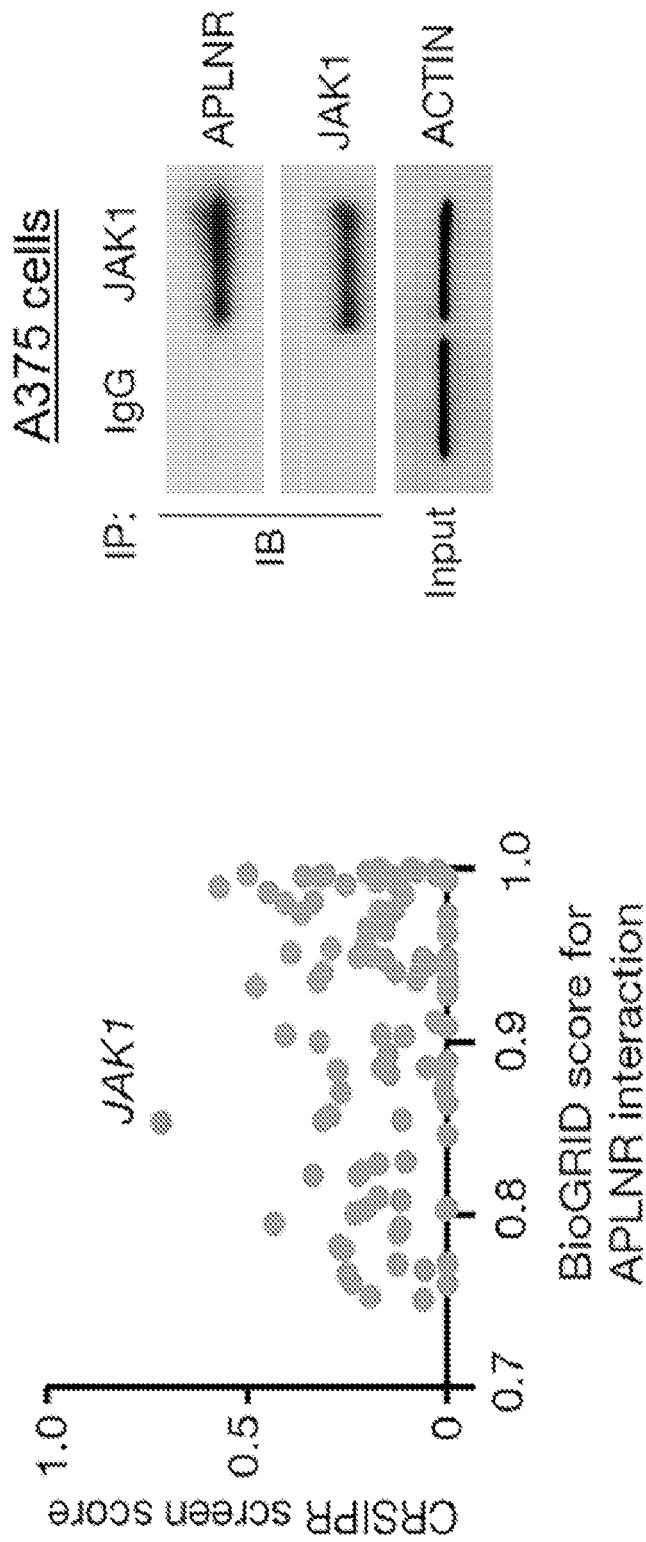

FIG. 19A is a graph which plots the CRISPR screen score against the BIOGRID database score for APLNR interaction. JAK1 is indicated.

FIG. 19B is a photographic image of a Western blot (immunoblot (IB)) probed for APLNR after immunoprecipitation (IP) pull-down of JAK1 from A375 cell lysates. IP of IgG served as a negative control. Actin served as a positive control.

Figure 20:
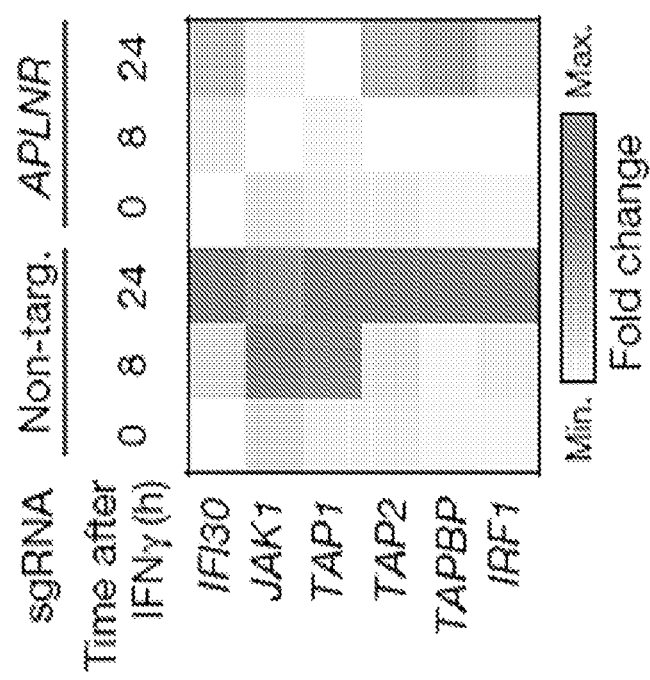

FIG. 20 is a heat map showing the fold change in expression of the indicated genes 0, 8, or 24 hours following treatment of wild type (non-targ.) or APLNR knockout tumor cells with IFNγ. Darker shading indicates a maximum fold-change in expression. Lighter shading indicates a minimum fold change in expression.

Figures 21A, 21B:
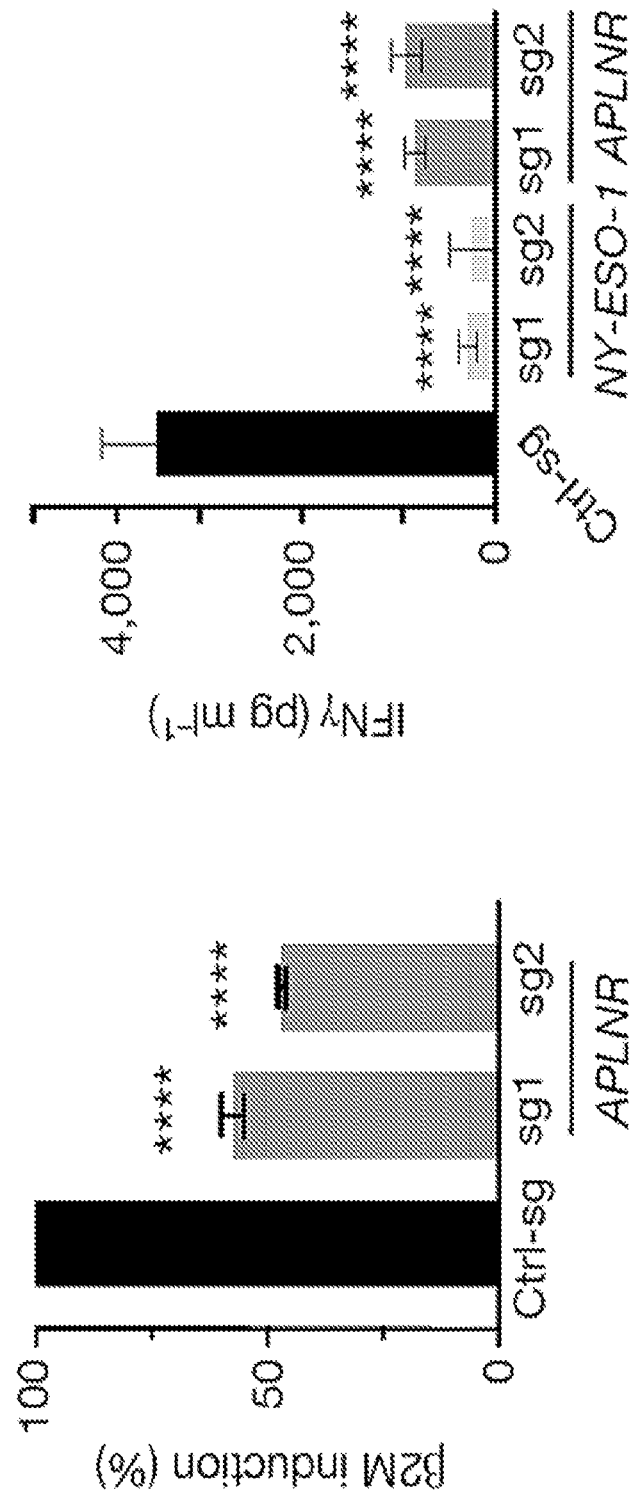

FIG. 21A is a graph showing the percentage of tumor cells with surface 132M expression upon co-culture with anti-NY-ESO-1 T cells as measured by FACS. The tumor cells were CRISPR-edited using control sgRNA, anti-APLNR sg1 RNA, or anti-APLNR sg2 RNA (n=3 biological replicates).

FIG. 21B is a graph showing IFNγ secretion (pg ml$^{-1}$) by T cells following co-culture with tumor cells which had been CRISPR-edited using anti-NY-ESO-1 sg1 RNA, anti-NY-ESO-1 sg2 RNA, APLNR sg1 RNA, or anti-APLNR sg2 RNA (n=3 biological replicates).

FIGS. 22A and 22B are graphs showing the tumor area (mm$^2$) in mice receiving no treatment (A) or treatment with Pmel ACT (B) at various time points (days) (d) after adoptive cell transfer. The tumors in the mice were grown from unmanipulated tumor cells (control; circles) or tumor cells CRISPR-edited to knockout b2M (open triangles) or APLNR (closed triangles) expression. Significance for tumor growth kinetics was calculated by Wilcoxon rank-sum test. For 'Pmel ACT' groups, n=9 mice in control group, n=10 mice per B2m-sg and Apinr-sg groups. All values are mean±s.e.m. **P<0.0001, P<0.01, *P<0.05. Data are representative of two independent experiments.

FIG. 22C is a graph showing the probability of survival of mice receiving treatment with Pmel ACT at various time points (days) (d) after adoptive cell transfer. The tumors in the mice were grown from unmanipulated tumor cells (control; circles) or tumor cells CRISPR-edited to knockout b2M (open triangles) or APLNR (closed triangles) expression. Survival significance was assessed by a log-rank Mantel-Cox test (n=5 mice per 'no treatment' groups). For 'Pmel ACT' groups, n=9 mice in control group, n=10 mice per B2m-sg and Apinr-sg groups. All values are mean±s.e.m. **P<0.0001, P<0.01, *P<0.05. Data are representative of two independent experiments.

Figures 23A, 23B:
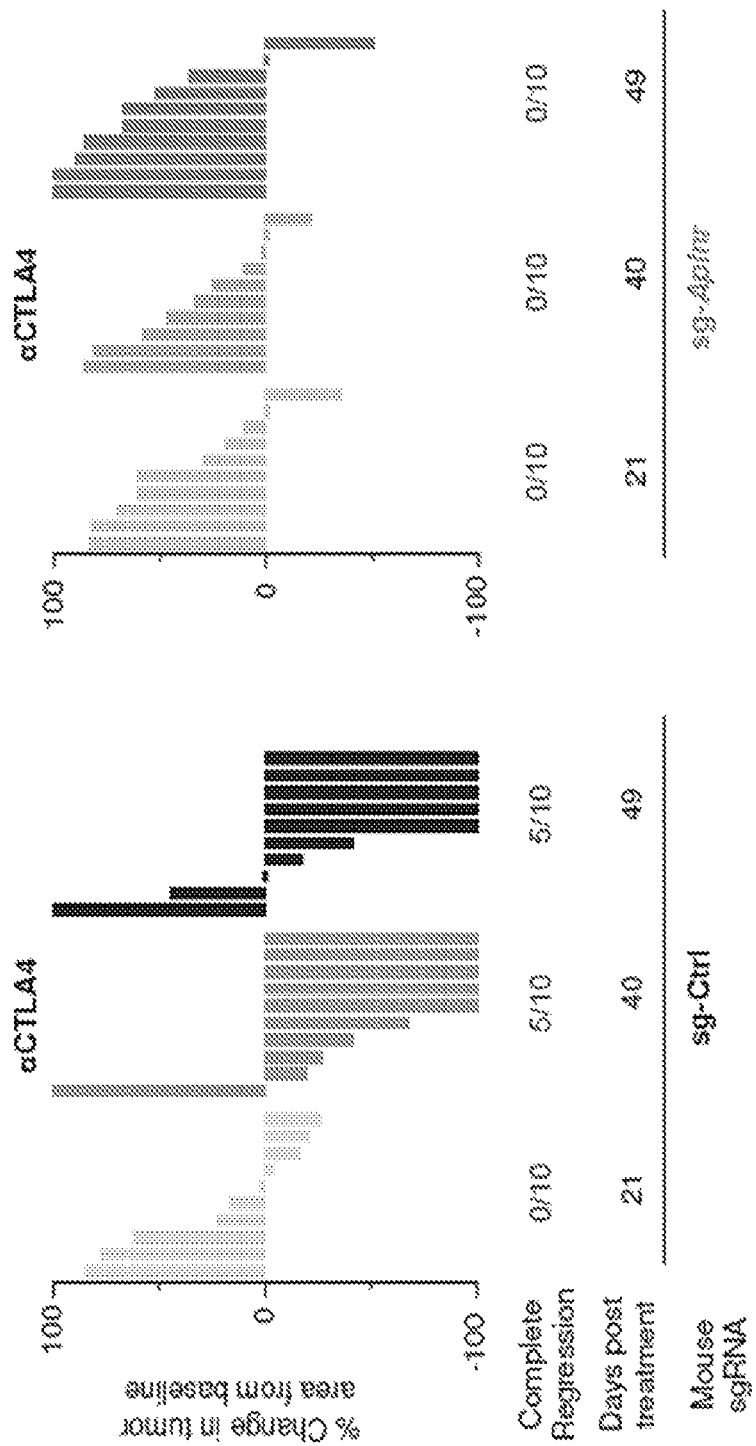

FIGS. 23A-23B are waterfall plots showing the percent change in tumor area from baseline (tumor measurements from the first day of antibody injections) to tumors measured on days 21, 40, and 49 post-treatment with antibodies. The tumors in the mice were grown from tumor cells CRISPR-edited to knockout APLNR expression (sg-Apinr) (B) or CRISPR-edited using control guide RNA (sg-Ctrl) (A). Significance of treatment efficacy was determined by Fisher's exact test comparison of sg-Ctrl versus sg-Apinr groups treated with anti-CTLA4 using the number of progressing tumors and completely regressed tumors in each group. n=8/9 mice for IgG groups. n=10 mice for anti-CTLA4 groups.

DETAILED DESCRIPTION OF THE INVENTION

It has been discovered that a mutation in, or a reduction in expression of, one or more of certain genes described herein renders a cancer cell resistant to T cell-mediated cytolysis. Accordingly, the presence of the mutation in, or the reduction of expression of, the one or more genes in a cancer cell of a patient may decrease the effectiveness of T cell anti-cancer therapies. Conversely, the absence of the mutation in, or a lack of a decrease of expression of, the one or more genes in a cancer cell of a patient may indicate that a T cell anti-cancer therapy may be effective for treating the cancer in the patient. Accordingly, detection of the presence or absence of the mutation in, or detection of a decrease or lack of decrease in the expression of, the one or more genes may be useful for selecting a type of therapy which may be more effective for treating the patient's cancer.

An embodiment of the invention provides a method of selecting a therapy for a cancer patient. The method may comprise detecting a mutation in one or more genes in a cancer cell from the patient which is not present in a noncancerous cell.

The one or more genes is selected from the group consisting of PTCD2, TWF1, DEFB134, BBS1, SOX10, APLNR, CD58, COL17A1, CRKL, hsa-mir-101-2, hsa-mir-548s, MAD2L1, MLANA, PSMB5, RNPS1, RPL10A, RPL23, SRP54, TAF3, TAP1, TAP2, TAPBP, TBXAS1, GMIP, OTOA, LAIR1, CLEC1, GPSM3, TRAF1, JAK2, TAPBPL, ICAM1, LILRA1, LILRA3, STAT1, and HLA-F. Nucleotide and amino acid sequences for the above genes in humans are accessible from publicly available databases, e.g., in the NCBI Entrez database accession numbers shown in Table I below.

TABLE I

| Gene | Full name | Entrez gene ID No. |
| --- | --- | --- |
| APLNR | Apelin Receptor | 187 |
| BBS1 | Bardet-Biedl Syndrome 1 | 582 |
| CD58 | CD58 Molecule | 965 |
| CLEC1 | C-Type Lectin Domain Family 1 Member A | 51267 |
| COL17A1 | Collagen Type XVII Alpha 1 | 1308 |
| CRKL | V-Crk Avian Sarcoma Virus CT10 Oncogene Homolog-Like | 1399 |
| DEFB134 | Defensin Beta 134 | 613211 |
| GMIP | GEM Interacting Protein | 51291 |
| GPSM3 | G-Protein Signaling Modulator 3 | 63940 |
| HLA-F | Major Histocompatibility Complex, Class I, F | 3134 |
| hsa-mir-101-2 | MicroRNA 101-2 | 406894 |
| hsa-mir-548s | MicroRNA 548s | 100422862 |
| ICAM1 | Intercellular Adhesion Molecule 1 | 3383 |
| JAK2 | Janus Kinase 2 | 3717 |
| LAIR1 | Leukocyte Associated Immunoglobulin Like Receptor 1 | 3903 |
| LILRA1 | Leukocyte Immunoglobulin Like Receptor A1 | 11024 |
| LILRA3 | Leukocyte Immunoglobulin Like Receptor A3 | 11026 |
| MAD2L1 | MAD2 Mitotic Arrest Deficient-Like 1 (Yeast) | 4085 |

TABLE I-continued

| Gene | Full name | Entrez gene ID No. |
| --- | --- | --- |
| MLANA | Melan-A | 2315 |
| OTOA | Otoancorin | 146183 |
| PSMB5 | Proteasome Subunit Beta 5 | 5693 |
| PTCD2 | Pentatricopeptide Repeat Domain 2 | 79810 |
| RNPS1 | RNA Binding Protein With Serine Rich Domain 1 | 10921 |
| RPL10A | Ribosomal Protein L10a | 4736 |
| RPL23 | Ribosomal Protein L23 | 9349 |
| SOX10 | SRY-Box 10 | 6663 |
| SRP54 | Signal Recognition Particle 54 kDa | 6729 |
| STAT1 | Signal Transducer And Activator Of Transcription 1 | 6772 |
| TAF3 | TATA-Box Binding Protein Associated Factor 3 | 83860 |
| TAP1 | Transporter 1, ATP-Binding Cassette, Sub-Family B (MDR/TAP) | 6890 |
| TAP2 | Transporter 2, ATP-Binding Cassette, Sub-Family B (MDR/TAP) | 6891 |
| TAPBP | TAP Binding Protein (Tapasin) | 6892 |
| TAPBPL | TAP Binding Protein Like | 55080 |
| TBXAS1 | Thromboxane A Synthase 1 | 6916 |
| TRAF1 | TNF Receptor Associated Factor 1 | 7185 |
| TWF1 | Twinfilin Actin Binding Protein 1 | 5756 |

The cancer cell may be obtained from any bodily sample derived from a patient which contains or is expected to contain tumor or cancer cells. The noncancerous (normal, healthy) cell may be obtained from any bodily sample which does not contain tumor or cancer cells. The bodily sample may be any tissue sample such as blood, a tissue sample obtained from the primary tumor or from tumor metastases, or any other sample containing tumor or cancer cells. The normal, noncancerous cell may be obtained from the patient or a different individual.

Genetic material (such as DNA or RNA) may be obtained directly from the patient, or the genetic material can be copied or amplified from genetic material within the patient's cells (e.g., via polymerase chain reaction (PCR), reverse transcription polymerase chain reaction (RT-PCR), or other suitable technique). To ensure that a sufficient quantity of genetic material is available for testing, the genetic material may be amplified from cells obtained from the patient, and the amplified genetic material is assayed in accordance with the inventive method. Preferably, a PCR or RT-PCR strategy is employed using primers flanking all or a portion of a gene set forth in Table I, so as to amplify this sequence from the patient for the assay. While the method may comprise amplifying and assaying one copy of a gene in Table I, preferably, the method comprises amplifying both copies of the gene from the patient, so that both can be assayed in accordance with the inventive method.

However obtained, the method may comprise assaying the genetic material to detect a mutation in one or more of the genes set forth in Table I (e.g., a mutation at least one of the two alleles of any gene in Table I) in a cancer cell of the patient which is not present in a noncancerous cell. Any test able to detect mutations appropriate to the type of genetic material (e.g., genomic DNA (gDNA), cDNA, RNA) may be employed. The assaying may comprise obtaining, from the cancer cell and from the noncancerous cell, the sequence of at least a portion of the genetic sequence of one or more genes set forth in Table I or obtaining the sequence of substantially all of the genetic sequence of one or more genes set forth in Table I. In an embodiment, the method may further comprise comparing the sequence of the gene of a cancer cell from the patient to the sequence of the corresponding gene in the noncancerous cell (e.g., the wild type genetic sequence) and identifying any differences between the sequence of the gene in the cancer cell from the patient and the corresponding gene in the noncancerous cell (e.g., the wild type genetic sequence) to detect any mutations. In order to detect a mutation, the method may comprise sequencing nucleic acid such as DNA or RNA of the one or more genes in the cancer cell. The method may further comprise sequencing nucleic acid such as DNA or RNA of the one or more genes in the noncancerous cell.

In an embodiment of the invention, the method comprises detecting a mutation in 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, or 35 or more of the genes in Table I in a cancer cell from the patient. In an embodiment of the invention, the method comprises detecting a mutation in all 36 of these genes in a cancer cell from the patient.

The mutation may be any mutation which decreases one or both of (i) the expression of and (ii) the activity of the polypeptide(s) encoded by the one or more genes. The gene with the mutation may encode a mutated amino acid sequence. In this regard, the mutation may be a "non-silent mutation." Non-limiting examples of mutations that may be detected in the inventive methods include missense, nonsense, insertion, deletion, duplication, frameshift, and repeat expansion mutations. The mutation may be a loss-of-function mutation. A loss-of-function mutation decreases or eliminates expression or activity of the encoded polypeptide. One or more mutations may be detected in a given gene in accordance with the invention.

In an embodiment of the invention, the mutation may be any mutation which decreases the expression of one or both of the mRNA and the polypeptide encoded by the gene. In this regard, a cell with the mutation expresses a lower amount of one or both of mRNA and polypeptide encoded by the gene as compared to the noncancerous cell. The amount of one or both of mRNA and polypeptide expressed by the cell with the mutation may be, for example, about 10% lower, about 20% lower, about 30% lower, about 40% lower, about 50% lower, about 60% lower, about 70% lower, about 80% lower, about 90% lower as compared to that expressed by the noncancerous cell. In an embodiment of the invention, a cell with the mutation exhibits no detectable expression of one or both of mRNA and polypeptide encoded by the gene. Methods of measuring the level of mRNA expression are known in the art and may include, for example, quantitative polymerase chain reaction (qPCR), RNA sequencing (RNAseq), Northern blot, immunohistochemistry, fluorescence in-situ hybridization (FISH), and other methods utilizing sequence probes which are complementary to the RNA of interest. Methods of measuring the level of polypeptide expression are known in the art and may include, for example, Western blot, immunohistochemistry, PROTEINSIMPLE protein quantitation, Edman peptide sequencing, and mass spectrometry.

In an embodiment of the invention, the mutation may be any mutation which decreases the biological activity of the polypeptide(s) encoded by the one or more genes. In this regard, a cell with the mutation exhibits a decreased biological activity of the polypeptide(s) as compared to the noncancerous cell. The biological activity of the polypeptide(s) expressed by the cell with the mutation may be, for example, about 10% lower, about 20% lower, about 30% lower, about 40% lower, about 50% lower, about 60% lower, about 70% lower, about 80% lower, about 90% lower as compared to that of the noncancerous cell. In an embodiment of the invention, a cell with the mutation exhibits no detectable biological activity of the polypeptide encoded by the gene. Exemplary biological activities of genes set forth in Table I are set forth in Table II.

TABLE II

| Gene | Exemplary Biological Activity |
|---|---|
| APLNR | G-protein-coupled receptor (GPCR) |
| BBS1 | A coat complex protein required for the sorting of specific membrane proteins to the primary cilia |
| CD58 | T cell co-stimulation |
| CLEC1 | C-type lectin-like receptor 1 (defense protein) |
| COL17A1 | Cell structure |
| CRKL | Kinase |
| DEFB134 | Defense response to bacterium |
| GMIP | GEM-interacting protein |
| GPSM3 | Interacts with subunit of G(i) alpha proteins and regulates the activation of G(i) alpha proteins |
| HLA-F | Antigen Presentation: Folding, assembly and peptide loading of class I MHC |
| hsa-mir-101-2 | microRNA regulates expression of other RNAs |
| hsa-mir-548s | microRNA regulates expression of other RNAs |
| ICAM1 | Adhesion molecule for leukocyte migration |
| JAK2 | Interferon signaling transducer |
| LAIR1 | Regulation of immune response; Inhibitory receptor |
| LILRA1 | May act as receptor for class I MHC antigens |
| LILRA3 | Acts as soluble receptor for class I MHC antigens |
| MAD2L1 | Mitotic assembly |
| MLANA | Melanoma antigen |
| OTOA | Cell matrix adhesion |
| PSMB5 | Ubiquitination |
| PTCD2 | PolyA RNA binding |
| RNPS1 | Eukaryotic Initiation Factor 2 (EIF2) signaling |
| RPL10A | EIF2 signaling |
| RPL23 | EIF2 signaling |
| SOX10 | Transcription factor |
| SRP54 | Signal related peptide |
| STAT1 | Signal transducer and transcription activator that mediates cellular responses to interferons (IFNs), cytokine KITLG/SCF, other cytokines, and other growth factors |
| TAF3 | Transcription initiation |
| TAP1 | MHC Class I |
| TAP2 | MHC Class I |
| TAPBP | MHC Class I |
| TAPBPL | MHC Class I |
| TBXAS1 | 12-hydroxyheptadecatrienoic acid synthase activity |
| TRAF1 | Adapter molecule that regulates the activation of NF-kappa-B and JNK |
| TWF1 | Barbed-end actin filament capping |

The method may further comprise selecting the patient for a therapy which is not a T cell therapy when the mutation in one or more genes is present in the cancer cell and selecting the patient for a T cell therapy when the mutation in one or more genes of Table I is not present in the cancer cell. Preferably, the method comprises selecting the patient for a T cell therapy when a mutation which decreases one or both of expression and activity of the encoded polypeptide is not present in all of the 36 genes listed in Table I. The presence of a mutation in one or more genes of Table I indicates that the cancer cells in the patient are resistant to T cell-mediated cytolysis and, consequently, that T cell therapy may be less effective in treating the cancer in the patient. The absence of a mutation in one or more of (or all of) the genes of Table I indicates that the cancer cells in the patient are sensitive to T cell-mediated cytolysis and, consequently, that T cell therapy may be effective in treating the cancer in the patient.

Another embodiment of the invention provides a method of selecting a therapy for a cancer patient and treating cancer in the patient. The method may comprise selecting a therapy for the cancer patient by detecting a mutation in one or more genes in a cancer cell by any of the methods described herein with respect to other aspects of the invention. The method may further comprise treating the patient by administering a therapy which is not a T cell therapy to the patient in an amount effective to treat cancer in the patient when the mutation in the one or more genes is present in the cancer cell and treating the patient by administering a T cell therapy to the patient in an amount effective to treat cancer in the patient when the mutation in the one or more genes is not present in the cancer cell. Preferably, the method comprises treating the patient by administering a T cell therapy to the patient in an amount effective to treat cancer in the patient when the mutation in all 36 of the genes set forth in Table I is not present in the cancer cell.

Alternatively or additionally, a mutation may be detected in a polypeptide encoded by one or more of the genes set forth in Table I. Accordingly, another embodiment of the invention provides a method of selecting a therapy for a cancer patient, the method comprising detecting a mutation in one or more polypeptides in a cancer cell from the patient which is not present in a noncancerous cell, wherein the one or more polypeptides is encoded by a gene selected from the group consisting of PTCD2, TWF1, DEFB134, BBS1, SOX10, APLNR, CD58, COL17A1, CRKL, hsa-mir-101-2, hsa-mir-548s, MAD2L1, MLANA, PSMB5, RNPS1, RPL10A, RPL23, SRP54, TAF3, TAP1, TAP2, TAPBP, TBXAS1, GMIP, OTOA, LAIR1, CLEC1, GPSM3, TRAF1, JAK2, TAPBPL, ICAM1, LILRA1, LILRA3, STAT1, and HLA-F. The cancer cell and the noncancerous cell may be as described herein with respect to other aspects of the invention. The mutation may decrease the activity of the polypeptide, as described herein with respect to other aspects of the invention. The polypeptide with the mutation may be encoded by a gene set forth in Table I including any of the types of mutations described herein with respect to other aspects of the invention.

The method may comprise assaying a sample comprising cancer cells from the patient to detect a mutation in a polypeptide encoded by one or more genes set forth in Table I. For example, the polypeptide can be purified from the sample (either partially or substantially and assayed via immunohistological techniques (e.g., Western blotting, ELISA, immunoprecipitation, etc.) using one or more antibodies recognizing the mutated polypeptide but not the corresponding polypeptide from the noncancerous cell (e.g., the wild type polypeptide). In this regard, the assaying may comprise contacting the sample with an antibody that specifically binds to the mutated polypeptide and does not bind to the corresponding polypeptide from the noncancerous cell (e.g., the wild type polypeptide), thereby forming a complex, and detecting the complex. Alternatively, or in conjunction, the sample from the patient can be assayed using one or more antibodies recognizing the polypeptide from the noncancerous cell (e.g., the wild type polypeptide) but not the corresponding mutated polypeptide. In this regard, the assaying may comprise contacting the sample with an antibody that specifically binds to the polypeptide from the noncancerous cell and does not bind to the corresponding mutated polypeptide, thereby forming a complex, and detecting the complex.

The method may further comprise selecting the patient for a therapy which is not a T cell therapy when the mutation is present in the cancer cell, as described herein with respect to other aspects of the invention. The method may comprise selecting the patient for a T cell therapy when the mutation is not present in the cancer cell, as described herein with respect to other aspects of the invention. Preferably, the method comprises selecting the patient for a T cell therapy when the mutation which decreases activity of the encoded polypeptide is not present in the polypeptides encoded by all of the 36 genes listed in Table I.

Another embodiment of the invention provides a method of selecting a therapy for a cancer patient and treating the cancer in the patient. The method may comprise selecting a therapy for the cancer patient by detecting a mutation in one or more polypeptides in a cancer cell by any of the methods described herein with respect to other aspects of the invention. The method may further comprise treating the cancer in the patient by administering a therapy which is not a T cell therapy to the patient in an amount effective to treat cancer in the patient when the mutation in the one or more polypeptides is present in the cancer cell and treating the cancer in the patient by administering a T cell therapy to the patient in an amount effective to treat cancer in the patient when the mutation in the one or more polypeptides is not present in the cancer cell. Preferably, the method comprises treating the cancer in the patient by administering a T cell therapy to the patient in an amount effective to treat cancer in the patient when the mutation in the polypeptides encoded by all of the genes set forth in Table I is not present in the cancer cell.

The cancer cell with the mutation in one or both of the gene and the polypeptide encoded by the gene may be more resistant to T cell-mediated cytolysis as compared to a control cell which is identical to the cancer cell except that it lacks the mutation. In this regard, the mutation confers resistance to T cell-mediated cytolysis to the cancer cell. The term "T cell-mediated cytolysis" refers in general to the cytolysis carried out by T cells, e.g., the mediation of the targeted destruction of cells by T cells. In the context of the present invention, the term typically refers to the capacity of T cells to kill cancer cells, e.g. via cytotoxic T cell activity. For example, in some embodiments, T cell-mediated cytolysis may be determined by measuring the expression by T cells of one or more markers which mediate cytolysis, e.g., one or more of granzyme A, perforin, interferon (IFN) gamma, IL-2, and tumor necrosis factor alpha (TNF-α), granulocyte/monocyte colony stimulating factor (GM-CSF), IL-4, IL-5, IL-9, IL-10, IL-17, IL-22, PD-1, LAG-3, TIM-3, 4-1BB, OX40, and CD107a, upon co-culture with target cancer cells. Alternatively or additionally, T cell-mediated cytolysis may be determined using one or more of a chromium release assay and an apoptosis assay measuring target cell lysis.

Alternatively or additionally, the method may comprise measuring the level of expression of one or more genes set forth in Table I. In this regard, an embodiment of the invention provides a method of selecting a therapy for a cancer patient, the method comprising measuring a level of one or both of (i) mRNA and (ii) polypeptide expressed from one or more genes in a cancer cell from the patient, wherein the one or more genes is selected from the group consisting of PTCD2, TWF1, DEFB134, BBS1, SOX10, APLNR, CD58, COL17A1, CRKL, hsa-mir-101-2, hsa-mir-548s, MAD2L1, MLANA, PSMB5, RNPS1, RPL10A, RPL23, SRP54, TAF3, TAP1, TAP2, TAPBP, TBXAS1, GMIP, OTOA, LAIR1, CLEC1, GPSM3, TRAF1, JAK2, TAPBPL, ICAM1, LILRA1, LILRA3, STAT1, and HLA-F. The method further comprises measuring the level of one or both of (i) mRNA and (ii) polypeptide expressed from the same one or more genes in a noncancerous cell. The cancerous cell and the noncancerous cell may be as described herein with respect to other aspects of the invention. Measuring the level of one or both of (i) mRNA and (ii) polypeptide expressed may be as described herein with respect to other aspects of the invention.

The method may further comprise comparing the level of one or both of (i) mRNA and (ii) polypeptide measured in the cancer cell with the level of one or both of (i) mRNA and (ii) polypeptide, respectively, measured in the noncancerous cell.

The method may further comprise selecting the patient for a therapy which is not a T cell therapy when the level of one or both of (i) mRNA and (ii) polypeptide measured in the cancer cell is decreased as compared to the level of one or both of (i) mRNA and (ii) polypeptide, respectively, measured in the noncancerous cell and selecting the patient for a T cell therapy when the level of one or both of (i) mRNA and (ii) polypeptide measured in the cancer cell is not decreased as compared to the level of one or both of (i) mRNA and (ii) polypeptide, respectively, measured in the noncancerous cell. Preferably, the method comprises selecting the patient for a T cell therapy when the level of one or both of (i) mRNA and (ii) polypeptide encoded by all of the 36 genes listed in Table I is not decreased.

The amount of one or both of mRNA and polypeptide encoded by one or more genes set forth in Table I expressed by the cancer cell may be, for example, about 10% lower, about 20% lower, about 30% lower, about 40% lower, about 50% lower, about 60% lower, about 70% lower, about 80% lower, about 90% lower as compared to that expressed by the noncancerous cell. In an embodiment of the invention, the cancer cell exhibits no detectable expression of one or both of mRNA and polypeptide encoded by the gene. Methods of measuring the level of mRNA expression and the level of polypeptide expression may be as described herein with respect to other aspects of the invention.

The decrease in the level of one or both of (i) mRNA and (ii) polypeptide confers resistance to T cell-mediated cytolysis to the cancer cell. Resistance to T cell-mediated cytolysis may be as described herein with respect to other aspects of the invention.

Another embodiment of the invention provides a method of selecting a therapy for a cancer patient and treating cancer in the patient, the method comprising selecting a therapy for the cancer patient by measuring a level of one or both of (i) mRNA and (ii) polypeptide expressed from one or more genes in Table I as described herein with respect to other aspects of the invention.

The method further comprises treating the patient by administering a therapy which is not a T cell therapy to the patient in an amount effective to treat cancer in the patient when the level of one or both of (i) mRNA and (ii) polypeptide measured in the cancer cell is decreased as compared to the level of one or both of (i) mRNA and (ii) polypeptide, respectively, measured in the noncancerous cell and treating the patient by administering a T cell therapy to the patient in an amount effective to treat cancer in the patient when the level of one or both of (i) mRNA and (ii) polypeptide measured in the cancer cell is not decreased as compared to the level of one or both of (i) mRNA and (ii) polypeptide, respectively, measured in the noncancerous cell. Preferably, the method comprises administering a T cell therapy to the patient in an amount effective to treat cancer in the patient when the level of one or both of (i) mRNA and (ii) polypeptide encoded by all of the genes set forth in Table I measured in the cancer cell is not decreased as compared to the level of one or both of (i) mRNA and (ii) polypeptide, respectively, measured in the noncancerous cell.

The T cell therapy employed in the inventive methods is not limited and may comprise any therapy comprising one or both of (i) one or more T cells and (ii) one or more cells which have been modified to express a T cell receptor. The one or more cells which have been modified to express a T cell receptor may be a T cell prior to being modified to express a T cell receptor or may be a cell other than a T cell which has been modified to express a T cell receptor.

The T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, thymus, spleen, or other tissues or fluids. Cells can also be enriched for or purified. Preferably, the T cell is a human T cell. The T cell can be any type of T cell and can be of any developmental stage, including but not limited to, $CD4^+/CD8^+$ double positive T cells, $CD4^+$ helper T cells, e.g., Th1 and Th2 cells, $CD4^+$ T cells, $CD8^+$ T cells (e.g., cytotoxic T cells), tumor infiltrating cells (TILs), memory T cells, naïve T cells, and the like.

The therapy which is not a T cell therapy employed in the inventive methods is not limited and may include any therapy which does not comprise both of (i) one or more T cells and (ii) one or more cells which have been modified to express a T cell receptor. Examples of therapies which are not a T cell therapy include, but are not limited to, surgical resection, chemotherapy, radiotherapy, NK cell therapy, B cell therapy, gene therapy, anti-cancer vaccine therapy, targeted drug inhibitor therapy, or any combination thereof.

"Targeted drug inhibitor therapy" refers to therapies which employ an inhibitor of a cancer protein. An example of a targeted drug inhibitor therapy is vemurafenib, which targets mutated B-RAF. The term "cancer protein," as used herein, refers to any molecule (e.g., protein, polypeptide, peptide, lipid, carbohydrate, etc.) solely or predominantly expressed or over-expressed by a tumor cell or cancer cell, such that the protein is associated with the tumor or cancer. The cancer protein can additionally be expressed by normal, non-tumor, or non-cancerous cells. However, in such cases, the expression of the cancer protein by normal, non-tumor, or non-cancerous cells is not as robust as the expression by tumor or cancer cells. In this regard, the tumor or cancer cells can over-express the protein or express the protein at a significantly higher level, as compared to the expression of the protein by normal, non-tumor, or non-cancerous cells. Also, the cancer protein can additionally be expressed by cells of a different state of development or maturation. For instance, the cancer protein can be additionally expressed by cells of the embryonic or fetal stage, which cells are not normally found in an adult host. Alternatively, the cancer protein can be additionally expressed by stem cells or precursor cells, which cells are not normally found in an adult host. Cancer proteins are known in the art and include, for instance, mesothelin, CD19, CD22, CD276 (B7H3), gp100, MART-1, Epidermal Growth Factor Receptor Variant III (EGFRVIII), TRP-1, TRP-2, tyrosinase, NY-ESO-1 (also known as CAG-3), MAGE-1, MAGE-3, etc.

Another embodiment of the invention provides a method of screening for one or more genes, the mutation of which confers resistance to T cell-mediated cytolytic activity. The inventive screening method may provide advantages over in vitro single cell-type screens or in vivo screens including, for example, any one or more of (1) the providing of information about how genetic manipulations in one cell type can affect a complex interaction between cell types; (2) the ability to perform the pooled screen with a much higher library representation than can typically be achieved in vivo; and (3) the ability to identify genes and pathways which may not be detected by in vitro single cell-type screens or the uncontrolled environment of in vivo screens.

The inventive screening method may employ the CRISPR/Cas system. The CRISPR/Cas system is described at, for example, Cheng et al., *Cell Res.*, 23: 1163-71 (2013). Briefly, the CRISPR/Cas system involves creating specific double-stranded breaks (DSBs) at targeted locations in the genome using the Cas endonuclease. Endogenous mechanisms in the cell are used to repair the induced break by homologous recombination (HR) and nonhomologous end-joining (NHEJ). The CRISPR/Cas system may be used to knockout expression of a gene of interest.

Accordingly, the inventive method may comprise introducing a nucleic acid encoding a Cas endonuclease and a nucleic acid encoding a single guide RNA (sgRNA) molecule into a target cell, wherein the sgRNA hybridizes to a test gene in the target cell, and forming a complex between the sgRNA and Cas endonuclease so that the Cas endonuclease introduces a double strand break in the test gene. Non-limiting examples of Cas endonucleases include Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, and Csx17. Preferably, the Cas endonuclease is Cas9. Preferably, the sgRNA specifically hybridizes to the test gene such that the sgRNA hybridizes to the test gene and does not hybridize to any other gene that is not the test gene.

The method may further comprise deleting all or a portion of the test gene to decrease expression of the test gene. The expression of the test gene may be decreased by any amount, for example, by about 10%, about 20%, about 30%, about 40%, about 50%, about 60%, about 70%, about 80%, or about 90%. Preferably, expression of the test gene is decreased so that there is no detectable expression of the test gene.

The method may further comprise co-culturing the target cell having decreased expression of the test gene with an effector cell and co-culturing a negative control cell with the effector cell, wherein the negative control cell is identical to the target cell except that it does not comprise the nucleic acid encoding a Cas endonuclease and the nucleic acid encoding a single guide RNA (sgRNA) molecule and does not have decreased expression of the test gene. The co-culture may be carried out in any suitable manner known in the art that facilitates interaction of the target cell with the effector cell. For example, the co-culture may comprise culturing the target cell and the effector cell so that they are in direct physical contact with one another.

The method may further comprise measuring a level of lysis of the target cell by the effector cell and measuring a level of lysis of the negative control cell by the effector cell. The level of lysis may be determined by any suitable manner known in the art. For example, when the effector cell is a T cell, measuring the level of lysis may be carried out by measuring the expression by the T cells of one or more markers which mediate cytolysis, as described herein with respect to other aspects of the invention.

The method may further comprise comparing the level of lysis of the target cell to the level of lysis of the negative control cell. A decrease in the level of lysis of the target cell as compared to the level of lysis of the negative control cell indicates that mutation of the test gene confers resistance to T cell-mediated cytolytic activity to the target cell. A lack of a decrease in the level of lysis of the target cell as compared to the level of lysis of the negative control cell indicates that mutation of the test gene does not confer resistance to T cell-mediated cytolytic activity to the target cell. The mutation may be as described herein with respect to other aspects of the invention.

The decrease in the level of lysis of the target cell as compared to the level of lysis of the negative control cell may be a decrease of any amount. For example, the decrease in the level of lysis of the target cell may be a decrease of about 10%, about 20%, about 30%, about 40%, about 50%, about 60%, about 70%, about 80%, about 90% as compared to the level of lysis of the negative control cell.

The test gene may be any gene of interest. The test gene may be any gene which is suspected or known to be involved in the interaction of the target cell with the effector cell. In an embodiment of the invention, the test gene is any one of the genes set forth in Table I.

The target cell may be any cell of interest. The target cell may be any cell which is suspected or known to interact with the effector cell. In an embodiment of the invention, the target cell is a cancer cell. The cancer cell may be as described herein with respect to other aspects of the invention.

The effector cell may be any effector cell of interest. In an embodiment of the invention, the effector cell is a T cell. In another embodiment of the invention, the cell is a cell which has been modified to express a T cell receptor. The T cell, and the cell which has been modified to express a T cell receptor, may be as described herein with respect to other aspects of the invention.

The cancer may be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In certain preferred embodiments, the cancer is melanoma.

The term "treat," as well as words stemming therefrom, as used herein, does not necessarily imply 100% or complete treatment. Rather, there are varying degrees of treatment of which one of ordinary skill in the art recognizes as having a potential benefit or therapeutic effect. In this respect, the inventive methods can provide any amount of any level of treatment of cancer in a patient. Furthermore, the treatment provided by the inventive method can include treatment of one or more conditions or symptoms of the cancer being treated. For example, treatment can include promoting the regression of a tumor.

The following examples further illustrate the invention but, of course, should not be construed as in any way limiting its scope.

EXAMPLES

The following materials and methods were employed in the experiments described in Examples 1-4.

Patient Peripheral Blood Mononuclear Cells and Cell Lines

All peripheral blood mononuclear cell (PBMC) samples were derived from patients with melanoma or healthy donors with consents and procedures approved by the institutional-review board (IRB) of the National Cancer Institute (NCI).

The melanoma cell lines HLA-A2$^+$/MART-1$^+$/NY-ESO-1$^+$ (Mel624.38, Mel1300), HLA-A2$^-$ (Mel938) and HLA-A2$^+$/NY-ESO-1$^-$ (Mel526) were isolated from surgically resected metastases as described (Johnson et al., J. Immunol., 177: 6548-6559 (2006)) and were cultured in RPMI 1640 (Invitrogen, Carlsbad, Calif.) medium supplemented with 10% fetal bovine serum (FBS, Hyclone, Logan, Utah). The A375 (HLA-A2$^+$/NY-ESO-1+) and SK23 (NY-ESO-1$^-$) cell lines were obtained from the American Type Culture Collection (Manassas, Va.). The SK23 cell-line transduced with retrovirus containing NY-ESO-1 expressing vector (SK23 NY-ESO-1+) was obtained from Ken-ichi Hanada (NCI). All melanoma cell lines were cultured in D10 medium containing DMEM supplemented 10% FBS, 2 mM L-glutamine, and 1% penicillin-streptomycin.

All PBMCs and lymphocytes used for transduction and as feeder cells were obtained from aphereses of NCI Surgery Branch patients on IRB-approved protocols. They were cultured in T cell medium, which is: AIM-V medium (Invitrogen) supplemented with 5% human AB serum (Valley Biomedical, Winchester, Va.), 100 U/ml penicillin and 100 µg/ml streptomycin, 2 mM L-glutamine and 12.5 mM HEPES (Life Technologies).

Retroviral Vectors and Transduction of Human T Cells

Retroviral vectors for TCRs recognizing the HLA-A*02-restricted melanoma antigens NY-ESO-1 (NY-ESO-1:157-165 epitope) and MART-1 (MART-1:27-35 epitope, DMFS) were generated as previously described (Johnson et al., J. Immunol., 177: 6548-6559 (2006); Robbins et al., J. Immunol., 180: 6116-6131 (2008)). Clinical grade cGMP-quality retroviral supernatants were produced by the National Gene Vector Laboratories at Indiana University. For virus titer determinations, peripheral blood lymphocytes (PBLs) (2×10$^6$ cell/mL) were stimulated with IL-2 (300 IU/mL) and anti-CD3 antibody OKT3 (300 IU/mL) on Day 0. Non-tissue culture treated six-well plates were coated with 2 mL/well of 10 µg/mL RetroNectin (Takara Bio, Otsu, Japan) on day 1 and stored overnight at 4° C. Serial dilutions of vector supernatant (4 mL/well, diluted with D10 media) were applied to plates on day 2 followed by centrifugation at 2000×g for 2 h at 32° C. Half the volume was aspirated and PBLs were added (0.25-0.5×10$^6$ cell/mL, 4 mL/well), centrifuged for 10 min at 1000×g, and incubated at 37° C./5% $CO_2$. Vector titers were calculated as follows: [(% tetramer positive cells×total cell number×dilution factor)] ÷supernatant volume. A second transduction on day 3 was performed as described above. Cells were maintained in culture at 0.7-1.0×10$^6$ cell/mL. After harvest, cells underwent a rapid expansion protocol (REP) in the presence of soluble OKT3 (300 IU/mL), IL-2 (6000 IU/mL) and irradiated feeders as previously described (Johnson et al., J. Immunol., 177: 6548-6559 (2006)). After day 5 of the REP, cells were maintained in culture at 0.7-1.0×10$^6$ cell/mL until harvested for testing on day 7-10 or frozen down for co-culture later.

Lentivirus Production and Purification

To generate lentivirus, HEK293FT cells (Invitrogen) were cultured in D10 medium. One day prior to transfection, HEK293FT cells were seeded in T-225 flasks at 60% confluency. One to two hours before transfection, DMEM media was replaced with 13 mL of pre-warmed serum-free OptiMEM media (Invitrogen). Cells were transfected using LIPOFECTAMINE 2000 reagent and PLUS reagent (Invitrogen). For each flask, 4 mL of OptiMEM was mixed with 200 μL of PLUS reagent, 20 μg of LENTICRISPRV2 plasmid or pooled plasmid human GeCKOv2 (Genome-scale CRISPR Knock-Out) library, 15 μg psPAX2 (Addgene, Cambridge, Mass.) and 10 μg pMD2.G (Addgene). 100 uL LIPOFECTAMINE 2000 reagent was diluted with 4 mL of OPTIMEM medium and was combined to the mixture of plasmids and PLUS reagent. This transfection mixture was incubated for 20 minutes and then added dropwise to the cells. 6-8 h post transfection, the media was replaced to 20 mL of DMEM supplemented with 10% FBS and 1% BSA (Sigma). Virus containing media was harvested 48 h post-transfection. The sufficiency of viral titers was confirmed with LENTI-X GOSTIX test (Clontech, Mountain View, Calif.). Cell debris were removed by centrifugation of media at 3,000 rcf and 4° C. for 10 minutes followed by filtration of the supernatant through a 0.45 μm low-protein binding membrane (Millipore Steriflip HV/PVDF). For individual LENTICRISPRV2 plasmids, viral supernatants were frozen in aliquots at −80° C. For pooled library plasmids, viral supernatants were concentrated by centrifugation at 4,000 rcf and 4° C. for 35 min in AMICON ULTRA-15 filters (Millipore Ultracel-100K). Concentrated viral supernatants were stored in aliquots at −80° C.

Development of Two Cell-Type (2CT) CRISPR Assay

To devise a 2CT (T cell: tumor cell) assay system (FIG. 1A), melanoma patient-derived T cells retrovirally transduced with T cell receptors (TCRs) recognizing the HLA-A*02-restricted melanoma antigen NY-ESO-1 (NY-ESO1: 157-165 epitope) (NY-ESO-1T cells) and a heterogeneous melanoma cell line (Mel624) were used with the goal of achieving TCR-specific cytolysis under co-culture conditions. It is of clinical interest to identify genes which confer sensitivity to T cell cytolytic activity to cancer cells that are not restricted to specific antigen and TCR avidity. With this in mind, patient-derived Mel624 cells (Mel624$^{WT}$) which express both NY-ESO-1 and MART-1 antigens in an HLA-A*02-restricted manner were selected allowing targeting of these cells with either low-avidity NY-ESO-1 T cells or high-avidity MART-1 T cells during co-culture experiments.

To minimize the effect of alloreactivity and bystander cell lysis exhibited by T cells in this assay system, the selection pressure of T cells was reduced by modulating the length of co-incubation time and E:T ratios such that ~20% of cells survived after 24 hours of co-culture at an E:T ratio of 0.5. To ensure NY-ESO-1 and HLA-A*02-specific reactivity of NY-ESO-1 T cells, gamma-interferon (IFNγ) release was measured with control cell-lines (Table 1), and cell survival post co-incubation of NY-ESO-1 T cells with non-NY-ESO-1 expressing SK23 and NY-ESO-1 expressing SK23 and Mel624 cells (FIG. 1B). β2M (encoded by B2M) is unregulated on tumor cells upon interaction with T cells in an IFNγ dependent manner. It was found that after co-incubation in as little as 6 hours, tumor cells interact sufficiently with T cells to achieve an increase in β2M expression. Collectively, with these experiments, the selection pressure, specificity and duration of co-incubation in the 2CT assay system were designed.

TABLE 1

| | | Melanoma Cell Line | | | |
|---|---|---|---|---|---|
| | | HLA-A2− ESO+ | HLA-A2+ ESO− | HLA-A2+ ESO+ | |
| | | None | Mel938 | Mel526 | Mel624 | Mel1300 |
| Patient1 | PBMC | 2 | 26 | 1 | 15 | 60 |
| | ESO TCR Td | 3 | 31 | 0 | 1168 | >1200 |
| Patient2 | PBMC | | 3 | 4 | 12 | 13 |
| | ESO TCR Td | 13 | 241 | 89 | >1200 | >1200 |
| Patient3 | PBMC | 6 | 13 | 12 | 15 | 8 |
| | ESO TCR Td | 7 | 11 | 47 | >950 | >950 |

GeCKOv2 Library Transduction

Mel624 cells were transduced with the human GeCKOv2 library virus using spinfection. To determine the functional titer and achieve a target MOI (multiplicity of infection) of 0.3-0.4, a test transduction was carried out. Specifically, Mel624 cells were infected in 12-well plate format with different viral volumes (10, 30, 50, 100 and 150 μL) of each library in D10 media supplemented with 6 μg/mL polybrene (Sigma-Aldrich, Saint Louis, Mo.). Spinfection was carried out by centrifugation at 1,000 rcf for 1 h at 30° C. Twenty-four hour post spinfection, infected cells were reseeded into 2 wells of a 12-well plate each with D10 media; one well was supplemented with 1 μg/ml puromycin. Cells were counted at day 5 post-selection to calculate the infection efficiency by comparing survival with and without puromycin selection. The highest viral volume yielding an MOI <0.4 was used for large-scale screening.

Screening scale spinfection was performed with enough Mel624 cells in 12-well plate format to achieve minimum representation of ~300 cells per sgRNA in the library. Cells were trypsinized 12 hours after spinfection and seeded in T-flasks. Twenty-four hours post-spinfection, cells were selected with 1 μg/mL puromycin for 5-7 days to eliminate uninfected cells.

Two Cell-Type (2CT) T Cell and Tumor Cell Co-Culture Assay

NY-ESO-1 and MART-1 T cells were used for co-culture assays. Two days prior to co-culture, cells were thawed in T cell media containing 3 U/mL DNAse (Genentech Inc., South San Francisco, Calif.) overnight. Tumor cells were seeded at a specific density on this day in the same media as the T cells. T cells were then cultured in T cell media containing 300 IU/mL interleukin-2 (IL2) for 24 hours. T cells were co-cultured with tumor cells at various Effector: Target (E:T ratios) for varying time periods. To reduce T cell killing activity and enrich for resistant tumor cells during the recovery phase, T cells were removed by careful 2× phosphate buffered saline (PBS) washes following the addition of D10 media without IL2. At the end of recovery phase of co-culture, tumor cells were detached using trypsin (Invitrogen) and washed twice with PBS. Tumor cells were then stained with fixable LIVE/DEAD dye (Invitrogen) followed by human anti-CD3 antibody (SK7, BD) in FACS staining buffer (PBS+0.2% BSA). Cell counts were measured using COUNTBRIGHT Absolute Counting Beads (Invitrogen) by flow cytometry.

2CT GeCKOv2 Screens and Genomic DNA Extractions

Cell-cell interaction genome-wide screens were performed using Mel624 cells transduced independently with both A and B GeCKOv2 libraries. In the initial screen, two sets of $5\times10^7$ transduced Mel624 cells were split. Cells from one set were co-cultured with $1.67\times10^7$ patient-derived NY-ESO-1 T cells (E:T ratio of 1:3) for each library. Tumor cells from another set were used as controls, which were cultured under the same density and conditions, but without T cells. The co-culture phase was maintained for 12 hours after which the T cells were removed as described above. The recovery phase was maintained for another 48 hours. Cells from co-culture flasks and from control flasks were harvested for genomic DNA (gDNA) extraction. In this initial screen, NY-ESO-1 T cells lysed ~76% of tumor cells, and the surviving cells were frozen to evaluate sgRNA enrichment later. This was termed the low selection pressure (LoSelect) screen. In the second screen, again two sets of $5\times10^7$ transduced Mel624 cells were provided. For one set, the E:T ratio was increased to 1:2 by co-culture of $2.5\times10^7$ NY-ESO-1 T cells with $5\times10^7$ transduced Mel624 cells for each library while keeping all other conditions similar. As before, the second set of Mel624 cells were used as controls, which were cultured under the same density and conditions, but without T cells. By increasing the selection pressure, it was observed that T cells killed ~90% of Mel624 cells. Therefore, this was termed the high selection pressure (HiSelect) screen. To evaluate sgRNA enrichment in surviving resistant tumor cells, cells were harvested and frozen.

For gDNA extraction from harvested tumor cells (minimum $3\times10^7$ control cells), frozen cell pellets were thawed. An ammonium acetate and alcohol precipitation procedure was used to isolate gDNA as previously described (Chen et al., Cell, 160: 1246-1260 (2015)). The first step of extraction protocol was modified to use AL buffer (Qiagen) for cell lysis.

Pooled Screen Readout and Data Analysis

To determine sgRNA abundance as the readout of library screens, two-step PCR amplifications were performed on gDNA using TAKARA EX-TAQ polymerase (Clontech). The first PCR step (PCR1) included amplification of the region containing sgRNA cassette using v2Adaptor_F and v2Adaptor_R primers, and the second step PCR (PCR2) included amplification using uniquely barcoded P7 and P5 adaptor-containing primers to allow multiplexing of samples in a single HISEQ run. All PCR1 and PCR2 primer sequences, including full barcodes, are listed on the GeCKO website (genome-engineering.org/gecko/). Assuming 6.6 µg of gDNA per cell, 150 µg of gDNA was used per sample (>300 cells per library sgRNA representation), and 15 PCR1 reactions were performed for each biological sample. Ten µg gDNA were used as input in each 100 uL PCR1 reaction performed under cycling conditions: 95° C. for 5 min, 18 cycles of (95° C. for 30 s, 62° C. for 30 s, 72° C. for 30 s), and 72° C. for 3 min. PCR1 products for each sample were pooled and used for amplification with barcoded second step PCR primers. Seven PCR2 reactions were performed using 5 µL of the pooled PCR1 product per PCR2 reaction. Second PCR products were pooled and then normalized for each biological sample before combining uniquely-barcoded separate biological samples. The pooled product was then gel-purified from a 2% E-GEL EX (Life Technologies, Carlsbad, Calif.) using the QIAQUICK kit (Qiagen, Hilden, Germany). The purified, pooled library was then quantified with TAPESTATION 4200 instrument (Agilent Technologies, Santa Clara, Calif.). Diluted libraries with 5%-20% PhiX were sequenced with HISEQ 2000 system.

Sequencing reads were demultiplexed using custom LINUX shell scripts, allowing for a maximum of 1 mismatch in either forward or reverse barcodes. Demultiplexed reads were trimmed by CUTADAPT tool using 12 bp flanking sequences around the 20 bp guide sequence (Martin, *EMBnet J.*, 17 (2011)). Trimmed reads were aligned using BOWTIE aligner (Langmead et al., *Genome Biol.*, 10: 1-10 (2009)) to the GeCKOv2 indexes created from library CSV files downloaded from the GeCKO website (genome-engineering.org/gecko/?page_id=15). Read alignment was performed with parameters −m 1 −v 1 −norc, which allows up to 1 mismatch and discards any reads that do not align in the forward orientation or that have multiple possible alignments. Aligned counts of library sgRNAs were imported into R/RStudio. Counts were first normalized by the total reads for each sample and then log-transformed. A gene ranking was computed using the second most enriched sgRNA for each gene. This ranking is robust to outlier/off-target effects that enrich/deplete a single sgRNA by requiring at least 2 enriched sgRNAs targeting the same gene.

Validation lentiCRISPR Array Screen

Individual lentiCRISPRs were produced as above except that viral supernatants were not concentrated. For each gene, 3-4 sgRNA guide sequences were used, where 2 sgRNAs sequences were designed de novo and other 2 sgRNAs were from GeCKOv2 library. These sgRNAs were cloned into the lentiCRISPRv2 vector (Addgene) as previously described (FIG. 9). To produce virus in a high-throughput format, HEK293FT cells were seeded and transfected in 6-well plates where each well received a different lentiCRISPR plasmid. The lentiviral production protocol was the same as the one described above for GeCKOv2 library lentivirus production.

Mel624 and A375 cells with unique gene perturbation were generated using these viral supernatants. Typically, 500 ul of lentiCRISPRv2 virus per 5×10⁴ cells for Mel624 and A375 was used. Puromycin selection was applied to these cells for 5-7 days, which is the time period needed to completely kill an untransduced control for both Mel624 and A375.

Cells were split and one half were frozen for analysis of insertion-deletion (indel) mutations after non-homologous end-joining repair and the remainder were normalized to seed 1×10⁴ cells/well in 96-well plates. During the arrayed screen, each cell line was co-cultured with appropriate T cells (either NY-ESO-1 or MART-1) in a 96-well plate format at an E:T ratio of 1:3 for 12 hours in T cell media. As in the pooled screen, gentle 2×PBS washes were performed to remove the T cells. Mel624 or A375 cells were collected after a recovery phase culture of 48 hours for high-throughput flow cytometry analysis. Tumor cell counts were measured using a FACS-based COUNTBRIGHT bead method. Variability was noticed in proliferation and survival rates across cells depending on the sgRNA received. To account for this variability, a relative percent change was calculated for each sgRNA: (% Δ 2CT vs noT) in tumor cells co-cultured with T cells (2CT) compared to tumor cell counts without T cells (noT). The normalized resistance was calculated by the following formula:

$$\text{Normalized Resistance} = \frac{(\%\ \Delta\ 2CT\ vs\ noT)\text{gene-targeting }sgRNA}{(\%\ \Delta\ 2CT\ vs\ noT)\text{non-targeting }sgRNA}$$

For co-culture with MART-1 T cells, all parameters were the same, except that the co-culture period duration was 24 hours with the same recovery period as with NY-ESO-1 experiments.

Indel Mutation Detection for Array 2CT Validation

Frozen cell pellets were thawed for genomic DNA extractions. DNA was extracted with a Blood & Cell Culture MIDI kit (Qiagen). SgRNA target site PCR amplifications were performed for each genomic loci using conditions as described (Chen et al., *Cell*, 160: 1246-1260 (2015)), pooled together and then sequenced in a single ILLUMINA MISEQ. All primer sequences for indel detection can be found in Table A.

TABLE A

| sgRNA_Name | Forward primer (5'-3') | Reverse primer (5'-3') |
| --- | --- | --- |
| APLNR_sgRNA_1 | TCTGGACCGTGTTTCGGAG (SEQ ID NO: 65) | ACGCTGGCGTACATGTTGA (SEQ ID NO: 82) |
| APLNR_sgRNA_3 | CACTGGCCCTGTGACTTTGA (SEQ ID NO: 66) | GTAGCTGGCTGACTTCTCCC (SEQ ID NO: 83) |
| BBS1_sgRNA_2 | AGAGGGTCAGTGGAGAGGTC (SEQ ID NO: 67) | CTCCATGAGGAAGGTGGCAG (SEQ ID NO: 84) |
| BBS1_sgRNA_4 | AGCCTGGACTTGTACCCAGA (SEQ ID NO: 68) | GGACCATTGTCTGACTCCCC (SEQ ID NO: 85) |
| CD58_sgRNA_1 | CGTAGGCGGTGCTTGAACTTA (SEQ ID NO: 69) | CGTCTCTGATCGGCAACCG (SEQ ID NO: 86) |
| CD58_sgRNA_2 | CTACTTCTGGCCGACCGC (SEQ ID NO: 70) | ACCCGTCTCTGATCGGCAA (SEQ ID NO: 87) |
| CD58_sgRNA_3 | CATGTACCAAGCAATGTGCCTTTA (SEQ ID NO: 71) | TGGAATACTCACCAAGCACATA (SEQ ID NO: 88) |
| COL17A1_sgRNA_1 | AGTTTGATTCCTGGAGGCAG (SEQ ID NO: 72) | CCTGGTTTGAGGTTTTGAAGGA (SEQ ID NO: 89) |
| COL17A1_sgRNA_2 | ATCCAGAGGTGTCAGTGCATTA (SEQ ID NO: 73) | AGCTCCCATGGAAAAGGTTACAG (SEQ ID NO: 90) |
| MLANA_sgRNA_1 | GTGCCCTGACCCTACAAGATG (SEQ ID NO: 74) | AGGCATGTACTGGTGGAAGTC (SEQ ID NO: 91) |
| MLANA_sgRNA_2 | GTGCCCTGACCCTACAAGATG (SEQ ID NO: 75) | AGGCATGTACTGGTGGAAGTC (SEQ ID NO: 92) |
| RPL23_sgRNA_1 | CATGTGCGGTGAATTACAGCTT (SEQ ID NO: 76) | TTCACTCTCCCCTTTCTTGACG (SEQ ID NO: 93) |
| RPL23_sgRNA_3 | CATGTGCGGTGAATTACAGCTT (SEQ ID NO: 77) | TTCACTCTCCCCTTTCTTGACG (SEQ ID NO: 94) |
| SOX10_sgRNA_3 | AATCATAGGGCACAGCCCCC (SEQ ID NO: 78) | TACTTGTAGTCCGGGTGGTCT (SEQ ID NO: 95) |
| TAPBP_sgRNA_3 | TGAAGTTCCCCGAACGCTG (SEQ ID NO: 79) | AAGAGGCTGGAGAGGCTGAG (SEQ ID NO: 96) |
| TAPBP_sgRNA_4 | CACCAGACATACAAACCGCTC (SEQ ID NO: 80) | ACTGAGATAGAGCTCAGGGTCG (SEQ ID NO: 97) |

TABLE A -continued

| sgRNA_Name | Forward primer (5'-3') | Reverse primer (5'-3') |
|---|---|---|
| CTAG1B_sgRNA_1 | AACTTCCTGCAGCCTCTCTG (SEQ ID NO: 81) | CCCTGGGCCATCAGGAATG (SEQ ID NO: 98) |

To analyze the data from the MISEQ run, paired-end reads were trimmed for quality using trimmomatic with parameters SLIDINGWINDOW: 5: 25 (Bolger et al., *Bioinformatics*, (2014)). Reads with surviving mate pairs were then aligned to their targeted amplicon sequence using Bowtie2 (Langmead et al., *Nat. Meth.*, 9: 357-59 (2012)). To determine indel sizes, the size difference between observed reads and predicted read size based on the genomic reference sequence was calculated. If observed read size was equal to the predicted size, these reads were scored as no indels. The size difference was used to detect insertions or deletions.

Flow Cytometry and Interferon Gamma Enzyme-Linked Immunosorbent Assay (ELISA)

Tumor cells or T cells suspended in FACS staining buffer were stained with fluorochrome-conjugated antibodies against combinations of the following surface human antigens: CD4 (RPA-T4, BD, Franklin Lakes, N.J.), CD8 (SK1, BD), CD3e (SK7, BD), HLA-A2/MART-1:27-35 tetramer (DMFS, Beckman Coulter Immunotech, Monrovia, Calif.); NY-ESO-1 tetramer (NIH Tetramer Core Facility); PD1-L1 (MIH1, eBiosciences, San Diego, Calif.); PD1-L2 (24F.10C12, Biolegend, San Diego, Calif.); beta-Galectin (9M1-3, Biolegend), CD58 (1C3, BD) and b2M (2M2, Biolegend). Cell viability was determined using propidium iodide exclusion or fixable live/dead (Invitrogen). Flow cytometric data were acquired using either a FACSCANTO II or LSRII FORTESSA cytometer (BD), and data were analyzed with FLOWJO version 7.5 software (FlowJo LLC, Ashland, Oreg.). The amount of IFNγ release by T cells after co-culture with tumor cells was measured by Sandwich ELISA assay using anti-IFNγ (Thermo Scientific M700A) coated 96-well plates, biotin-labeled anti-IFNγ (M701B), HRP-conjugated streptavidin (N100) and TMB substrate solution (N301).

Western Blot Analysis

Total protein was extracted with ix RIPA lysis buffer (Millipore, Billerica, Mass.) with ix protease inhibitor (Roche, Basel, Switzerland). Protein concentration was determined using the BCA assay (Thermo/Pierce). Cell lysates were resolved on 4-20% Tris-Glycine gels (Invitrogen), transferred to PVDF membranes (Millipore), and incubated overnight at 4° C. with the appropriate primary antibodies: Anti-APLNR (1:500, Santa Cruz Biotechnology H-300 sc-33823), Anti-BBS1 (1:500, Santa Cruz Biotechnology F-1 sc-365138), Anti-SOX10 (1:1000, Cell Signaling D5V9L 89356) and Anti-BETA ACTIN (1:1000, Santa Cruz Biotechnology C4 sc-47778). Signals were detected using HRP-conjugated secondary antibodies (Santa Cruz Biotechnology) and SUPERSIGNAL WEST FEMTO Chemiluminescent Substrate (Thermo/Pierce). Images were captured using CHEMIDOC TOUCH imaging system (Bio-Rad, Hercules, Calif.).

Analysis of CTLA4 blockade human dataset

RNAseq data were obtained from published work by Van Allen et al. (Levi Garraway group) and Reads Per Kilobase of transcript per Million mapped reads (RPKM) values were calculated with the same filters and criteria as described (Van Allen et al., *Science*, 350: 207-211 (2015)). For each of the genes explored, expression levels were divided into quartiles and the resulting categories were used to determine if there was an association between the expression level and overall survival (OS). The probability of OS as a function of time was estimated by the Kaplan-Meier method, and the statistical significance of the difference among curves was determined by the log-rank test. When the initial analysis of Kaplan-Meier curves suggested that there could be a difference between two pooled sets of categories, the resulting division into two groups was made and the significance was reported using an adjusted p-value equal to three times the unadjusted p-value to account for the number of implicit tests done to arrive at the final grouping. Those genes whose expression levels were potentially associated with OS with unadjusted p-values <0.10 by univariate analyses were evaluated for their joint significance using Cox proportional hazards models.

Pathway Analysis

For pathway analysis, all genes in the genome-scale CRISPR pooled screen with a second-best sgRNA score above the FDR threshold (log 2(enrichment) >0.5) were first identified. This yielded a list of 554 genes. In this list, gene category over-representation was looked for using Ingenuity Pathway Analysis (QIAGEN Redwood City, qiagen.com/ingenuity). The analysis criteria were set as follows: 1) querying for molecules with Ingenuity Knowledge Base as a reference set, 2) restricted to human species, and 3) experimentally observed findings as a confidence level. Fisher's Exact Test (p<0.05) was used to compute significance for over-representation of genes in a particular pathway/biological process.

The Cancer Genome Atlas (TCGA) Data Analyses

TCGA RNA-seq data from multiple cancer data sets was downloaded from the Firehose Broad GDAC (gdac.broadinstitute.org/, DOI for data release: 10.7908/C11G0KM9) using the TCGA2STAT package for R (Wan et al., *Bioinformatics*, 32: 952-54 (2016)) and used to find overlap between TCGA gene expression indicative of cytolytic activity and genes from the pooled screen where loss-of-function create resistance to T cell killing.

The genes correlated with a previously identified cytolytic activity signature, namely expression of granzyme A (GZMA) and perforin 1 (PRF1) were first identified (Rooney et al., *Cell*, 160: 48-61 (2015)). To identify these genes in the TCGA data, the geometric mean of GZMA and PRF1 was calculated in each data set and any genes with a positive correlation to this quantity across patients were searched for (Pearson's r>0, p<0.05).

The intersection between genes whose expression was correlated with cytolytic activity (TCGA datasets) and the enriched genes found the CRISPR screen (cutoff >0.5 on second most enriched guide score, 554 genes) was then examined. This method resulted in the genes correlated with CYT in many cancers, which formed Cluster 1 and Cluster 2. Individual heatmaps for the two sets of clustered genes were regenerated for each cancer type.

Statistical Analyses

Data between two groups were compared using a two-tailed unpaired Student's t test or the Mann-Whitney test as appropriate for the type of data (depending on normality of the distribution). Unless otherwise indicated, a P value less than or equal to 0.05 was considered statistically significant for all analyses, and not corrected for multiple comparisons. To compare multiple groups, an analysis of variance (ANOVA) with the Bonferroni correction was used. Prism (GraphPad Software Inc., La Jolla, Calif.) was used for these analyses.

Example 1

This example demonstrates that CRISPR-Cas9 mediated perturbation of genes in cancer cells resist engineered T-cell mediated lysis.

To identify the genes which confer sensitivity to T cell-mediated cytolysis to tumor cells, a 'two cell-type' (2CT) CRISPR assay system including human T cells as effectors and tumor cells as targets was developed (FIG. 1A). Unlike in vitro single cell-type screens or in vivo screens, the 2CT system uniquely allows one to: 1) understand how genetic manipulations in one cell type can affect a complex interaction between cell types; 2) perform the pooled screen with much higher library representation than cannot typically be achieved in vivo; and 3) identify novel genes and pathways which may not be detected by in vitro single cell-type screens or the uncontrolled environment of in vivo screens.

To develop the 2CT assay, T cell receptor (TCR) engineered human T cells that can specifically recognize and lyse melanoma cells expressing NY-ESO-1 antigen (NY-ESO1: 157-165 epitope) in an HLA-A*02-restricted fashion (ESO T cells) were utilized (FIG. 1B and Table 1) (Robbins et al., J. Immunol., 180: 6116-131 (2008); Johnson et al., J. Immunol., 177: 6548-59 (2006)). The 2CT assay was designed to control selection pressure, alloreactivity and bystander killing (Spiotto et al., 10: 294-298 (2004)) exerted by T cells via modulation of effector to target (E:T) ratio and length of co-incubation (Table 1 and FIGS. 5A-5D). A FACS-based determination of live, PI (propidium iodine)-negative CD3$^-$ tumor cell counts after co-culture of patient ESO T cells with Mel624 cells at an E:T ratio of 100 for 24 hr was carried out. The percentages of CD3-/PI- cells measured was as follows: DMEM (89.7) (control), Tcell media (92.2) (control), Patient 1 (1.3), Patient 2 (1.9), and Patient 3 (3.6).

To test whether the loss of antigen presentation genes can directly compromise T cell-mediated cell lysis of human cancer cells using the 2CT CRISPR assay, LMP2, TAP2 and B2M known to be involved in MHC-I dependent antigen presentation were targeted (Neefjes et al., Nat. Rev., Imunol., 11: 823-36 (2011)). Three unique single guide RNAs (sgRNAs) for each of these three genes were designed and cloned into a lentiviral CRISPR vector (lentiCRISPRv2), and NY-ESO-1$^+$Mel624 cells were transduced at a low multiplicity of infection (MOI=0.5). FACS analysis confirmed that B2M targeting lentiviral CRISPRs were able to achieve at least 95% allele modifications in these cells (FIG. 1C). Upon co-culture of the gene modified NY-ESO-1+Mel624 cells with ESO T cells, significant cytolysis resistance was detected in cells transduced with B2M sgRNAs (72±5%) and with TAP2 sgRNAs (13±2%) (FIGS. 1D and 1E). These results suggest that the dynamic range (FIG. 1E) of the 2CT assay platform was sufficient to perform a positive selection screen.

Example 2

This example demonstrates that a 2CT GeCKOv2 screen in Mel624 melanoma cells identifies genes that confer resistance to T cell-mediated cytolysis.

To identify the tumor intrinsic genes which confer sensitivity to T cell mediated cytolysis to cancer cells, a Genome-Scale CRISPR Knock-Out (GeCKO) screen was performed using the 2CT assay platform with different ratios of T cells to tumor cells (FIG. 2A). Specifically, transduced Mel624 cells were exposed to ESO T cells at E:T ratios that resulted in less than complete T cell-mediated tumor cell death after a 12 hour exposure (FIG. 5B). These screens with different E:T ratios were termed as 'LoSelect' (E:T=0.3) and 'HiSelect' (E:T=0.5) conditions. In each screen, the Mel624 cells were independently infected with two human genome-scale libraries: Library A containing ~65,000 sgRNAs (3 sgRNAs per gene or microRNA) and Library B containing ~55,000 sgRNAs (3 different sgRNAs per gene). To examine the sgRNA library representation through each step of the screen, deep sequencing analysis was used to count sgRNA reads. The sgRNA reads from transduced cells 5-7 days post-puromycin selection showed high concordance with the reads from GeCKO plasmid pool (FIG. 2B), demonstrating that sgRNA library representation was maintained during transduction and puromycin selection. It was observed that the distribution of sgRNA reads in T cell-treated samples versus controls was significantly different only in the HiSelect screens (FIG. 2C, Kolmogorov-Smirnov test, P=7.5× $10^{-5}$), and not in the LoSelect screens (P=0.07), indicating that the efficiency of this 2CT CRISPR platform depends mainly on the selection pressure applied by T cells.

For both screens, sgRNA enrichment was analyzed at the individual gene level by multiple methods: 1) top ranked genes by the second most enriched sgRNA (FIGS. 2D and 6A-6B); and 2) the percentage of sgRNAs enriched in the top 5% of all sgRNAs for each gene. Both methods showed a high degree of overlap (FIGS. 2E and 6A-6B). Known T cell response genes, including HLA-A, B2M, TAP1, TAP2 and TAPBP, ranked amongst the top 20 genes enriched in the HiSelect screens (FIGS. 2D and 2E), indicating that CRISPR mediated perturbations in MHC-I pathway rendered these cells resistant to T cell-mediated cytolysis. Further analyses of these data showed enrichment of several genes not previously implicated in orchestrating T cell anti-tumor responses. Consistent enrichment between multiple, independent sgRNAs targeting the same gene was looked for. Two genes (SOX10 and CD58) had 5 out of 6 sgRNAs and three genes (MLANA, PSMB5 and RPL23) had 4 out of 6 sgRNAs enriched in top 5% of most enriched sgRNAs (FIG. 2E). Despite the disparity in the enriched sgRNA distributions between LoSelect and HiSelect screens, which is most likely due to differential T cell selection pressures (FIG. 2C), ~10% of genes ranked amongst top 5% most enriched were overlapped across both screens (FIG. 7A-7B).

The top 554 ranked genes were further selected from HiSelect screens with the second most enriched sgRNA score >0.5 (estimated FDR=0.1% based on 1000 non-target control sgRNAs; FIGS. 8A-8B) for ontology and pathway enrichment analyses to discover groups of genes underlying T cell resistance. The loss of a significant number of genes involved in EIF2 signaling, SRP-dependent peptide targeting to membrane, assembly of RNA polymerase II, and protein ubiquitination pathways (F-test, Bonferroni corrected $P<0.05$) conferred resistance to T cell-mediated cytolysis (Tables 2 and 3), emphasizing the role of these pathways in modulating T cell response to tumor cells. Table 2 shows the gene set enrichment analysis output for top 100 ranked genes from HiSelect screens. Table 3 shows the pathway enrichment analysis of the top 500 ranked genes from HiSelect screens.

TABLE 2

| GO biological process complete | Homo sapiens - REFLIST (20814) | Genes Uploaded (90) | Bonferroni corrected (P-value) |
|---|---|---|---|
| antigen processing and presentation of endogenous peptide antigen via MHC class I (GO: 0019885) | 11 | 5 | 1.36E−05 |
| antigen processing and presentation of endogenous peptide antigen (GO: 0002483) | 12 | 5 | 2.09E−05 |
| antigen processing and presentation of endogenous antigen (GO: 0019883) | 14 | 5 | 4.49E−05 |
| antigen processing and presentation of exogenous peptide antigen via MHC class I, TAP-dependent (GO: 0002479) | 75 | 9 | 4.32E−07 |
| antigen processing and presentation of exogenous peptide antigen via MHC class I (GO: 0042590) | 79 | 9 | 6.81E−07 |
| SRP-dependent cotranslational protein targeting to membrane (GO: 0006614) | 109 | 12 | 6.21E−10 |
| cotranslational protein targeting to membrane (GO: 0006613) | 112 | 12 | 8.52E−10 |
| protein targeting to ER (GO: 0045047) | 113 | 12 | 9.44E−10 |
| establishment of protein localization to endoplasmic reticulum (GO: 0072599) | 117 | 12 | 1.41E−09 |
| ribosome assembly (GO: 0042255) | 51 | 5 | 2.54E−02 |
| protein localization to endoplasmic reticulum (GO: 0070972) | 136 | 12 | 8.05E−09 |
| antigen processing and presentation of peptide antigen via MHC class I (GO: 0002474) | 104 | 9 | 7.41E−06 |
| nuclear-transcribed mRNA catabolic process, nonsense-mediated decay (GO: 0000184) | 119 | 10 | 1.09E−06 |
| viral transcription (GO: 0019083) | 111 | 9 | 1.30E−05 |
| viral gene expression (GO: 0019080) | 121 | 9 | 2.73E−05 |
| multi-organism metabolic process (GO: 0044033) | 127 | 9 | 4.13E−05 |
| protein targeting to membrane (GO: 0006612) | 186 | 12 | 2.90E−07 |
| tumor necrosis factor-mediated signaling pathway (GO: 0033209) | 115 | 7 | 6.12E−03 |
| antigen processing and presentation of exogenous peptide antigen (GO: 0002478) | 171 | 10 | 3.43E−05 |
| antigen processing and presentation of exogenous antigen (GO: 0019884) | 178 | 10 | 4.99E−05 |
| nuclear-transcribed mRNA catabolic process (GO: 0000956) | 181 | 10 | 5.84E−05 |
| antigen processing and presentation of peptide antigen (GO: 0048002) | 188 | 10 | 8.33E−05 |
| translational termination (GO: 0006415) | 171 | 9 | 5.14E−04 |
| mRNA catabolic process (GO: 0006402) | 193 | 10 | 1.06E−04 |
| translational elongation (GO: 0006414) | 200 | 10 | 1.48E−04 |
| viral life cycle (GO: 0019058) | 241 | 11 | 7.00E−05 |
| RNA catabolic process (GO: 0006401) | 222 | 10 | 3.90E−04 |
| cellular protein complex disassembly (GO: 0043624) | 200 | 9 | 1.90E−03 |
| antigen processing and presentation (GO: 0019882) | 225 | 10 | 4.41E−04 |
| establishment of protein localization to membrane (GO: 0090150) | 273 | 12 | 2.14E−05 |
| protein complex disassembly (GO: 0043241) | 220 | 9 | 4.18E−03 |
| cellular response to tumor necrosis factor (GO: 0071356) | 203 | 8 | 2.42E−02 |
| macromolecular complex disassembly (GO: 0032984) | 229 | 9 | 5.81E−03 |
| translational initiation (GO: 0006413) | 232 | 9 | 6.47E−03 |
| establishment of protein localization to organelle (GO: 0072594) | 348 | 12 | 3.03E−04 |

TABLE 2-continued

| GO biological process complete | Homo sapiens - REFLIST (20814) | Genes Uploaded (90) | Bonferroni corrected (P-value) |
|---|---|---|---|
| viral process (GO: 0016032) | 674 | 23 | 8.12E−11 |
| multi-organism cellular process (GO: 0044764) | 678 | 23 | 9.19E−11 |
| protein localization to membrane (GO: 0072657) | 388 | 13 | 1.10E−04 |
| nucleobase-containing compound catabolic process (GO: 0034655) | 344 | 11 | 2.45E−03 |
| interspecies interaction between organisms (GO: 0044419) | 749 | 23 | 7.25E−10 |
| symbiosis, encompassing mutualism through parasitism (GO: 0044403) | 749 | 23 | 7.25E−10 |
| translation (GO: 0006412) | 397 | 12 | 1.24E−03 |
| peptide biosynthetic process (GO: 0043043) | 420 | 12 | 2.25E−03 |
| cellular nitrogen compound catabolic process (GO: 0044270) | 386 | 11 | 7.50E−03 |
| heterocycle catabolic process (GO: 0046700) | 386 | 11 | 7.50E−03 |
| protein targeting (GO: 0006605) | 423 | 12 | 2.43E−03 |
| aromatic compound catabolic process (GO: 0019439) | 396 | 11 | 9.60E−03 |
| regulation of innate immune response (GO: 0045088) | 368 | 10 | 3.66E−02 |
| peptide metabolic process (GO: 0006518) | 517 | 14 | 4.05E−04 |
| protein localization to organelle (GO: 0033365) | 528 | 14 | 5.24E−04 |
| organic cyclic compound catabolic process (GO: 1901361) | 427 | 11 | 1.97E−02 |
| amide biosynthetic process (GO: 0043604) | 480 | 12 | 9.08E−03 |
| cellular macromolecule catabolic process (GO: 0044265) | 764 | 19 | 4.87E−06 |
| cellular component disassembly (GO: 0022411) | 493 | 12 | 1.20E−02 |
| mRNA metabolic process (GO: 0016071) | 564 | 13 | 7.71E−03 |
| single-organism membrane organization (GO: 0044802) | 715 | 16 | 5.58E−04 |
| macromolecule catabolic process (GO: 0009057) | 899 | 19 | 6.82E−05 |
| cytoplasmic transport (GO: 0016482) | 713 | 15 | 3.27E−03 |
| cellular amide metabolic process (GO: 0043603) | 666 | 14 | 8.38E−03 |
| membrane organization (GO: 0061024) | 877 | 17 | 1.58E−03 |
| intracellular protein transport (GO: 0006886) | 727 | 14 | 2.31E−02 |
| cellular protein localization (GO: 0034613) | 1138 | 18 | 1.25E−02 |
| cellular macromolecule localization (GO: 0070727) | 1146 | 18 | 1.38E−02 |
| organic substance catabolic process (GO: 1901575) | 1509 | 22 | 2.72E−03 |
| protein complex subunit organization (GO: 0071822) | 1406 | 20 | 1.52E−02 |
| cellular catabolic process (GO: 0044248) | 1448 | 20 | 2.38E−02 |
| catabolic process (GO: 0009056) | 1764 | 24 | 2.46E−03 |
| multi-organism process (GO: 0051704) | 2169 | 29 | 1.35E−04 |
| macromolecular complex subunit organization (GO: 0043933) | 2074 | 27 | 8.65E−04 |
| immune system process (GO: 0002376) | 2163 | 25 | 2.64E−02 |
| gene expression (GO: 0010467) | 3825 | 40 | 9.26E−05 |
| RNA biosynthetic process (GO: 0032774) | 2680 | 28 | 4.02E−02 |
| cellular protein metabolic process (GO: 0044267) | 3575 | 35 | 6.72E−03 |
| cellular component organization (GO: 0016043) | 5066 | 45 | 1.00E−03 |
| protein metabolic process (GO: 0019538) | 4241 | 37 | 4.70E−02 |
| cellular component organization or biogenesis (GO: 0071840) | 5188 | 45 | 2.09E−03 |
| cellular macromolecule metabolic process (GO: 0044260) | 6753 | 51 | 1.50E−02 |
| macromolecule metabolic process (GO: 0043170) | 7438 | 55 | 6.68E−03 |
| metabolic process (GO: 0008152) | 9928 | 64 | 4.46E−02 |
| Unclassified (UNCLASSIFIED) | 4272 | 7 | 0.00E+00 |

TABLE 3

| Ingenuity ® Canonical Pathways | −log (p-value) | Ratio | Molecules |
|---|---|---|---|
| EIF2 Signaling | 1.26E+01 | 1.44E−01 | RPL24, RPLP1, RPL22L1, RPL35A, EIF2S1, RPL7A, RPL13, RPL18A, EIF3D, RPL23A, RPL21, RPL18, RPS19, RPL34, RPL3, RPS10, RPL23, RPS29, RPL10A, RPL9, RPL15, RPL8, RPL10, EIF3L, RPLP0, RPL38 |
| Antigen Presentation Pathway | 5.65E+00 | 2.16E−01 | B2M, CALR, PSMB5, HLA-A, HLA-F, TAP1, TAP2, TAPBP |
| Endoplasmic Reticulum Stress Pathway | 3.93E+00 | 2.38E−01 | CALR, MAP3K5, EIF2S1, CASP7, MBTPS2 |
| Assembly of RNA Polymerase II Complex | 3.73E+00 | 1.40E−01 | TAF1, TAF5, TBP, GTF2H5, TAF3, TAF7, TAF1L |
| Cytotoxic T Lymphocyte-mediated Apoptosis of Target Cells | 3.03E+00 | 1.56E−01 | B2M, FADD, HLA-A, CASP8, CASP7 |
| Interferon Signaling | 2.79E+00 | 1.39E−01 | JAK1, IFNGR2, JAK2, STAT1, TAP1 |
| Role of JAK1, JAK2 and TYK2 in Interferon Signaling | 2.62E+00 | 1.67E−01 | JAK1, IFNGR2, JAK2, STAT1 |
| IL-15 Production | 2.42E+00 | 1.48E−01 | JAK1, JAK2, STAT1, PTK7 |
| TNFR1 Signaling | 2.23E+00 | 1.04E−01 | MAP4K2, FADD, RIPK1, CASP8, CASP7 |
| Protein Ubiquitination Pathway | 2.03E+00 | 5.10E−02 | USP31, B2M, PSMB3, PSMA6, PSMB5, HLA-A, USP10, PSMC4, PSMD14, PSMC2, TAP2, TAP1, VHL |
| Role of JAK family kinases in IL-6-type Cytokine Signaling | 1.67E+00 | 1.20E−01 | JAK1, JAK2, STAT1 |
| Death Receptor Signaling | 1.62E+00 | 6.52E−02 | FADD, RIPK1, MAP3K5, CASP8, ACTG1, CASP7 |

Example 3

This example demonstrates the validation of the most enriched genes from LoSelect and HiSelect screens.

To validate top candidates, the 2CT CRISPR assay was performed using multiple individual sgRNAs (FIG. 9). Seventeen genes were selected based on two criteria. First, the gene must be present in the top 20 ranked genes in either the HiSelect or LoSelect screen (FIGS. 2E and 7A-7B). Second, the gene must be frequently mutated in patients with multiple cancer types curated in cBioPortal (Gao et al., *Science Signaling*, 6: p 11 (2013); Cerami et al., *Cancer Discovery*, 2: 401-404 (2012)) (Table 4). CTAGJB (encoding NY-ESO-1) was also included as a positive control. Using ESO T cells and Mel624 cells, it was found that 15 out of 17 genes had at least one sgRNA that showed greater than 25% resistant cell survival against T cell-mediated killing (FIGS. 3A-3C). Without being bound to a particular theory or mechanism, it is believed that loss-of-function mutations in these genes may lead to resistance to T cell-mediated lysis by altering MHC-I presentation of specifically the NY-ESO-1 antigen or possibly via other more general mechanisms. To address this question, the resistance of eight of these genes was re-assessed in MART1+ Mel624 cells using MART-1 antigen specific T cells (Marti T cells) with high avidity TCRs (Robbins et al., *J. Immuno.*, 180: 6116-131 (2008); Johnson et al., *J. Immunol.*, 177: 6548-59 (2006)) (FIG. 10A-10B), and observed phenotypic consistency (FIGS. 3D-3E). The efficiency of sgRNAs to form indels at the target loci in Mel624 cells was also verified (FIG. 11A-11K).

TABLE 4

List of genes and sgRNA spacers used in validation screens.

| sgRNA_Name | Spacer sequence | SEQ ID NO: for spacer sequence |
|---|---|---|
| APLNR_sgRNA_1 | GTACGTGTAGGTAGCCCACA | 1. |
| APLNR_sgRNA_2 | GTAGCGGTCGAAGCTGAGGC | 2. |
| APLNR_sgRNA_3 | TTTCGACCCCCGCTTCCGCC | 3. |
| APLNR_sgRNA_4 | CTTCCGCAAGGAACGCATCG | 4. |
| BBS1_sgRNA_1 | TCATGGAGCAACATGAGCCC | 5. |
| BBS1_sgRNA_2 | CCTTTGAGCACCTTCAGGCG | 6. |
| BBS1_sgRNA_3 | CGCATCCAACCACTTCGAAT | 7. |
| BBS1_sgRNA_4 | GCAATGAGGCCAATTCGAAG | 8. |
| CD58_sgRNA_1 | TGGTTGCTGGGAGCGACGCG | 9. |
| CD58_sgRNA_2 | GACCACGCTGAGGACCCCCA | 10. |

TABLE 4 -continued

List of genes and sgRNA spacers used in validation screens.

| sgRNA_Name | Spacer sequence | SEQ ID NO: for spacer sequence |
|---|---|---|
| CD58_sgRNA_3 | ATGTTAAGTTGTAGATAGTG | 11. |
| CD58_sgRNA_4 | CATGTTGTAATTACTGCTAA | 12. |
| COL17A1_sgRNA_1 | TTTTTATCCAGACCCAGCCA | 13. |
| COL17A1_sgRNA_2 | TCAGGAGAAGAAAGAGAGAG | 14. |
| COL17A1_sgRNA_3 | ACCAAGAAAAACAAACGAGA | 15. |
| COL17A1_sgRNA_4 | TAGTTACTTACTTGGIGGTA | 16. |
| CTAG1B_sgRNA_1 | TCCGGAGCCATGCAGGCCGA | 17. |
| CTAG1B_sgRNA_2 | GAACAGAATACAACTCAAGC | 18. |
| CTAG1B_sgRNA_3 | CATGCCTTTCGCGACACCCA | 19. |
| DEFB134_sgRNA_1 | CTAGTGGCAGGGTCTGACAT | 20. |
| DEFB134_sgRNA_2 | TGTTAAGGAGGCTAGTGGCA | 21. |
| DEFB134_sgRNA_3 | AAAGAAAGACAAACACAACA | 22. |
| DEFB134_sgRNA_4 | CACAAGAAATGCTATAAAAA | 23. |
| DHX9_sgRNA_1 | GGAGTATCAGTAAGTGGGGG | 24. |
| DHX9_sgRNA_2 | GCTTTGAGAGCCAGATGTGG | 25. |
| DHX9_sgRNA_3 | CCTCGGTCCCAGGTGGGCCC | 26. |
| DHX9_sgRNA_4 | CTCCGGACTTACAAAGAAGA | 27. |
| KHDRBS3_sgRNA_1 | CGCTTCAGAGAATTGCCACG | 28. |
| KHDRBS3_sgRNA_2 | GGGACTGGCGGGGATCGCCG | 29. |
| KHDRBS3_sgRNA_3 | TCCCGTAAAACAGTTCCCTA | 30. |
| KHDRBS3_sgRNA_4 | AAACCCACCTTGCGTACAAG | 31. |
| MLANA_sgRNA_1 | GCACGGCCACTCTTACACCA | 32. |
| MLANA_sgRNA_2 | TCTATGGTTACCCCAAGAAG | 33. |
| MLANA_sgRNA_3 | CTGGGAGTCTTACTGCTCAT | 34. |
| MLANA_sgRNA_4 | TTGAACTTACTCTTCAGCCG | 35. |
| Nontargeting_Control | TCCCCGAGACCATCTTAGGG | 36. |
| PSMB5_sgRNA_1 | GCAAGCGCCATGTCTAGTGT | 37. |
| PSMB5_sgRNA_2 | TGAGAACGCCTAGCAAAGAT | 38. |
| PSMB5_sgRNA_3 | TTTGTACTGATACACCATGT | 39. |
| PSMB5_sgRNA_4 | CTTTCCAGGCCTCTACTACG | 40. |
| PTCD2_sgRNA_1 | TGCAGGAGAACTCGATTCGA | 41. |
| PTCD2_sgRNA_2 | AGAATTTCAACAAAAGAAAG | 42. |
| PTCD2_sgRNA_3 | ATTCATGATTTGAGAAAAAA | 43. |
| PTCD2_sgRNA_4 | AGCTAATGCCACAGCGAAAC | 44. |
| RPL23_sgRNA_1 | ATTTCCTTGGGTCTTCCGGT | 45. |
| RPL23_sgRNA_2 | GCGAAATTCCGGATTTCCTT | 46. |
| RPL23_sgRNA_3 | CAATTGATTACAGCTCCTAC | 47. |
| RPL23_sgRNA_4 | TCTCTCAGTACATCCAGCAG | 48. |

TABLE 4 -continued
List of genes and sgRNA spacers used in validation screens.

| sgRNA_Name | Spacer sequence | SEQ ID NO: for spacer sequence |
|---|---|---|
| SOX10_sgRNA_1 | GGCTCAGCTCCACCTCCGAT | 49. |
| SOX10_sgRNA_2 | GTTCCCCGTGTGCATCCGCG | 50. |
| SOX10_sgRNA_3 | CCGCTCAGCCTCCTCGATGA | 51. |
| SOX10_sgRNA_4 | TGACAAGCGCCCCTTCATCG | 52. |
| SRP54_sgRNA_1 | GGTGACGTTTCCTCATTGGG | 53. |
| SRP54_sgRNA_2 | ACCGCCGCGTTCCTTCTACG | 54. |
| SRP54_sgRNA_3 | GTAACCTACCTTCCATAAAA | 55. |
| SRP54_sgRNA_4 | AGCTAGCATATTATTACCAG | 56. |
| TAPBP_sgRNA_1 | GGTGCACTGCTGTTGCGCCA | 57. |
| TAPBP_sgRNA_2 | GAACCAACACTCGATCACCG | 58. |
| TAPBP_sgRNA_3 | AAGCGGCTCATCTCGCAGTG | 59. |
| TAPBP_sgRNA_4 | GAACCAACACTCGATCACCG | 60. |
| TWF1_sgRNA_1 | TTAGATTCTCAGAATGCCCA | 61. |
| TWF1_sgRNA_2 | GGTTGTTTGTCCTCCAACAG | 62. |
| TWF1_sgRNA_3 | TTACTTACATGAGAATGATC | 63. |
| TWF1_sgRNA_4 | ATCTTTGCCAGAGCCAGAAA | 64. |

To better understand the effect of genetic background, the consistency of validated hits in A375, an unrelated NY-ESO-1+ melanoma cell line, was examined. Multiple sgRNAs targeting apelin receptor (APLNR), (Bardet-Biedl Syndrome 1 (BBS1), lymphocyte function-associated antigen 3 (CD58) and sex determining region Y box 10 (SOX10) in A375 cells also showed resistance against T cell activity (FIG. 3F-3G), confirming these genes as resistance mechanisms in 2 different melanoma cell lines. Using flow cytometry and immunoblot analysis, that these sgRNAs efficiently reduced the protein levels of the targeted genes in A375 cells was also confirmed (FIGS. 12A-12B).

Interferon gamma (IFNγ) secretion is a marker of effector T cell activation and also itself an effective means of tumor cell lysis. To test if the resistance mechanism of any of these genes was dependent on alteration of IFNγ secretion, its release in the supernatants after a co-culture assay was measured. CD58 perturbations in tumor cells significantly reduced secretion of IFNγ from T cells, however a consistent effect with APLNR and SOX10 modifications on IFNγ secretion was not observed (FIG. 13). None of the BBS1 targeting sgRNAs reduced IFNγ secretion significantly implying that an alternate mechanism underlies their T cell resistance phenotype (FIGS. 3F, 3G, and 13). These validated genes were further characterized to address whether T cell resistance was due to the loss of expression of β2M or up-regulation of the immune checkpoint ligands PD-L1, PD-L2 and galectin-9 on the cell surface. None of these markers were altered significantly in APLNR, BBS1, CD58 or SOX10 edited cells treated with ESO T cells for 24 hours (FIGS. 14A-14D). Broadly, these results indicate that multiple gene products involved in the regulation of the target cell lysis by T cells yet remain to be characterized.

Example 4

This example demonstrates the association of top ranked genes from HiSelect screens with cytolytic activity in human cancers.

To determine the implications of enriched gene targets from the 2CT screen on immunotherapy studies, it was examined whether expression levels of these genes were associated with survival in melanoma patients after CTLA4 blockade with ipilimumab (Van Allen et al., *Science,* 350: 207-211 (2015)). It was found that the expression levels of two MHC class I genes, B2M and TAP1, were associated with overall survival of patients in response to ipilimumab, while TAP2 levels were marginally associated with overall survival (FIGS. 4A-4B and 15A-15B). Any significant associations of other 2CT validated genes with overall survival in this small cohort (n=42 patients) were not found. Multiple studies have established that clinical outcomes of CTLA4 blockade with ipilimumab depend predominantly on tumor infiltration and cytolytic activity of T cells (Van Allen et al., *Science,* 350: 207-211 (2015); Kvistborg et al., *Science Transl. Med.,* 6: 254ra128-254ra128 (2014); Egen et al., *Nat. Immunol.,* 3: 611-618 (2002)). A hallmark of cytolytic activity is the expression of cytolytic molecules perforin (PRF1) and granzyme A (GZMA) in the tumor microenvironment ("CYT expression") (Rooney et al., *Cell,* 160: 48-61 (2015). B2M, TAP1 and TAP2 were strongly correlated with CYT expression in the tumor microenvironment (Spearman $\rho \geq 0.6$, FIG. 4C). Interestingly, it was observed that APLNR expression was moderately correlated with CYT expression ($\rho=0.43$, P=0.005) and T cell signature genes ($\rho=0.48$, P=0.001) but not with NK cell signature genes (FIG. 4C). Based on these correlative findings in a small cohort of melanoma patients, the correlation analysis was expanded across multiple cancer types in TCGA datasets.

It has been previously shown that genes which confer survival in cancers are cancer-type and cell-type dependent, but the majority of context independent genes belong to core biological processes (Hart et al., *Cell*, 163: 1515-26). It was attempted to apply the same principle to T cell responsive processes in tumor cells. Genes that correlate with CYT across different Cancer Genome Atlas (TCGA) datasets were searched for in order to obtain cancer-type independent genes which could be involved in core processes in cancer cell necessary for T cell-mediated killing. A dataset was generated from each cancer type containing genes that positively correlated with CYT expression (threshold P<0.05) and overlapped each of these datasets with the top 554 ranked genes from HiSelect screens (FIGS. 4D-4E). This strategy was effective as it was found that the expression of B2M was positively associated with CYT expression across all 36 tumor types (FIG. 4F). Additionally, it was observed that the expression of APLNR and CD58 correlated with cytolytic activity in 30 and 19 different tumor types, respectively (FIG. 4F). It was also found that along with known antigen presentation and interferon response genes (JAK2, STAT1), genes in cancer cells likely involved in adhesion (ICAM1) and co-stimulation (CLECL1, LILRA1, LILRA3, HLA-F) of T cells were strikingly correlated across majority of cancer types (FIG. 4F). Genes associated with cytolytic activity in TCGA cancer types included TBXAS1, GMIP, OTOA, LAIR1, CLEC1, GPSM3, TRAF1, JAK2, TAPBP, TAPBPL, ICAM1, LILRA1, LILRA3, STAT1, HLA-A, B2M, HLA-F, TAP1, and TAP2. It was also found that these genes do not distinguish between immunogenic (melanomas) and non-immunogenic (breast) cancer types.

The positive correlation of CRISPR screen candidates with CYT expression across several cancer types emphasizes that the loss of these T cell-response genes in tumor is very likely associated with the loss of cytolytic activity in tumor microenvironment implying that one of the possible mechanisms of how many cancers evade inherent T cell-mediated immune selection pressure is via loss of these response genes. These genes included the T cell antigen itself, co-stimulatory molecules like CD58 and regulators of antigen presentation, antigen expression or extrinsic apoptosis pathways, and validated novel candidates like APLNR, COL17A1 and RPL23.

Using an unbiased functional genomic screen, genes in melanoma that confer the ability to elicit a T cell response were identified, including several previously not known to play a role in anti-tumor function of T cells. Although these experiments were only in melanoma models, further analysis of 2CT screen targets in TCGA expression data suggests that a subset of targets may be involved in immune evasion across different cancer types. With many different cancer models now available, future 2CT CRISPR screens may enable the discovery of novel clinical targets and biomarkers for immune- and cell-based therapies.

Example 5

This example demonstrates the validation of genes which confer the ability of renal cell carcinoma (RCC) cells to elicit CYT expression.

HLA-A2+ RCC cells were transduced with a retrovirus encoding NY-ESO-1. The NY-ESO-1+/HLA-A2+ RCC cells were transduced with a CRISPR lentivirus encoding control, APLNR, BBS1, or CD58 sgRNA to produce gene-perturbed NY-ESO-1+/HLA-A2+ RCC cells. The gene-perturbed NY-ESO-1+/HLA-A2+ RCC cells were co-cultured with NY-ESO-1-specific T cells. The resistance of the RCC cells to CYT expression was determined and normalized. The results are shown in FIG. 16. As shown in FIG. 16, knockout of APLNR, BBS1, or CD58 in RCC cells confers resistance to T cell mediated cytolysis.

Example 6

This example demonstrates that Aplnr-knockdown in mhgp100-B16 tumors reduces anti-tumor efficacy of adoptive transfer of Pmel T cells.

Tumor cells were treated with anti-Apinr short hairpin RNA (shRNA). Control tumor cells were treated with irrelevant shRNA (scramble). B6 mice were implanted with $5 \times 10^5$ tumor cells per mouse. The mice were treated with $1 \times 10^6$ Pmel T cells, IL-2, and radiation (IR) on day 10 following tumor impanation. Control mice were treated with IR and IL-2 only. Tumor area and survival were measured. The results are shown in FIGS. 17A and 17B. As shown in FIGS. 17A and 17B, knockout of Apinr in melanoma tumor cells reduced the anti-tumor efficacy of adoptive transfer of Pmel T cells.

Example 7

This example demonstrates that apelin ligand is produced by T cells and that apelin localizes in T cells during immune-synapse formation.

The fold change in APELIN mRNA expression by bulk human anti-NY-ESO-1 T cells upon stimulation with OKT3 antibody for various time periods was measured. The results are shown in Table 5.

TABLE 5

| Fold change in APELIN mRNA expression | Duration of stimulation with OKT3 (time in hours) |
|---|---|
| 1 | 0 (control) |
| 1.5 | 16 |
| 3.5 | 24 |

Bulk human anti-NY-ESO-1 T cells (effector cells) were co-cultured with A375 cells (target cells) at various effector:target ratios and for various time periods. The fold change in apelin released by the T cells upon co-culture was measured by ELISA. The results are shown in Table 6.

TABLE 6

| Apelin release (pg/ml) | Effector:target ratio | Duration of co-culture (hours) |
|---|---|---|
| 80 | Tumor alone | None |
| 60 | 0.5 | 4 |
| 70 | 1.0 | 4 |
| 150 | 0.5 | 8 |
| 160 | 1.0 | 8 |

As shown in Tables 5 and 6, apelin ligand is produced by T cells.

The localization of apelin in human anti-NY-ESO T cells was examined under a microscope. It was observed that apelin localized in the leading edge at the pole opposite to the CD3 cluster in the T cells cultured alone.

The localization of apelin in human anti-NY-ESO T cells which were co-cultured with A375 cells was also examined under a microscope. In the co-cultured cells, apelin localized at the immune synapse.

Example 8

This example demonstrates that APLNR loss-of-function mutations were detected in tumor lesions which were refractory to immunotherapies.

Tumor lesions which were refractory to the immunotherapies shown in Table 7 were tested for expression of non-synonymous APLNR mutations. The results are shown in Table 7. FIG. 18A shows the location of the mutations on the APLNR protein.

TABLE 7

| APLNR mutation | Immunotherapies |
| --- | --- |
| T44S or C181S | Ipilimumab (Ipi), nivolumab (nivo), and adoptive cell therapy (ACT) |
| D184N, R236C, or W261X | Ipi and pembrolizumab (Pembro) |
| P292L, G349E, or E367K | Ipi |
| G349W | Pembro |

Tumor cells were untreated or treated with APLNR sg RNA (sg1) followed by rescue with WT APLNR RNA or APLNR RNA with one of the mutations indicated in FIG. 18B. The tumor cells were co-cultured with T cells, and cytolysis was measured. The results are shown in FIG. 18B. As shown in FIG. 18B, cells treated with rescue APLNR RNA with a mutation encoding G349E or T44S resist the restoration of T-cell-mediated cytolysis in APLNR-perturbed tumor cells (n=3 biological replicates).

Example 9

This example demonstrates that APLNR interacts with JAK1.

The second-most-enriched sgRNA score in the CRISPR screens for 96 APLNR-interacting proteins from the BIOGRID database is shown in FIG. 19A. JAK1 was identified as a candidate for interacting with APLNR. JAK1 was isolated from A375 cell lysates by immunoprecipitation. Immunoprecipitation pull-down of IgG antibodies served as a control. The pull-down samples were tested for the presence of APLNR or JAK1. As a positive control, the pull-down samples were tested for the presence of actin. The results are shown in FIG. 19B. As shown in FIG. 19B, APLNR interacts with JAK1.

Example 10

This example demonstrates that APLNR enhances IFN γ signaling in tumor cells.

APLNR-edited (knockout) tumor cells were treated with 1 µg (n=3 biological replicates). Control tumor cells were treated with off-target sgRNA. At 0, 8, and 24 hours post-treatment, the cells underwent quantitative PCR analysis of JAK1-STAT1 pathway-induced genes. The results are shown in FIG. 20. As shown in FIG. 20, APLNR knockout tumor cells showed less of a change in expression of IFI30, JAK1, TAP1, TAP2, TAPBP, and IRF1 24 hours after treatment as compared to control tumor cells.

Example 11

This example demonstrates that APLNR loss reduces β2M induction and recognition by T cells.

Tumor cells were CRISPR-edited using control sgRNA, anti-APLNR sg1 RNA or anti-APLNR sg2 RNA. The treated cells were co-cultured with anti-NY-ESO-1 T cells. Surface expression of β2M by T cells was measured by fluorescence-activated cell sorting (FACS). The results are shown in FIG. 21A. As shown in FIG. 21A, APLNR loss reduced β2M induction.

A375 tumor cells were CRISPR-edited using control sgRNA, anti-APLNR sg1 RNA, anti-APLNR sg2 RNA, anti-NY-ESO-1 sg1 RNA, or anti-NY-ESO-1 sg1RNA. The treated cells were co-cultured with anti-NY-ESO-1 T cells overnight. IFNγ secretion was measured using ELISA. The results are shown in FIG. 21B. As shown in FIG. 21B, APLNR loss reduced recognition of the tumor cells by the T cells.

Example 12

This example demonstrates that functional loss of APLNR reduces the efficacy of adoptive cell transfer immunotherapy.

B16 melanoma tumor cells were edited using CRISPR to knockout expression of B2m or APLNR. The CRISPR-edited B16 tumor cells were subcutaneously transplanted into mice. After 10 days, tumor-bearing mice were treated with adoptive cell transfer of Pmel T cells. Tumor growth and survival was measured. The results are shown in FIGS. 22A-22C.

As shown in FIGS. 22A-22C, the functional loss of APLNR reduced the efficacy of the adoptive cell transfer immunotherapy.

Example 13

This example demonstrates that the functional loss of APLNR reduces the efficacy of anti-CTLA4 blockade immunotherapy.

B2905 melanoma tumor cells (derived from C57BL/6-HGF mice) were edited using CRISPR to knockout expression of APLNR. The CRISPR-edited B2905 melanoma cells were subcutaneously implanted into mice. The mice were treated with four doses of 250 µg of IgG control or anti-CTLA4 antibodies on days 10, 13, 16, and 19 post-implantation. Change in tumor area was measured. The results are shown in FIGS. 23A and 23B.

As shown in FIGS. 23A-23B, the functional loss of APLNR reduced the efficacy of anti-CTLA4 blockade immunotherapy.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of selecting a therapy for a cancer patient and treating cancer in the patient, the method comprising:
measuring a level of one or both of (i) mRNA and (ii) polypeptide expressed from the APLNR gene in a cancer cell from the patient;
measuring a level of one or both of (i) mRNA and (ii) polypeptide expressed from the APLNR gene in a noncancerous cell;
comparing the level of one or both of (i) mRNA and (ii) polypeptide measured in the cancer cell with the level of one or both of (i) mRNA and (ii) polypeptide, respectively, measured in the noncancerous cell;
selecting the patient for a therapy which is not a T cell therapy when the level of one or both of (i) mRNA and (ii) polypeptide measured in the cancer cell is decreased as compared to the level of one or both of (i) mRNA and (ii) polypeptide, respectively, measured in the noncancerous cell; and
selecting the patient for a T cell therapy when the level of one or both of (i) mRNA and (ii) polypeptide measured in the cancer cell is not decreased as compared to the level of one or both of (i) mRNA and (ii) polypeptide, respectively, measured in the noncancerous cell;
treating the patient by administering a therapy which is not a T cell therapy to the patient in an amount effective to treat cancer in the patient when the level of one or both of (i) mRNA and (ii) polypeptide measured in the cancer cell is decreased as compared to the level of one or both of (i) mRNA and (ii) polypeptide, respectively, measured in the noncancerous cell; and
treating the patient by administering a T cell therapy to the patient in an amount effective to treat cancer in the patient when the level of one or both of (i) mRNA and (ii) polypeptide measured in the cancer cell is not decreased as compared to the level of one or both of (i) mRNA and (ii) polypeptide, respectively, measured in the noncancerous cell.

2. The method according to claim 1, wherein the decrease in the level of one or both of (i) mRNA and (ii) polypeptide confers resistance to T cell-mediated cytolysis to the cancer cell.

3. The method according to claim 1, wherein the therapy which is not a T cell therapy is surgical resection, chemotherapy, radiotherapy, NK cell therapy, B cell therapy, gene therapy, anti-cancer vaccine therapy, targeted drug inhibitor therapy, or any combination thereof.

4. The method according to claim 1, wherein the T cell therapy comprises one or more T cells or one or more cells which have been modified to express a T cell receptor.

5. The method according to claim 1, further comprising measuring a level of one or both of (i) mRNA and (ii) polypeptide expressed from the CD58 gene in a cancer cell from the patient.

6. The method according to claim 1, further comprising measuring a level of one or both of (i) mRNA and (ii) polypeptide expressed from the BBS1 gene in a cancer cell from the patient.

* * * * *

```
                        SEQUENCE LISTING

<160> NUMBER OF SEQ ID NOS: 98

<210> SEQ ID NO 1
    <211> LENGTH: 20
    <212> TYPE: DNA
    <213> ORGANISM: Artificial Sequence
    <220> FEATURE:
    <223> OTHER INFORMATION: synthetic

<400> SEQUENCE: 1
gtacgtgtag gtagcccaca                                                   20

<210> SEQ ID NO 2
    <211> LENGTH: 20
    <212> TYPE: DNA
    <213> ORGANISM: Artificial Sequence
    <220> FEATURE:
    <223> OTHER INFORMATION: synthetic

<400> SEQUENCE: 2
gtagcggtcg aagctgaggc                                                   20

<210> SEQ ID NO 3
    <211> LENGTH: 20
    <212> TYPE: DNA
    <213> ORGANISM: Artificial Sequence
    <220> FEATURE:
    <223> OTHER INFORMATION: synthetic

<400> SEQUENCE: 3
tttcgacccc cgcttccgcc                                                   20

<210> SEQ ID NO 4
    <211> LENGTH: 20
    <212> TYPE: DNA
    <213> ORGANISM: Artificial Sequence
    <220> FEATURE:
    <223> OTHER INFORMATION: synthetic

<400> SEQUENCE: 4
cttccgcaag gaacgcatcg                                                   20

<210> SEQ ID NO 5
    <211> LENGTH: 20
    <212> TYPE: DNA
    <213> ORGANISM: Artificial Sequence
    <220> FEATURE:
    <223> OTHER INFORMATION: synthetic
```

<400> SEQUENCE: 5
tcatggagca acatgagccc                                              20

<210> SEQ ID NO 6
<211> LENGTH: 20
<212> TYPE: DNA
<213> ORGANISM: Artificial Sequence
<220> FEATURE:
<223> OTHER INFORMATION: synthetic

<400> SEQUENCE: 6
cctttgagca ccttcaggcg                                              20

<210> SEQ ID NO 7
<211> LENGTH: 20
<212> TYPE: DNA
<213> ORGANISM: Artificial Sequence
<220> FEATURE:
<223> OTHER INFORMATION: synthetic

<400> SEQUENCE: 7
cgcatccaac cacttcgaat                                              20

<210> SEQ ID NO 8
<211> LENGTH: 20
<212> TYPE: DNA
<213> ORGANISM: Artificial Sequence
<220> FEATURE:
<223> OTHER INFORMATION: synthetic

<400> SEQUENCE: 8
gcaatgaggc caattcgaag                                              20

<210> SEQ ID NO 9
<211> LENGTH: 20
<212> TYPE: DNA
<213> ORGANISM: Artificial Sequence
<220> FEATURE:
<223> OTHER INFORMATION: synthetic

<400> SEQUENCE: 9
tggttgctgg gagcgacgcg                                              20

<210> SEQ ID NO 10
<211> LENGTH: 20
<212> TYPE: DNA
<213> ORGANISM: Artificial Sequence
<220> FEATURE:
<223> OTHER INFORMATION: synthetic

<400> SEQUENCE: 10
gaccacgctg aggaccccca                                              20

<210> SEQ ID NO 11
<211> LENGTH: 20
<212> TYPE: DNA
<213> ORGANISM: Artificial Sequence
<220> FEATURE:
<223> OTHER INFORMATION: synthetic

<400> SEQUENCE: 11
atgttaagtt gtagatagtg                                              20

<210> SEQ ID NO 12

```
<211> LENGTH: 20
<212> TYPE: DNA
<213> ORGANISM: Artificial Sequence
<220> FEATURE:
<223> OTHER INFORMATION: synthetic

<400> SEQUENCE: 12
catgttgtaa ttactgctaa                                                    20

<210> SEQ ID NO 13
<211> LENGTH: 20
<212> TYPE: DNA
<213> ORGANISM: Artificial Sequence
<220> FEATURE:
<223> OTHER INFORMATION: synthetic

<400> SEQUENCE: 13
tttttatcca gacccagcca                                                    20

<210> SEQ ID NO 14
<211> LENGTH: 20
<212> TYPE: DNA
<213> ORGANISM: Artificial Sequence
<220> FEATURE:
<223> OTHER INFORMATION: synthetic

<400> SEQUENCE: 14
tcaggagaag aaagagagag                                                    20

<210> SEQ ID NO 15
<211> LENGTH: 20
<212> TYPE: DNA
<213> ORGANISM: Artificial Sequence
<220> FEATURE:
<223> OTHER INFORMATION: synthetic

<400> SEQUENCE: 15
accaagaaaa acaaacgaga                                                    20

<210> SEQ ID NO 16
<211> LENGTH: 20
<212> TYPE: DNA
<213> ORGANISM: Artificial Sequence
<220> FEATURE:
<223> OTHER INFORMATION: synthetic

<400> SEQUENCE: 16
tagttactta cttggtggta                                                    20

<210> SEQ ID NO 17
<211> LENGTH: 20
<212> TYPE: DNA
<213> ORGANISM: Artificial Sequence
<220> FEATURE:
<223> OTHER INFORMATION: synthetic

<400> SEQUENCE: 17
tccggagcca tgcaggccga                                                    20

<210> SEQ ID NO 18
<211> LENGTH: 20
<212> TYPE: DNA
<213> ORGANISM: Artificial Sequence
<220> FEATURE:
<223> OTHER INFORMATION: synthetic

<400> SEQUENCE: 18
```

```
gaacagaata caactcaagc                                              20

<210> SEQ ID NO 19
<211> LENGTH: 20
<212> TYPE: DNA
<213> ORGANISM: Artificial Sequence
<220> FEATURE:
<223> OTHER INFORMATION: synthetic

<400> SEQUENCE: 19
catgcctttc gcgacaccca                                              20

<210> SEQ ID NO 20
<211> LENGTH: 20
<212> TYPE: DNA
<213> ORGANISM: Artificial Sequence
<220> FEATURE:
<223> OTHER INFORMATION: synthetic

<400> SEQUENCE: 20
ctagtggcag ggtctgacat                                              20

<210> SEQ ID NO 21
<211> LENGTH: 20
<212> TYPE: DNA
<213> ORGANISM: Artificial Sequence
<220> FEATURE:
<223> OTHER INFORMATION: synthetic

<400> SEQUENCE: 21
tgttaaggag gctagtggca                                              20

<210> SEQ ID NO 22
<211> LENGTH: 20
<212> TYPE: DNA
<213> ORGANISM: Artificial Sequence
<220> FEATURE:
<223> OTHER INFORMATION: synthetic

<400> SEQUENCE: 22
aaagaaagac aaacacaaca                                              20

<210> SEQ ID NO 23
<211> LENGTH: 20
<212> TYPE: DNA
<213> ORGANISM: Artificial Sequence
<220> FEATURE:
<223> OTHER INFORMATION: synthetic

<400> SEQUENCE: 23
cacaagaaat gctataaaaa                                              20

<210> SEQ ID NO 24
<211> LENGTH: 20
<212> TYPE: DNA
<213> ORGANISM: Artificial Sequence
<220> FEATURE:
<223> OTHER INFORMATION: synthetic

<400> SEQUENCE: 24
ggagtatcag taagtggggg                                              20

<210> SEQ ID NO 25
<211> LENGTH: 20
<212> TYPE: DNA
```

```
<213> ORGANISM: Artificial Sequence
<220> FEATURE:
<223> OTHER INFORMATION: synthetic

<400> SEQUENCE: 25
gctttgagag ccagatgtgg                                               20

<210> SEQ ID NO 26
<211> LENGTH: 20
<212> TYPE: DNA
<213> ORGANISM: Artificial Sequence
<220> FEATURE:
<223> OTHER INFORMATION: synthetic

<400> SEQUENCE: 26
cctcggtccc aggtgggccc                                               20

<210> SEQ ID NO 27
<211> LENGTH: 20
<212> TYPE: DNA
<213> ORGANISM: Artificial Sequence
<220> FEATURE:
<223> OTHER INFORMATION: synthetic

<400> SEQUENCE: 27
ctccggactt acaaagaaga                                               20

<210> SEQ ID NO 28
<211> LENGTH: 20
<212> TYPE: DNA
<213> ORGANISM: Artificial Sequence
<220> FEATURE:
<223> OTHER INFORMATION: synthetic

<400> SEQUENCE: 28
cgcttcagag aattgccacg                                               20

<210> SEQ ID NO 29
<211> LENGTH: 20
<212> TYPE: DNA
<213> ORGANISM: Artificial Sequence
<220> FEATURE:
<223> OTHER INFORMATION: synthetic

<400> SEQUENCE: 29
gggactggcg gggatcgccg                                               20

<210> SEQ ID NO 30
<211> LENGTH: 20
<212> TYPE: DNA
<213> ORGANISM: Artificial Sequence
<220> FEATURE:
<223> OTHER INFORMATION: synthetic

<400> SEQUENCE: 30
tcccgtaaaa cagttcccta                                               20

<210> SEQ ID NO 31
<211> LENGTH: 20
<212> TYPE: DNA
<213> ORGANISM: Artificial Sequence
<220> FEATURE:
<223> OTHER INFORMATION: synthetic

<400> SEQUENCE: 31
aaacccacct tgcgtacaag                                               20
```

<210> SEQ ID NO 32
<211> LENGTH: 20
<212> TYPE: DNA
<213> ORGANISM: Artificial Sequence
<220> FEATURE:
<223> OTHER INFORMATION: synthetic

<400> SEQUENCE: 32
gcacggccac tcttacacca                                               20

<210> SEQ ID NO 33
<211> LENGTH: 20
<212> TYPE: DNA
<213> ORGANISM: Artificial Sequence
<220> FEATURE:
<223> OTHER INFORMATION: synthetic

<400> SEQUENCE: 33
tctatggtta ccccaagaag                                               20

<210> SEQ ID NO 34
<211> LENGTH: 20
<212> TYPE: DNA
<213> ORGANISM: Artificial Sequence
<220> FEATURE:
<223> OTHER INFORMATION: synthetic

<400> SEQUENCE: 34
ctgggagtct tactgctcat                                               20

<210> SEQ ID NO 35
<211> LENGTH: 20
<212> TYPE: DNA
<213> ORGANISM: Artificial Sequence
<220> FEATURE:
<223> OTHER INFORMATION: synthetic

<400> SEQUENCE: 35
ttgaacttac tcttcagccg                                               20

<210> SEQ ID NO 36
<211> LENGTH: 20
<212> TYPE: DNA
<213> ORGANISM: Artificial Sequence
<220> FEATURE:
<223> OTHER INFORMATION: synthetic

<400> SEQUENCE: 36
tccccgagac catcttaggg                                               20

<210> SEQ ID NO 37
<211> LENGTH: 20
<212> TYPE: DNA
<213> ORGANISM: Artificial Sequence
<220> FEATURE:
<223> OTHER INFORMATION: synthetic

<400> SEQUENCE: 37
gcaagcgcca tgtctagtgt                                               20

<210> SEQ ID NO 38
<211> LENGTH: 20
<212> TYPE: DNA
<213> ORGANISM: Artificial Sequence
<220> FEATURE:

<223> OTHER INFORMATION: synthetic

<400> SEQUENCE: 38
tgagaacgcc tagcaaagat                                                   20

<210> SEQ ID NO 39
<211> LENGTH: 20
<212> TYPE: DNA
<213> ORGANISM: Artificial Sequence
<220> FEATURE:
<223> OTHER INFORMATION: synthetic

<400> SEQUENCE: 39
tttgtactga tacaccatgt                                                   20

<210> SEQ ID NO 40
<211> LENGTH: 20
<212> TYPE: DNA
<213> ORGANISM: Artificial Sequence
<220> FEATURE:
<223> OTHER INFORMATION: synthetic

<400> SEQUENCE: 40
ctttccaggc ctctactacg                                                   20

<210> SEQ ID NO 41
<211> LENGTH: 20
<212> TYPE: DNA
<213> ORGANISM: Artificial Sequence
<220> FEATURE:
<223> OTHER INFORMATION: synthetic

<400> SEQUENCE: 41
tgcaggagaa ctcgattcga                                                   20

<210> SEQ ID NO 42
<211> LENGTH: 20
<212> TYPE: DNA
<213> ORGANISM: Artificial Sequence
<220> FEATURE:
<223> OTHER INFORMATION: synthetic

<400> SEQUENCE: 42
agaatttcaa caaaagaaag                                                   20

<210> SEQ ID NO 43
<211> LENGTH: 20
<212> TYPE: DNA
<213> ORGANISM: Artificial Sequence
<220> FEATURE:
<223> OTHER INFORMATION: synthetic

<400> SEQUENCE: 43
attcatgatt tgagaaaaaa                                                   20

<210> SEQ ID NO 44
<211> LENGTH: 20
<212> TYPE: DNA
<213> ORGANISM: Artificial Sequence
<220> FEATURE:
<223> OTHER INFORMATION: synthetic

<400> SEQUENCE: 44
agctaatgcc acagcgaaac                                                   20

```
<210> SEQ ID NO 45
<211> LENGTH: 20
<212> TYPE: DNA
<213> ORGANISM: Artificial Sequence
<220> FEATURE:
<223> OTHER INFORMATION: synthetic

<400> SEQUENCE: 45
atttccttgg gtcttccggt                                              20

<210> SEQ ID NO 46
<211> LENGTH: 20
<212> TYPE: DNA
<213> ORGANISM: Artificial Sequence
<220> FEATURE:
<223> OTHER INFORMATION: synthetic

<400> SEQUENCE: 46
gcgaaattcc ggatttcctt                                              20

<210> SEQ ID NO 47
<211> LENGTH: 20
<212> TYPE: DNA
<213> ORGANISM: Artificial Sequence
<220> FEATURE:
<223> OTHER INFORMATION: synthetic

<400> SEQUENCE: 47
caattgatta cagctcctac                                              20

<210> SEQ ID NO 48
<211> LENGTH: 20
<212> TYPE: DNA
<213> ORGANISM: Artificial Sequence
<220> FEATURE:
<223> OTHER INFORMATION: synthetic

<400> SEQUENCE: 48
tctctcagta catccagcag                                              20

<210> SEQ ID NO 49
<211> LENGTH: 20
<212> TYPE: DNA
<213> ORGANISM: Artificial Sequence
<220> FEATURE:
<223> OTHER INFORMATION: synthetic

<400> SEQUENCE: 49
ggctcagctc cacctccgat                                              20

<210> SEQ ID NO 50
<211> LENGTH: 20
<212> TYPE: DNA
<213> ORGANISM: Artificial Sequence
<220> FEATURE:
<223> OTHER INFORMATION: synthetic

<400> SEQUENCE: 50
gttccccgtg tgcatccgcg                                              20

<210> SEQ ID NO 51
<211> LENGTH: 20
<212> TYPE: DNA
<213> ORGANISM: Artificial Sequence
<220> FEATURE:
<223> OTHER INFORMATION: synthetic
```

<400> SEQUENCE: 51
ccgctcagcc tcctcgatga             20

<210> SEQ ID NO 52
<211> LENGTH: 20
<212> TYPE: DNA
<213> ORGANISM: Artificial Sequence
<220> FEATURE:
<223> OTHER INFORMATION: synthetic

<400> SEQUENCE: 52
tgacaagcgc cccttcatcg             20

<210> SEQ ID NO 53
<211> LENGTH: 20
<212> TYPE: DNA
<213> ORGANISM: Artificial Sequence
<220> FEATURE:
<223> OTHER INFORMATION: synthetic

<400> SEQUENCE: 53
ggtgacgttt cctcattggg             20

<210> SEQ ID NO 54
<211> LENGTH: 20
<212> TYPE: DNA
<213> ORGANISM: Artificial Sequence
<220> FEATURE:
<223> OTHER INFORMATION: synthetic

<400> SEQUENCE: 54
accgccgcgt tccttctacg             20

<210> SEQ ID NO 55
<211> LENGTH: 20
<212> TYPE: DNA
<213> ORGANISM: Artificial Sequence
<220> FEATURE:
<223> OTHER INFORMATION: synthetic

<400> SEQUENCE: 55
gtaacctacc ttccataaaa             20

<210> SEQ ID NO 56
<211> LENGTH: 20
<212> TYPE: DNA
<213> ORGANISM: Artificial Sequence
<220> FEATURE:
<223> OTHER INFORMATION: synthetic

<400> SEQUENCE: 56
agctagcata ttattaccag             20

<210> SEQ ID NO 57
<211> LENGTH: 20
<212> TYPE: DNA
<213> ORGANISM: Artificial Sequence
<220> FEATURE:
<223> OTHER INFORMATION: synthetic

<400> SEQUENCE: 57
ggtgcactgc tgttgcgcca             20

<210> SEQ ID NO 58
<211> LENGTH: 20

```
<212> TYPE: DNA
<213> ORGANISM: Artificial Sequence
<220> FEATURE:
<223> OTHER INFORMATION: synthetic

<400> SEQUENCE: 58
gaaccaacac tcgatcaccg                                              20

<210> SEQ ID NO 59
<211> LENGTH: 20
<212> TYPE: DNA
<213> ORGANISM: Artificial Sequence
<220> FEATURE:
<223> OTHER INFORMATION: synthetic

<400> SEQUENCE: 59
aagcggctca tctcgcagtg                                              20

<210> SEQ ID NO 60
<211> LENGTH: 20
<212> TYPE: DNA
<213> ORGANISM: Artificial Sequence
<220> FEATURE:
<223> OTHER INFORMATION: synthetic

<400> SEQUENCE: 60
gaaccaacac tcgatcaccg                                              20

<210> SEQ ID NO 61
<211> LENGTH: 20
<212> TYPE: DNA
<213> ORGANISM: Artificial Sequence
<220> FEATURE:
<223> OTHER INFORMATION: synthetic

<400> SEQUENCE: 61
ttagattctc agaatgccca                                              20

<210> SEQ ID NO 62
<211> LENGTH: 20
<212> TYPE: DNA
<213> ORGANISM: Artificial Sequence
<220> FEATURE:
<223> OTHER INFORMATION: synthetic

<400> SEQUENCE: 62
ggttgtttgt cctccaacag                                              20

<210> SEQ ID NO 63
<211> LENGTH: 20
<212> TYPE: DNA
<213> ORGANISM: Artificial Sequence
<220> FEATURE:
<223> OTHER INFORMATION: synthetic

<400> SEQUENCE: 63
ttacttacat gagaatgatc                                              20

<210> SEQ ID NO 64
<211> LENGTH: 20
<212> TYPE: DNA
<213> ORGANISM: Artificial Sequence
<220> FEATURE:
<223> OTHER INFORMATION: synthetic

<400> SEQUENCE: 64
```
atctttgcca gagccagaaa                    20

<210> SEQ ID NO 65
<211> LENGTH: 19
<212> TYPE: DNA
<213> ORGANISM: Artificial Sequence
<220> FEATURE:
<223> OTHER INFORMATION: synthetic

<400> SEQUENCE: 65
tctggaccgt gtttcggag                     19

<210> SEQ ID NO 66
<211> LENGTH: 20
<212> TYPE: DNA
<213> ORGANISM: Artificial Sequence
<220> FEATURE:
<223> OTHER INFORMATION: synthetic

<400> SEQUENCE: 66
cactggccct gtgactttga                    20

<210> SEQ ID NO 67
<211> LENGTH: 20
<212> TYPE: DNA
<213> ORGANISM: Artificial Sequence
<220> FEATURE:
<223> OTHER INFORMATION: synthetic

<400> SEQUENCE: 67
agagggtcag tggagaggtc                    20

<210> SEQ ID NO 68
<211> LENGTH: 20
<212> TYPE: DNA
<213> ORGANISM: Artificial Sequence
<220> FEATURE:
<223> OTHER INFORMATION: synthetic

<400> SEQUENCE: 68
agcctggact tgtacccaga                    20

<210> SEQ ID NO 69
<211> LENGTH: 21
<212> TYPE: DNA
<213> ORGANISM: Artificial Sequence
<220> FEATURE:
<223> OTHER INFORMATION: synthetic

<400> SEQUENCE: 69
cgtaggcggt gcttgaactt a                  21

<210> SEQ ID NO 70
<211> LENGTH: 18
<212> TYPE: DNA
<213> ORGANISM: Artificial Sequence
<220> FEATURE:
<223> OTHER INFORMATION: synthetic

<400> SEQUENCE: 70
ctacttctgg ccgaccgc                      18

<210> SEQ ID NO 71
<211> LENGTH: 24
<212> TYPE: DNA
<213> ORGANISM: Artificial Sequence

```
<220> FEATURE:
<223> OTHER INFORMATION: synthetic

<400> SEQUENCE: 71
catgtaccaa gcaatgtgcc ttta                                           24

<210> SEQ ID NO 72
<211> LENGTH: 20
<212> TYPE: DNA
<213> ORGANISM: Artificial Sequence
<220> FEATURE:
<223> OTHER INFORMATION: synthetic

<400> SEQUENCE: 72
agtttgattc ctggaggcag                                                20

<210> SEQ ID NO 73
<211> LENGTH: 22
<212> TYPE: DNA
<213> ORGANISM: Artificial Sequence
<220> FEATURE:
<223> OTHER INFORMATION: synthetic

<400> SEQUENCE: 73
atccagaggt gtcagtgcat ta                                             22

<210> SEQ ID NO 74
<211> LENGTH: 21
<212> TYPE: DNA
<213> ORGANISM: Artificial Sequence
<220> FEATURE:
<223> OTHER INFORMATION: synthetic

<400> SEQUENCE: 74
gtgccctgac cctacaagat g                                              21

<210> SEQ ID NO 75
<211> LENGTH: 21
<212> TYPE: DNA
<213> ORGANISM: Artificial Sequence
<220> FEATURE:
<223> OTHER INFORMATION: synthetic

<400> SEQUENCE: 75
gtgccctgac cctacaagat g                                              21

<210> SEQ ID NO 76
<211> LENGTH: 22
<212> TYPE: DNA
<213> ORGANISM: Artificial Sequence
<220> FEATURE:
<223> OTHER INFORMATION: synthetic

<400> SEQUENCE: 76
catgtgcggt gaattacagc tt                                             22

<210> SEQ ID NO 77
<211> LENGTH: 22
<212> TYPE: DNA
<213> ORGANISM: Artificial Sequence
<220> FEATURE:
<223> OTHER INFORMATION: synthetic

<400> SEQUENCE: 77
catgtgcggt gaattacagc tt                                             22
```

<210> SEQ ID NO 78
<211> LENGTH: 20
<212> TYPE: DNA
<213> ORGANISM: Artificial Sequence
<220> FEATURE:
<223> OTHER INFORMATION: synthetic

<400> SEQUENCE: 78
aatcataggg cacagccccc                                                        20

<210> SEQ ID NO 79
<211> LENGTH: 19
<212> TYPE: DNA
<213> ORGANISM: Artificial Sequence
<220> FEATURE:
<223> OTHER INFORMATION: synthetic

<400> SEQUENCE: 79
tgaagttccc cgaacgctg                                                         19

<210> SEQ ID NO 80
<211> LENGTH: 21
<212> TYPE: DNA
<213> ORGANISM: Artificial Sequence
<220> FEATURE:
<223> OTHER INFORMATION: synthetic

<400> SEQUENCE: 80
caccagacat acaaaccgct c                                                      21

<210> SEQ ID NO 81
<211> LENGTH: 20
<212> TYPE: DNA
<213> ORGANISM: Artificial Sequence
<220> FEATURE:
<223> OTHER INFORMATION: synthetic

<400> SEQUENCE: 81
aacttcctgc agcctctctg                                                        20

<210> SEQ ID NO 82
<211> LENGTH: 19
<212> TYPE: DNA
<213> ORGANISM: Artificial Sequence
<220> FEATURE:
<223> OTHER INFORMATION: synthetic

<400> SEQUENCE: 82
acgctggcgt acatgttga                                                         19

<210> SEQ ID NO 83
<211> LENGTH: 20
<212> TYPE: DNA
<213> ORGANISM: Artificial Sequence
<220> FEATURE:
<223> OTHER INFORMATION: synthetic

<400> SEQUENCE: 83
gtagctggct gacttctccc                                                        20

<210> SEQ ID NO 84
<211> LENGTH: 20
<212> TYPE: DNA
<213> ORGANISM: Artificial Sequence
<220> FEATURE:
<223> OTHER INFORMATION: synthetic

<400> SEQUENCE: 84
ctccatgagg aaggtggcag                                                    20

<210> SEQ ID NO 85
<211> LENGTH: 20
<212> TYPE: DNA
<213> ORGANISM: Artificial Sequence
<220> FEATURE:
<223> OTHER INFORMATION: synthetic

<400> SEQUENCE: 85
ggaccattgt ctgactcccc                                                    20

<210> SEQ ID NO 86
<211> LENGTH: 19
<212> TYPE: DNA
<213> ORGANISM: Artificial Sequence
<220> FEATURE:
<223> OTHER INFORMATION: synthetic

<400> SEQUENCE: 86
cgtctctgat cggcaaccg                                                     19

<210> SEQ ID NO 87
<211> LENGTH: 19
<212> TYPE: DNA
<213> ORGANISM: Artificial Sequence
<220> FEATURE:
<223> OTHER INFORMATION: synthetic

<400> SEQUENCE: 87
acccgtctct gatcggcaa                                                     19

<210> SEQ ID NO 88
<211> LENGTH: 22
<212> TYPE: DNA
<213> ORGANISM: Artificial Sequence
<220> FEATURE:
<223> OTHER INFORMATION: synthetic

<400> SEQUENCE: 88
tggaatactc accaagcaca ta                                                 22

<210> SEQ ID NO 89
<211> LENGTH: 22
<212> TYPE: DNA
<213> ORGANISM: Artificial Sequence
<220> FEATURE:
<223> OTHER INFORMATION: synthetic

<400> SEQUENCE: 89
cctggtttga ggttttgaag ga                                                 22

<210> SEQ ID NO 90
<211> LENGTH: 23
<212> TYPE: DNA
<213> ORGANISM: Artificial Sequence
<220> FEATURE:
<223> OTHER INFORMATION: synthetic

<400> SEQUENCE: 90
agctcccatg gaaaaggtta cag                                                23

<210> SEQ ID NO 91

```
<211> LENGTH: 21
<212> TYPE: DNA
<213> ORGANISM: Artificial Sequence
<220> FEATURE:
<223> OTHER INFORMATION: synthetic

<400> SEQUENCE: 91
aggcatgtac tggtggaagt c                                              21

<210> SEQ ID NO 92
<211> LENGTH: 21
<212> TYPE: DNA
<213> ORGANISM: Artificial Sequence
<220> FEATURE:
<223> OTHER INFORMATION: synthetic

<400> SEQUENCE: 92
aggcatgtac tggtggaagt c                                              21

<210> SEQ ID NO 93
<211> LENGTH: 22
<212> TYPE: DNA
<213> ORGANISM: Artificial Sequence
<220> FEATURE:
<223> OTHER INFORMATION: synthetic

<400> SEQUENCE: 93
ttcactctcc cctttcttga cg                                             22

<210> SEQ ID NO 94
<211> LENGTH: 22
<212> TYPE: DNA
<213> ORGANISM: Artificial Sequence
<220> FEATURE:
<223> OTHER INFORMATION: synthetic

<400> SEQUENCE: 94
ttcactctcc cctttcttga cg                                             22

<210> SEQ ID NO 95
<211> LENGTH: 21
<212> TYPE: DNA
<213> ORGANISM: Artificial Sequence
<220> FEATURE:
<223> OTHER INFORMATION: synthetic

<400> SEQUENCE: 95
tacttgtagt ccgggtggtc t                                              21

<210> SEQ ID NO 96
<211> LENGTH: 20
<212> TYPE: DNA
<213> ORGANISM: Artificial Sequence
<220> FEATURE:
<223> OTHER INFORMATION: synthetic

<400> SEQUENCE: 96
aagaggctgg agaggctgag                                                20

<210> SEQ ID NO 97
<211> LENGTH: 22
<212> TYPE: DNA
<213> ORGANISM: Artificial Sequence
<220> FEATURE:
<223> OTHER INFORMATION: synthetic

<400> SEQUENCE: 97
```

```
actgagatag agctcagggt cg                                            22

<210> SEQ ID NO 98
<211> LENGTH: 19
<212> TYPE: DNA
<213> ORGANISM: Artificial Sequence
<220> FEATURE:
<223> OTHER INFORMATION: synthetic

<400> SEQUENCE: 98
ccctgggcca tcaggaatg                                                19
```